US012318912B2

(12) United States Patent
Ghanadiof et al.

(10) Patent No.: US 12,318,912 B2
(45) Date of Patent: Jun. 3, 2025

(54) SYSTEM AND METHOD FOR INSPECTING AND MAINTAINING THE EXTERIOR ELEVATED ELEMENTS OF BUILDING STRUCTURES

(71) Applicants: Omidreza Ghanadiof, Los Angeles, CA (US); Amirhossein Ghanadiof, Esfahan (IR); Majid Ghanadiof, Esfahan (IR)

(72) Inventors: Omidreza Ghanadiof, Los Angeles, CA (US); Amirhossein Ghanadiof, Esfahan (IR); Majid Ghanadiof, Esfahan (IR)

( * ) Notice: Subject to any disclaimer, the term of this patent is extended or adjusted under 35 U.S.C. 154(b) by 0 days.

(21) Appl. No.: 18/765,325

(22) Filed: Jul. 7, 2024

(65) Prior Publication Data

US 2024/0359333 A1    Oct. 31, 2024

Related U.S. Application Data

(63) Continuation-in-part of application No. 18/444,682, filed on Feb. 17, 2024, now Pat. No. 12,033,314,
(Continued)

(51) Int. Cl.
*B25J 11/00* (2006.01)
*B25J 19/02* (2006.01)
*G01N 33/00* (2006.01)

(52) U.S. Cl.
CPC ............ *B25J 11/008* (2013.01); *B25J 19/023* (2013.01); *G01N 33/0063* (2013.01)

(58) Field of Classification Search
CPC ............ G06T 7/0008; G06T 7/90; G06T 2207/10004; G06T 2207/10016;
(Continued)

(56) References Cited

U.S. PATENT DOCUMENTS

| 3,976,384 A | 8/1976 | Matthews et al. |
| 4,550,376 A | 10/1985 | Maciejczak |

(Continued)

FOREIGN PATENT DOCUMENTS

| AU | 2011258831 | 12/2011 |
| CA | 2386173 | 4/2001 |

(Continued)

OTHER PUBLICATIONS

Vertex, 2021 (Archive.org (Wayback Machine) capture of Nov. 27, 2021), "SB721 VS. SB326: Inspection and statistical sampling methods for multifamily balconies and EES" (pp. 1-8) (Year: 2021).*

(Continued)

*Primary Examiner* — Manav Seth
(74) *Attorney, Agent, or Firm* — Makoui Law, PC; Ali Makoui

(57) ABSTRACT

A method of inspecting a balcony identifies an area of the balcony where there is no access to pass a crawler robot from the outside of the balcony into the interior space of the balcony, drills a hole into the interior space of the balcony, passes the crawler robot that includes a humidity sensor through the hole into the interior space of the balcony. The method, by the processor of an electronic device, receives humidity measurements of the interior space of the balcony from the humidity sensor, compares the humidity measurements with a threshold value, determines that at least one of the humidity sensor measurements exceeds the humidity threshold value; and generates a notification indicating the humidity in the interior space of the balcony exceeds the humidity threshold value based on the determination. The method removes the crawler robot from the interior space of the balcony and seals the hole.

7 Claims, 29 Drawing Sheets

Related U.S. Application Data which is a continuation-in-part of application No. 18/075,927, filed on Dec. 6, 2022, now Pat. No. 11,906,506.

(60) Provisional application No. 63/406,250, filed on Sep. 14, 2022, provisional application No. 63/292,078, filed on Dec. 21, 2021.

(58) Field of Classification Search
CPC ........... G06T 2207/10132; G06T 2207/30161; G06V 20/176; B25J 11/008; B25J 19/023; G01N 33/0063
See application file for complete search history.

(56) References Cited

U.S. PATENT DOCUMENTS

| | | | |
|---|---|---|---|
| 5,058,313 | A | 10/1991 | Tallon |
| 5,184,419 | A | 2/1993 | Tallon |
| 5,792,960 | A | 8/1998 | Lewis et al. |
| 6,276,209 | B1 | 8/2001 | Schafer et al. |
| 6,305,224 | B1 | 10/2001 | Stanish et al. |
| 6,496,136 | B1 | 12/2002 | Mucciardi |
| 6,593,572 | B2 | 7/2003 | Kelley |
| 6,867,421 | B1 | 3/2005 | Hunt et al. |
| 7,506,547 | B2 | 3/2009 | Jesmonth |
| 7,769,131 | B2 | 8/2010 | Wallace |
| 7,778,458 | B2 | 8/2010 | Hiraoka |
| 7,798,418 | B1 | 9/2010 | Rudd |
| 8,087,311 | B2 | 1/2012 | Merlo |
| 8,764,285 | B2 | 7/2014 | Lee et al. |
| 9,036,861 | B2 | 5/2015 | Chen et al. |
| 9,096,975 | B2 | 8/2015 | Rischmueller et al. |
| 9,283,681 | B2 | 3/2016 | Slawinski et al. |
| 9,609,288 | B1 | 3/2017 | Richman et al. |
| 9,787,978 | B1 * | 10/2017 | Jokinen ..................... G06T 3/60 |
| 10,129,508 | B1 | 11/2018 | Hillman et al. |
| 10,375,957 | B2 | 8/2019 | Su |
| 10,378,935 | B1 | 8/2019 | Raman et al. |
| 10,425,616 | B2 * | 9/2019 | Karadayi ............. G03B 17/561 |
| 10,571,454 | B2 | 2/2020 | Narasimhan et al. |
| 10,694,097 | B1 * | 6/2020 | Shirakyan ............ H04N 23/695 |
| 11,161,236 | B2 * | 11/2021 | Mallinson ............ G05D 1/0246 |
| 11,906,506 | B1 | 2/2024 | Ghanadiof et al. |
| 12,033,314 | B2 | 7/2024 | Ghanadiof et al. |
| 2002/0085093 | A1 | 7/2002 | Frigon et al. |
| 2005/0259715 | A1 | 11/2005 | Lee et al. |
| 2006/0028345 | A1 | 2/2006 | Lee |
| 2007/0286474 | A1 | 12/2007 | Dralle |
| 2009/0265193 | A1 | 2/2009 | Collins et al. |
| 2009/0303497 | A1 | 12/2009 | Hamalainen |
| 2011/0267435 | A1 | 11/2011 | Desjardins |
| 2014/0017452 | A1 | 1/2014 | Pervan et al. |
| 2014/0368378 | A1 * | 12/2014 | Crain ..................... H01Q 21/28 342/25 A |
| 2015/0208657 | A1 | 7/2015 | Ballinger, Jr. |
| 2015/0226663 | A1 | 8/2015 | McBrayer |
| 2018/0348169 | A1 | 12/2018 | Lee et al. |
| 2020/0019167 | A1 | 1/2020 | Alshamrani et al. |
| 2021/0310962 | A1 | 10/2021 | Oetiker et al. |
| 2022/0101507 | A1 * | 3/2022 | Tournier ............. G06Q 50/163 |
| 2024/0124110 | A1 | 4/2024 | Cormier |

FOREIGN PATENT DOCUMENTS

| | | | | |
|---|---|---|---|---|
| CA | 3054980 | | 3/2020 | |
| CA | 3166145 | | 6/2022 | |
| CN | 201730497 | | 2/2011 | |
| CN | 109763674 | | 5/2019 | |
| JP | 1326583 | | 11/1999 | |
| JP | 2002097713 | | 4/2002 | |
| JP | 2007185471 | | 7/2007 | |
| JP | H16215588 | | 10/2017 | |
| WO | WO 2005/019522 | | 3/2005 | |
| WO | WO-2006132745 | A1 * | 12/2006 | ......... G08B 21/0236 |
| WO | WO 2018/188042 | | 10/2018 | |
| WO | WO 2008000910 | | 6/2024 | |

OTHER PUBLICATIONS

Quintana et al., Aug. 2021, "Workplace occupant comfort monitoring with a multi-sensory and portable autonomous robot" (pp. 1-23) (Year: 2021).*

Lopez et al., 2013, "WatchBot: A building maintenance and surveillance system based on autonomous robots" (pp. 1559-1571). (Year: 2013).*

Rodic et al., 2009, "Ambient Intelligent Robot-Sensor Networks for Environmental Surveillance and Remote Sensing" (pp. 39-44) (Year: 2009).*

Portions of prosecution history of U.S. Appl. No. 18/075,927, filed Jan. 31, 2024, Ghanadiof, Omidreza, et al., Portions of prosecution history of commonly owned U.S. Appl. No. 18/075,927, listed as item #2 above, including actions and/or responses/amendments (43 pages).

Ohya, Akihisa, et al, "Development of Inspection Robot for Under Floor of House," IEEE International Conference on Robotics and Automation, May 12-17, 2009 (Year 2019), pp. 1429-1434.

Lin, Wenshy, et al., "Study on Wood Board Defect Detection Based on Artificial Neural Network," The Open Automation and Control Systems Journal, Month unknown, 2015, pp. 290-295.

Borik, Ahmed, et al., "Caged Quadrotor Drone for Inspection of Central HVAC Ducts," Advances in Science and Engineering Technology International Conferences, Mar. 26, 2019-Apr. 10, 2019 (Year 2019), 7 pages.

Ding, Fenglong, et al, "Detecting Defects on Solid Wood Panels Based on an Improved SSD Algorithm," Sensors 2020, 20(18), Sep. 2020, pp. 1-17.

Author unknown, "ET20 Instruction Manual Wireless Borescope," Klein Tools, available online at <https://data.kleintools.com/sites/all/product_assets/documents/instructions/klein/ET20-Manual_Web.pdf>, Jan. 2019, pp. 1-5.

Author unknown, "Daifuku Chain Conveyors Technical Selection Guide for Conveyor Components," Daifuku, available online at <https://www.daifuku.com/us/solution/resourcelibrary/brochure/>, month unknown but before Dec. 2021; 4 pages, including cover page, pp. 4.1-4.2, and back cover.

Author unknown, "Carbide Tipped Heavy Duty Holesaws," MaxTool Corp., available online at <http://mymaxtool.com>, date unknown but before Dec. 2021, p. 1.

Author unknown, "Key Specification 4"x60" Balcony Inspection Vent Model # CS2011-PG-Removable," Brandguard Vents, available online at <https://www.brandguardvents.com/removable-balcony-vents/>, date unknown but before Dec. 2021, p. 1.

Author unknown, "Troglotrek Truly portable, battery-operated pipe crawler system," Strahl, available online at <https://www.fiberscope.net/sewer-crawler-troglogator/>, date unknown but before Dec. 2021, pp. 1-6.

Portions of prosecution history of U.S. Appl. No. 18/444,682, filed Jun. 19, 2024, Ghanadiof, Omidreza, et al., Portions of prosecution history commonly owned U.S. Appl. No. 18/444,682, listed as item #18 above, including actions and/or responses/amendments (10 pages).

* cited by examiner

SYSTEM AND METHOD FOR INSPECTING AND MAINTAINING THE EXTERIOR ELEVATED ELEMENTS OF BUILDING STRUCTURES

CLAIM OF BENEFIT TO PRIOR APPLICATIONS

This application is a continuation-in-part of U.S. patent application Ser. No. 18/444,682, filed on Feb. 17, 2024, published as U.S. Patent Publication 2024/0193757. U.S. patent application Ser. No. 18/444,682 is a continuation-in-part of U.S. patent application Ser. No. 18/075,927, filed on Dec. 6, 2022, issued as U.S. Pat. No. 11,906,506. U.S. patent application Ser. No. 18/075,927 claims the benefit of U.S. Provisional Patent Application Ser. No. 63/292,078, filed on Dec. 21, 2021, and U.S. Provisional Patent Application Ser. No. 63/406,250, filed on Sep. 14, 2022. The contents of U.S. patent application Ser. No. 18/444,682, U.S. patent application Ser. No. 18/075,927, U.S. Provisional Patent Application 63/292,078, and U.S. Provisional Patent Application 63/406,250 are hereby incorporated by reference.

BACKGROUND

Wood is one of the most prevalent building materials. Several conditions such as wood rot and bolt and nail rust may affect the health of a wood frame building. Exterior elevated elements of a building such as decks, porches, balconies, stairways, walkways, landings, etc., may become deteriorated over time. Many of these deterioration conditions may occur to the beams, joists, bridging, ledgers, bolts, and nails inside of the exterior elevated elements of a building and may not be detectable by eye inspection.

BRIEF DESCRIPTION OF THE DRAWINGS

The various embodiments of the present system and method for inspecting and maintaining the exterior elevated elements of building structures now will be discussed in detail with an emphasis on highlighting the advantageous features. These embodiments depict the novel and non-obvious system and method for inspecting and maintaining the exterior elevated elements of building structures shown in the accompanying drawings, which are for illustrative purposes only. These drawings include the following figures, in which like numerals indicate like parts.

DETAILED DESCRIPTION

Figure 1A:
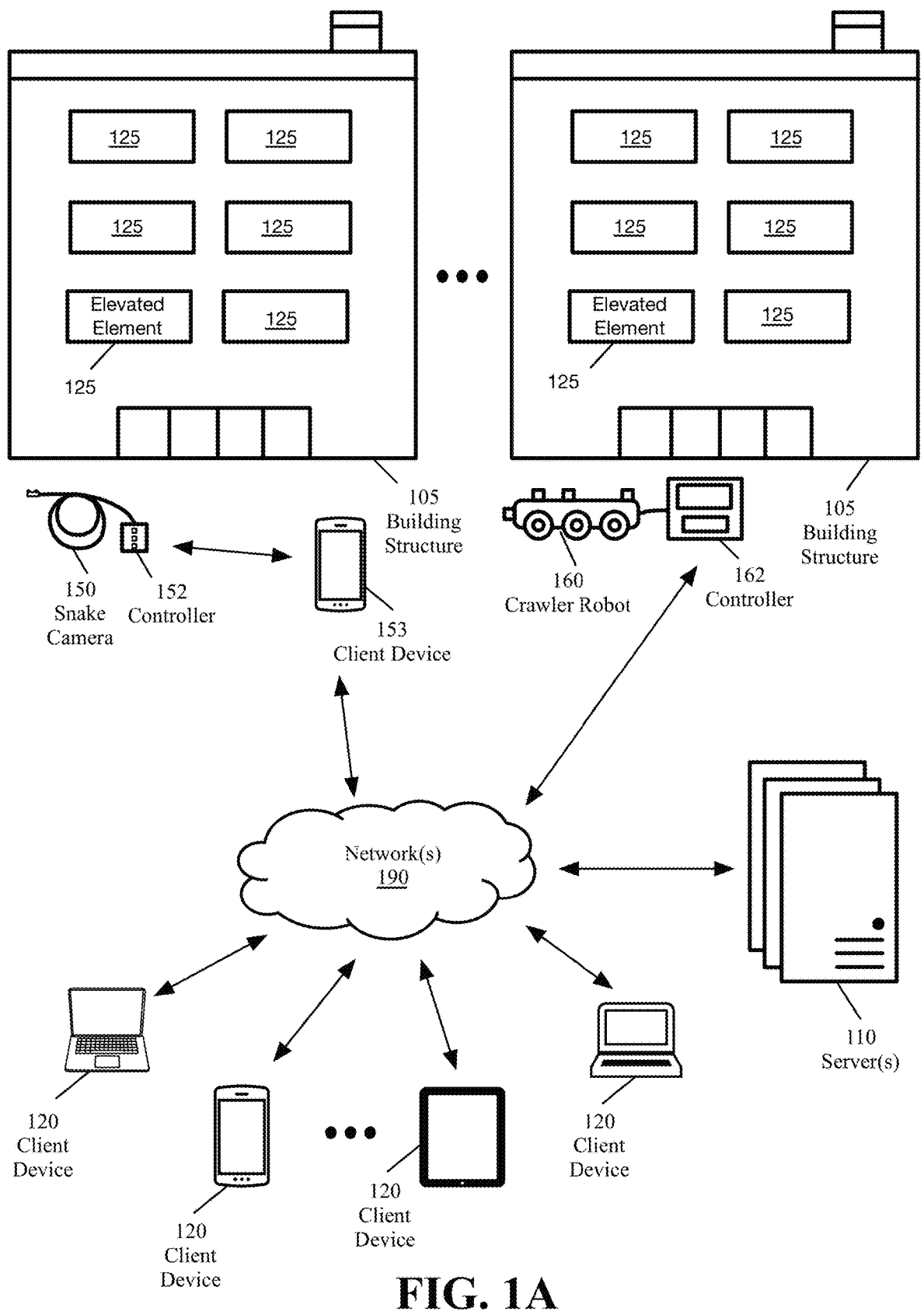
FIGS. 1A-1B are functional diagrams illustrating an example embodiment of a system for inspecting and maintaining exterior elevated elements of building structures, according to various aspects of the present disclosure.

One aspect of the present embodiments includes the realization that the traditional eye inspection of the exterior elevated elements of a building may not reveal the health condition of the beams, joist, bridging, legers, bolts, and nails that are inside these elevated elements. The eye inspection of these exterior elements may require demolishing a portion of these structures that is large enough to allow eye inspection. In addition, once an exterior elevated element is inspected, and is repaired if damaged, there is no system and method for maintaining the health of the elevated element and preventing future wood rot to the wood and rust to the bolts and nails inside the structure. Furthermore, there is no automatic method of identifying buildings that include exterior elevated elements that may be subject to government required inspections.

The present embodiments, as described in detail below, solve the above-mentioned problems by providing a method and system for inspecting and maintaining the exterior elevated elements building structures, such as decks, porches, balconies, stairways, walkways, landings, etc., for wood rot and for the health condition of joists, beams, foundation, etc. Inspections may be required by different state and municipal governments and/or may be requested by homeowner associations, owners, lenders, lessors, insurers, or other persons or entities who may have a legal or financial interest in a building.

Some of the present embodiments provide a method of automatically identifying buildings that may include any exterior elevated elements. Some of these embodiments may use satellite images that are either publicly available through such services as, for example, and without limitations, Google Maps, Apple Maps, etc., or satellite images that may be purchased or licensed through third party providers.

The satellite images may then be analyzed by image processing software that is executed by processors of one or more severs to identify building features that may be indicative of elevated elements. The list of such buildings may then be provided to any interested party that may need a list of such buildings for building code enforcement, advertisement, etc.

In addition to, or in lieu of using satellite images, some embodiments may provide tabulated data available from government agencies and third parties that lists different attributes of buildings in a geographical region. Examples of the building attributes that may be provided in this type of tabulated data may include, for example, and without limitations, name of the owner(s), the owner type (e.g., individual, trust, etc.), the owner(s) contact information, owners vesting rights (e.g., joint tenant, revocable trust, trust, survivor, family trust, community property, etc.), the situs direction (e.g., north, south, east, or west), the property's address, the property's legal description (e.g., lot and track number), the property's census track and block number, the property's latitude and longitude address, the land and the building areas, the year built, the data of the issuance of the certificate of opponency, number of bedrooms, number of bathrooms, parking area, parking type (e.g., covered or open), construction type (e.g., wood frame, metal frame, etc.), patio type, porch type, foundation type, room type, number of floors, flood zone code, name and address of the homeowner association (if any), etc.

The processor(s) of the server(s), in some embodiments analyze the tabulated data to identify buildings that may or may not require inspection. For example, some embodiments may determine that a building is not wood frame or otherwise does not have a wood structure that may need inspection. Some states or municipalities may not require inspection for single story buildings, or for structures such as a balcony, that may be less than a threshold distance from ground.

In addition to, or in lieu, of the tabulated data, some embodiments may allow user entered data (e.g., entered by an owner, an inspector, a property manager, etc.) to be used to determine whether or not a building may include exterior elevated elements and/or whether or not the exterior elevated elements may require inspection.

The processor(s) may use one or more criteria such as the age of a building, the certificate of occupancy date of the building, the frame type, the number of the stories, the geographical zone, etc., to determine whether or not a building may require inspection for exterior elevated elements. The processor(s), in some embodiments, may also provide an initial cost and duration for the inspection.

Once a building that requires inspection is identified and authorization for the inspection is received, some embodiments may drill a hole (e.g., by a bi-metal hole saw, a drill, and/or a hammer) in a small area of an exterior elevated element that requires inspection. The hole may be wide enough to allow a snake camera (also referred to as a snake endoscope camera, a borescope camera, or a snake inspection camera) or a crawler robot that includes a camera to pass through the hole. The snake camera, in some embodiments, may be a miniaturized device for minimized impact on the exterior elevated element.

The camera of the snake camera or the camera of the crawler robot may then be used to take still images and/or videos images. The still images and/or the video images are referred to herein as images for brevity. The images may be stored in a computer readable medium associated with the snake camera or the crawler robot, may be livestreamed, and/or may be transmitted to a remote location for storage and analysis.

The processor(s) may determine the existence of wood rot or other damages by identifying contrasted areas in the images. Some embodiments may use different artificial intelligent (AI) or machine learning (ML) learning techniques, such as, for example, and without limitations, deep learning, to identify wood rot or other damages.

In some embodiments, the AI or ML may use a model that may be trained by data specific to the images taken by cameras from exterior elevated element that may or may not have wood rot or other specific health conditions. In addition to, or in lieu of, an automatic method, some embodiments, may allow humans to inspect the images either during a livestream play or by inspecting the recorded images. Once an issue such as wood rot or other damages is identified in an exterior elevated element, the processor(s) in some embodiments, may provide a cost and duration for repairs.

Some embodiments may include other sensors, such as, for example, and without limitations, humidity sensors, moisture sensors, etc., to collect additional data from the hole. the additional data may be used, in addition to, or in lieu of the images, to determine whether dry rot and other damages may exist in the exterior elevated element.

Some embodiments may close the hole with a cap (e.g., rubber, plastic, silicone, etc.) to prevent moisture to get into the hole. Some embodiments may install one or fans inside the hole to keep the hole dry. The fans, in some embodiments may be controlled by one or more processors. The processor(s) that control a fan may be an integrated part of the fan (e.g., inside the fan), in a control hub used to just control the same fan, may be in a control hub located in the same building and may control one or more other fans, or may be located at a remote location controlling fans in many buildings. The hub may be connected to the fan wirelessly or by wires.

Sensors, such as, for example, and without limitations, humidity sensors, moisture sensors, temperature sensors, etc., may be installed inside the hole to monitor humidity, moisture, temperature, etc., inside the hole. The sensor(s) may be integrated part(s) of the fan (e.g., may be installed on the outside or in a cavity on the fan's frame) or may be separate from the fan. The fans may be powered by alternative current (AC) from the building and/or by one or more batteries. The batteries, in some embodiments, may be replaceable and/or rechargeable.

In order to conserve energy and reduce wear and tear in a fan, some embodiments may use sensor data, such as humidity, moisture, or temperature in order to start or stop the fan. For example, the fan's processor and/or the hub may turn on the fan only when the humidity, moisture, and/or temperature inside the hole is above a threshold.

Some embodiments may install one or more ventilation windows in the exterior elevated element to circulate air to prevent dry rot of the wood in the interior of the exterior elevated element. The ventilation window, in some embodiments, may have a railing and bearing that may allow the window to be fixed to joists that with different distances from each other.

The remaining detailed description describes the present embodiments with reference to the drawings. In the drawings, reference numbers label elements of the present embodiments. These reference numbers are reproduced below in connection with the discussion of the corresponding drawing features.

Figure 1B:
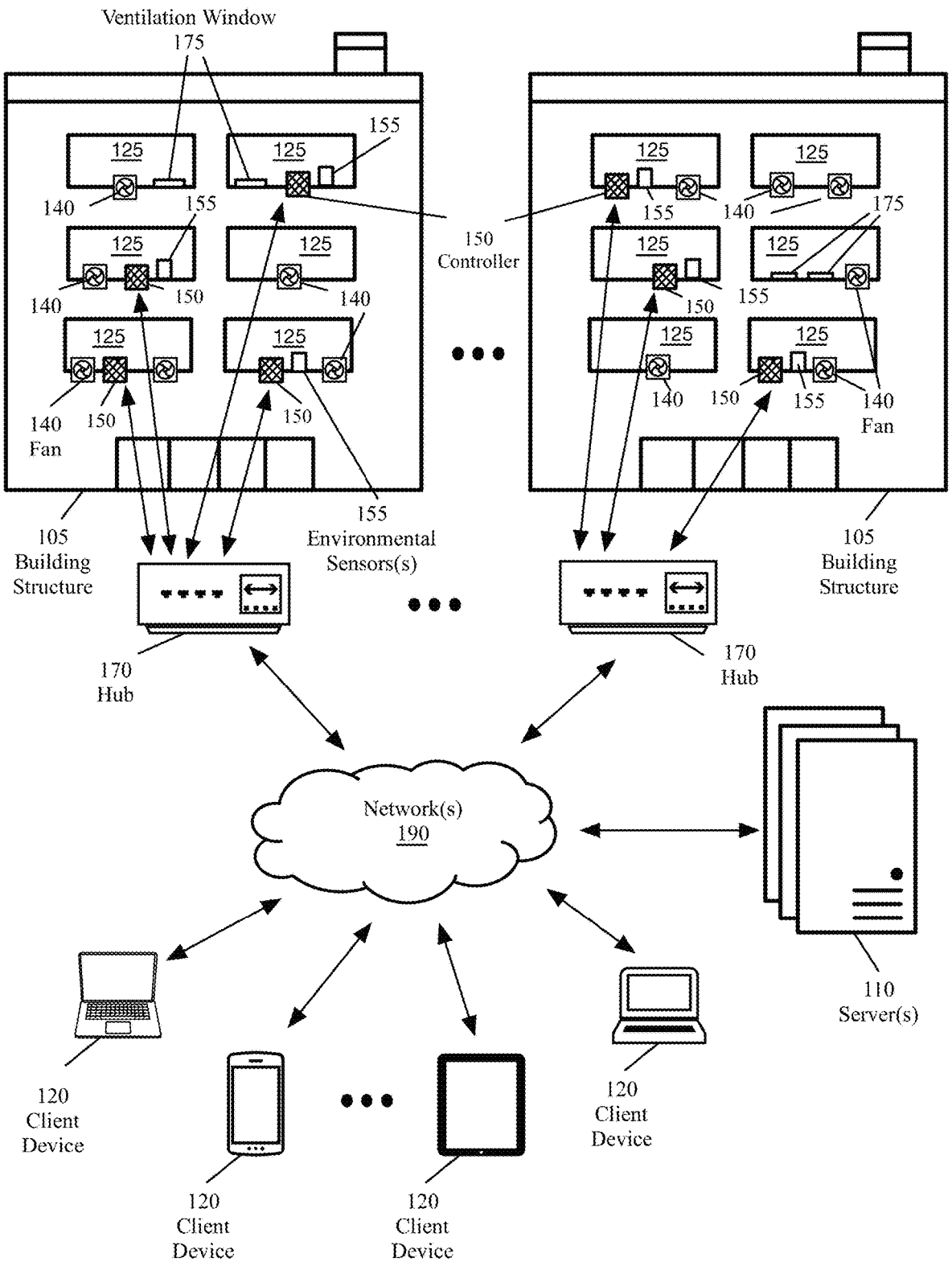

FIGS. 1A-1B are functional diagrams illustrating an example embodiment of a system for inspecting and maintaining exterior elevated elements of building structures, according to various aspects of the present disclosure. With reference to FIGS. 1A-1B, the building structures 105 may include one or more exterior elevated elements 125. Examples of the exterior elevated elements 125 include, balconies, decks, porches, stairways, walkways, landings, etc.

Figure 2:
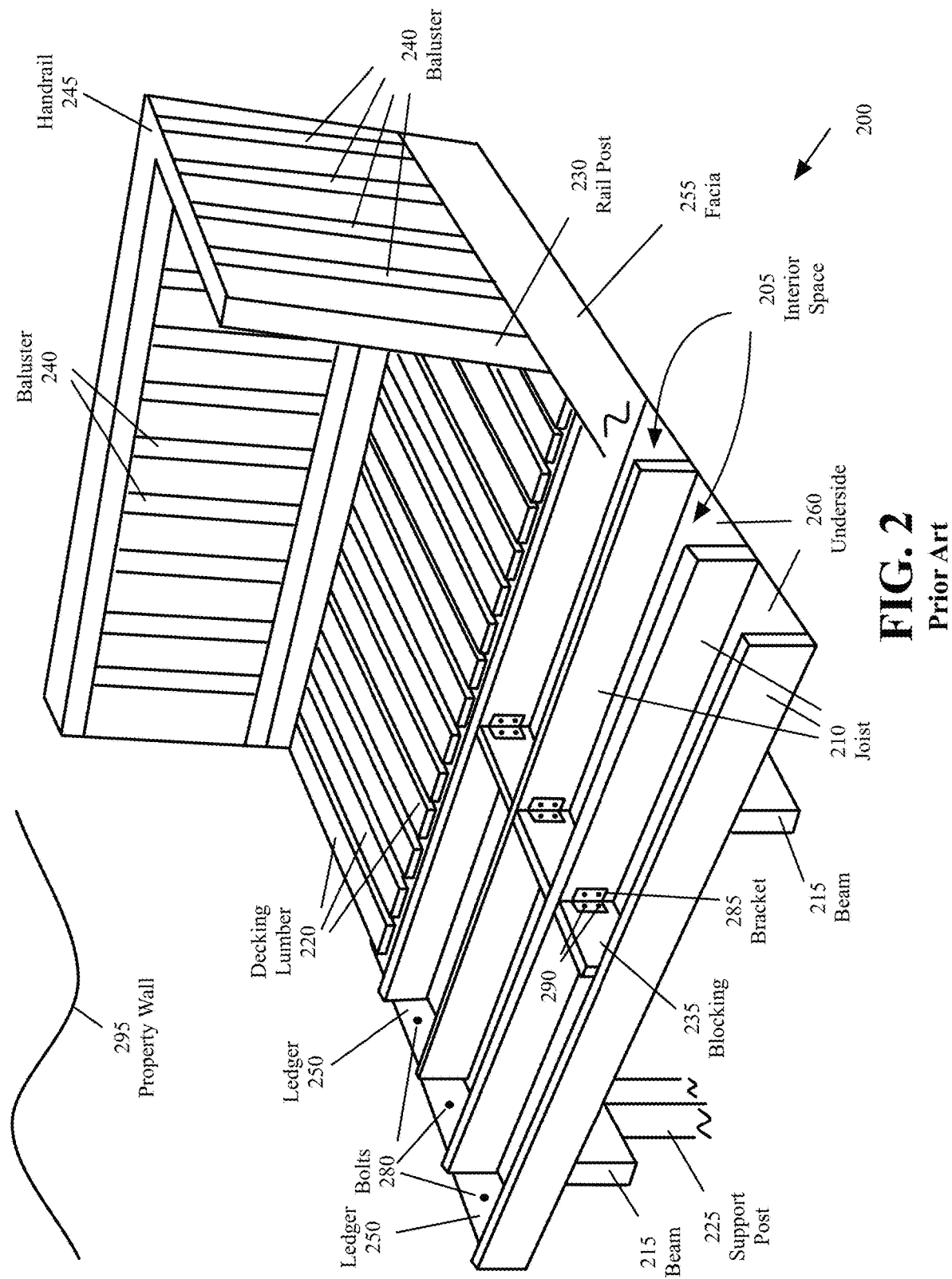
FIG. 2 shows different components of an exemplary exterior elevated element of a building structure, according to prior art.

FIG. 2 shows different components of an exemplary exterior elevated element of a building structure, according to prior art. With reference to FIG. 2, the exterior elevated element 200 in the example of FIG. 2 may be a balcony. As shown, the balcony 200 may include several joists 210, several beams 215, several decking lumbers 220, several support posts 225, several rail posts 230, several blockings 235, several balusters 240, several handrails 245, several ledgers 250, a facia 255, an underside 260, etc.

In order to show the interior of the balcony 200, only portions of the decking lumbers 220 and the facia 250 are shown in FIG. 2. The joists 210, the beams 215, the decking lumbers 220, the support posts 225, the rail posts 230, the blockings 235, the balusters 240, the handrails 245, the ledgers 250, the facia 255, and underside 260 may be, at least partially, made of wood. Different wooden components of the balcony 200 may be connected to each other or to the property wall 295 by metallic parts, such as blots, 280, brackets, 285, nails 290, etc. For clarity, only some of the components of the balcony 200 are labeled in the figure.

The balcony 200 may include a covering over the decking lumbers 230 to facilitate walking over the balcony. The balcony 200 may include water proofing insolation to prevent water (e.g., rainwater) from seeping inside the balcony through any space around the decking lumbers 230, the facia 255, the underside 260, and the property wall 295. The space delimited by the decking lumbers 220, the facia 255, the underside 260, and the property wall 295 is referred to herein as the interior space (or the interior) 205 of the balcony 200.

It should be noted that, depending on the size and design of a balcony, the number and the arrangement of the components of a balcony may be different than the balcony 200. For example, in the balcony 200, the beams 215 are shown outside of the interior space 205 of the balcony 200 while other balconies may include one or more beams inside the interior space. Other types of exterior elevated elements of a building may include similar and/or different wooden or metallic components as the balcony 200.

The interior space 205 of exterior elevated elements is an enclosed area with little to no air circulation. For wood frame structures, joists, ledgers, beams, blocking, and posts inside the interior space of the exterior elevated elements may deteriorate due to wood rot. Wood rot (also referred to as dry rot) is a condition that is caused by wood being exposed to water and moisture. Damp wood creates an ideal condition for fungal growth that weakens and decays the wood structure. In addition, a damp environment may result in metallic components, such as, nails, nuts, bolts, and brackets that are used to attach pieces of wood together to rust.

Inspection of the exterior elevated elements may be required by different state and municipal governments and/or may be requested by homeowner associations, owners, buyers, lenders, lessors, insurers, or other persons or entities who may have a legal or financial interest in a building.

The traditional eye inspection of the exterior elevated elements of a building may not reveal the health condition of the beams, joist, bridging, ledgers, bolts, nails, etc., that are inside the interior space of these elevated elements. The eye inspection of the interior spaces of these exterior elements may require demolishing portions of these structures that are large enough to allow eye inspection.

Referring back reference to FIG. 1A, some embodiments may drill a hole and may use custom-made snake cameras 150 and/or custom-made crawler robots 160 to inspect interiors of the exterior elevated elements 125. For example, some embodiments may use a drill with a hole saw (or hole cutter) blade to drill a hole into the interior of the exterior elevated elements 125 of a building 105. The size of the hole may be made wide enough to allow a snake camera 150 or a crawler robot 160 to pass through the hole and reach the interior space of the exterior elevated element. The hole is typically made through the underside (e.g., the underside 260 of FIG. 2) of the exterior elevated elements to prevent damage to the waterproofing material over the top (e.g., the deckling lumbers 220 of FIG. 2) of the exterior elevated elements.

Figure 3:
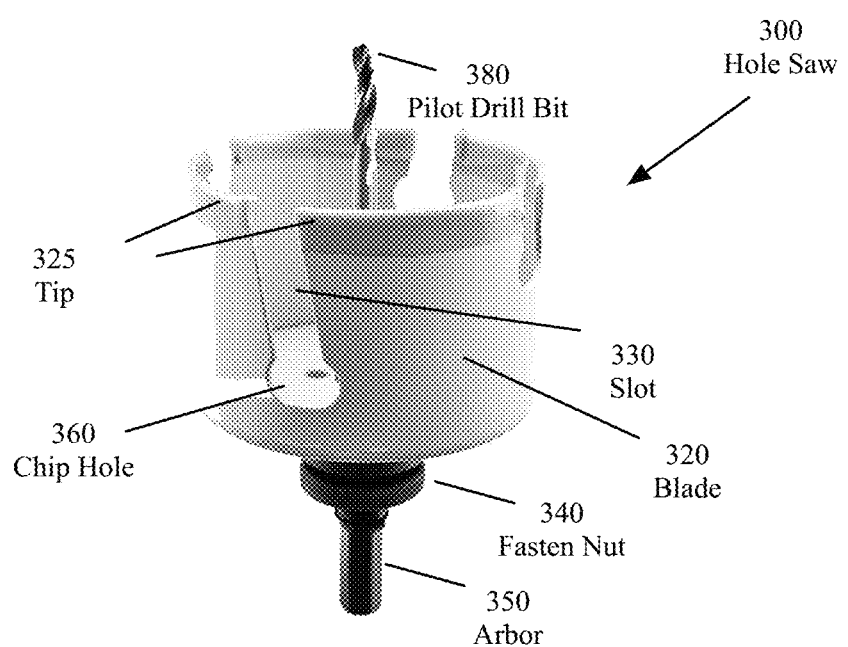
FIG. 3 is a perspective view of a hole saw, according to prior art.

FIG. 3 is a perspective view of a hole saw, according to prior art. With reference to FIG. 3, the hole saw 300 may have a cylindrical shape whose annular rotation may create a hole into the interior space of an exterior elevated element. The hole saw 300 may be installed on a drill by the fasten nut 340 and the arbor 350. The hole saw 300 may include several blades 320 with metallic (e.g., carbide) tips 325.

The optional pilot drill bit 380 may be used to make a pilot hole in the material to reduce walking. The hole saw blades may be bimetal, where the edges of the blades may be made of a hardened metal (e.g., high-speed steel (HSS)) to allow the edges to stay sharp while the rest of the body of the blades may be made of a flexible metal to allow the blade to flex. The hole saw 300 may include a variable tooth pitch for fast and smooth cutting. The hole saw 300 may include chip holes (or gullets) 360 for easy removal of wood plug from inside the hole saw 300. An example of a hole saw may be the Hole Dozer hole saw.

Referring back to FIG. 1A, instead of a hole saw, other types of drills and blades, for example, hammer drills, may be used to make the hole into the interior of the exterior elevated elements 125 in some embodiments. Once the hole is made, a custom-made snake camera (also referred to as a snake endoscope camera, a borescope camera, or a snake inspection camera) 150 or a crawler robot 160 may be used to inspect the interior of the exterior elevated element 125.

Figure 4A:
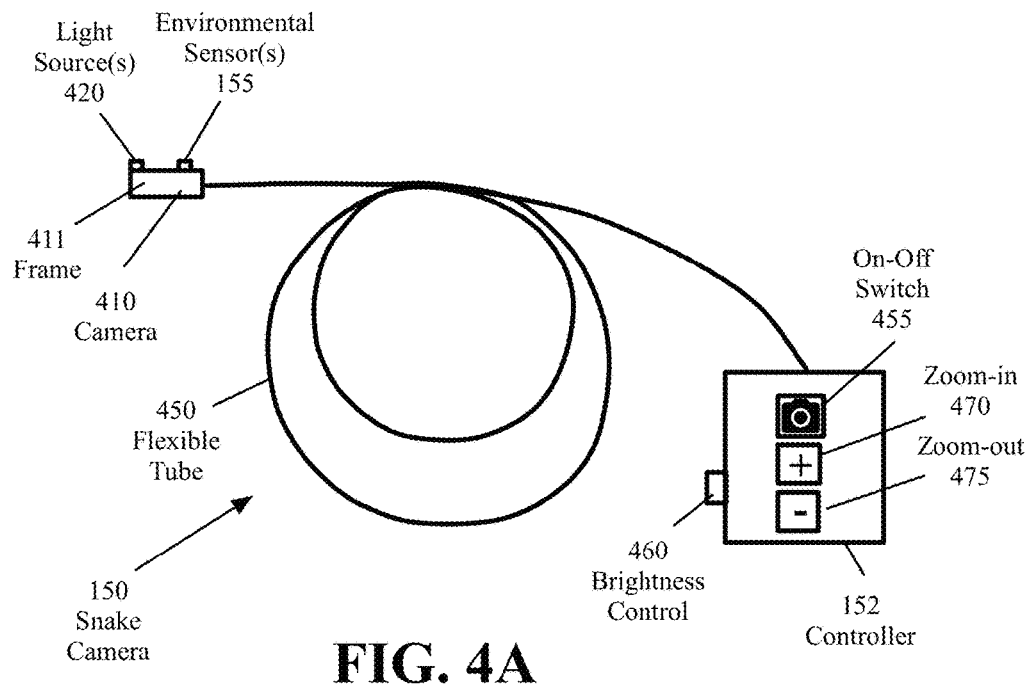
FIG. 4A is a schematic front view of a custom-made snake camera and the associated controller, according to different aspects of the present disclosure.
Figure 4B:
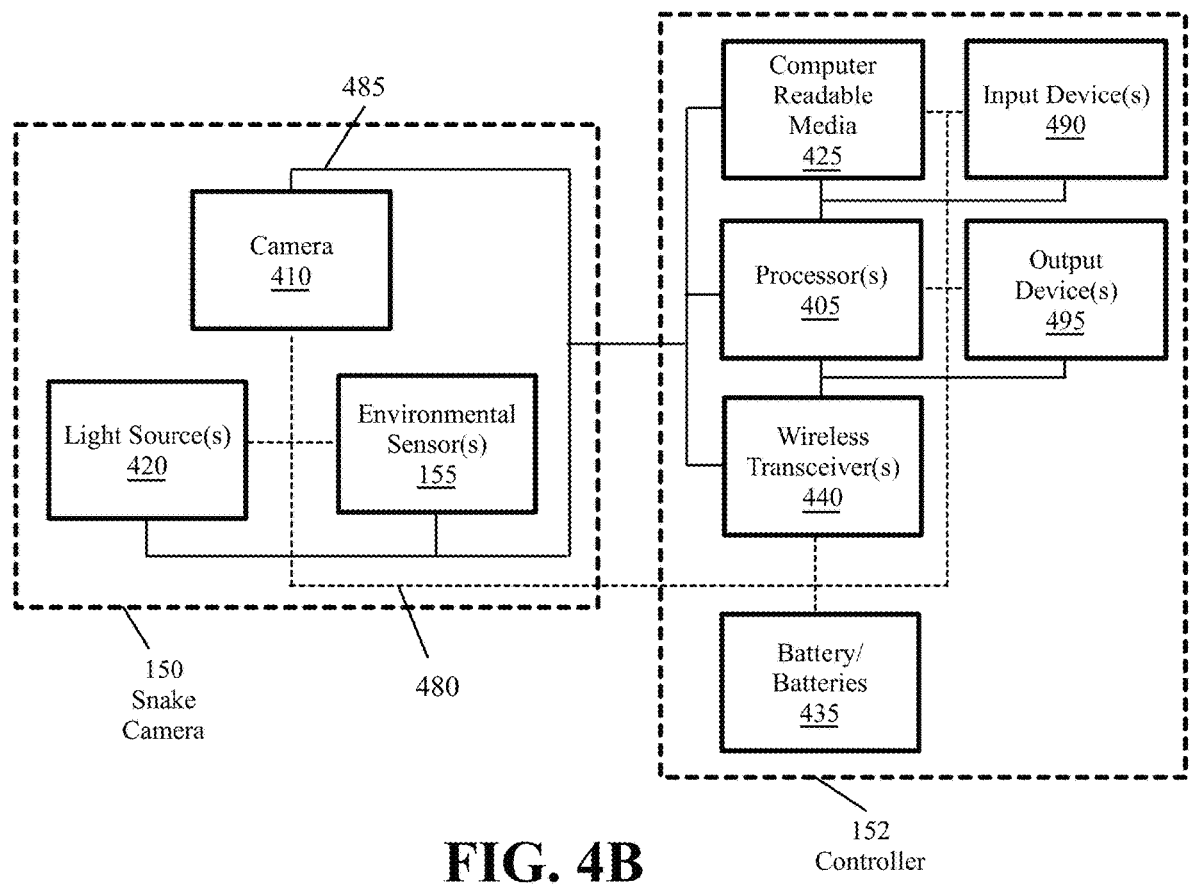
FIG. 4B is a functional block diagram of the components of the custom-made snake camera of FIG. 4A, according to different aspects of the present disclosure.

FIG. 4A is a schematic front view of a custom-made snake camera and the associated controller, according to different aspects of the present disclosure. FIG. 4B is a functional block diagram of the components of the custom-made snake camera of FIG. 4A, according to different aspects of the present disclosure. With reference to FIGS. 4A-4B, the snake camera 150 may include a camera 410 with one or more lenses, one or more light sources 420, and a controller 152. The camera 410 and the light sources 420 may be mounted at the end of a flexible tube 450. The camera 410 may capture video images and/or still images. The snake camera may be a miniaturized device to minimize the impact on the exterior elevated element.

Some of the snake cameras of the present embodiments may include one or more environmental sensors 155. The environmental sensors 155 may measure the environmental conditions of the interior space of an exterior elevated element. The environmental sensors 155 may include, for example, and without limitations, a humidity sensor, a moisture sensor, and/or a temperature sensor. Different components of the snake camera may be connected to each other by several wires 485, a portion of which may nm through the flexible tube 450.

As wood rot is caused in a moist environment, the environmental sensors 155 of the present embodiments provide the technical advantage of determining whether the interior space of an exterior elevated element is suitable for the growth of dry rot causing fungi. In some embodiments, the sensors' measured parameters may be used (e.g., by the server(s) 110 of FIGS. 1A-1B) to determine whether the humidity or moisture within the interior space of an exterior elevated element is above a threshold that may promote the growth of the dry rot causing fungi. As described further below, some embodiments may install one or more fans and/or one or more ventilation windows to circulate the air between the interior space and outside of the exterior elevated elements of buildings to reduce the humidity and moisture to prevent dry rot.

With further reference to FIGS. 4A-4B, the controller 152 may be a hand-held controller. The controller 152 may include one or more processors 405, one or more computer readable media 425, one or more wireless (e.g., and without limitations, Wi-Fi or Bluetooth) transceivers 440, one or more batteries 435, one or more input devices 490, and/or one or more output device(s) 495. The processor(s) 405 may control the operations of the camera 410 and the light source(s) 420 through the on-off switch 455, the light source brightness control 460, the zoom-in control 470, and/or the zoom-out control 475.

The battery (or batteries) 435 may be rechargeable and/or replaceable and may provide power to different components of the controller 152 and the snake camera 150 through one or more wires 480. The wireless transceivers 440 may provide wireless connectivity with one or more external electronic devices.

The input device(s) 490 may include the brightness control 460, the zoom-in control 470, and the zoom-out control 475. The output device(s) 495 may include one or more light-emitting diodes (LEDs) to show on-off or other status and a display to show the images captured by the camera 410.

Referring back to FIG. 1A, the controller 152 of the snake camera 150 may be configured to wirelessly communicate to a client device 153, for example, through an application program (app) that may be downloaded into the client device 153. The processor(s) 405 (FIG. 4B) may receive images (e.g., video images and/or still images) captured by the camera 410 and may send the images to the client device 153 (FIG. 1A). The processor(s) 405 (FIG. 4B) may receive environmental parameters, such as humidity, moisture, and temperature, measured by the environmental sensor(s) 155 and may send the parameters to the client device 153.

In addition to, or in lieu of, the controls 460-475, the app on the client device 153 may provide options to zoom-in and zoom-out the camera 410 (FIG. 4) and/or to adjust the brightness of the light source(s) 420. The client device 153 app may allow the video captured by the camera 410 to be viewed on a display of the client device 153, to be stored in the computer readable media of the client device 153, and/or to be transmitted to external electronic devices, such as the server(s) 110, through one or more networks 190. The network(s) 190 may be one or more of the Internet, intranets, cellular networks, networks of servers/backend devices, and/or users' networks (e.g., Wi-Fi, Ethernet, etc.).

The environmental sensors 155, in some embodiments, may be integrated in the snake camera 410. Alternatively, the environmental sensors 155, in some embodiments, may be attached to the frame 411 of the snake camera 410. In these embodiments, the snake camera may be used to move the environmental sensors 155. The environmental sensors 155 may send their measurements (either wirelessly or thorough the flexible tube 450 to the processor(s) 505 of the controller. The environmental sensors 155, in some embodiments, may include wireless transmitters and/or a processor that may be included in an integrated chip (IC) with the rest of the sensor circuitry (collectively shown as item 155).

Figure 5A:
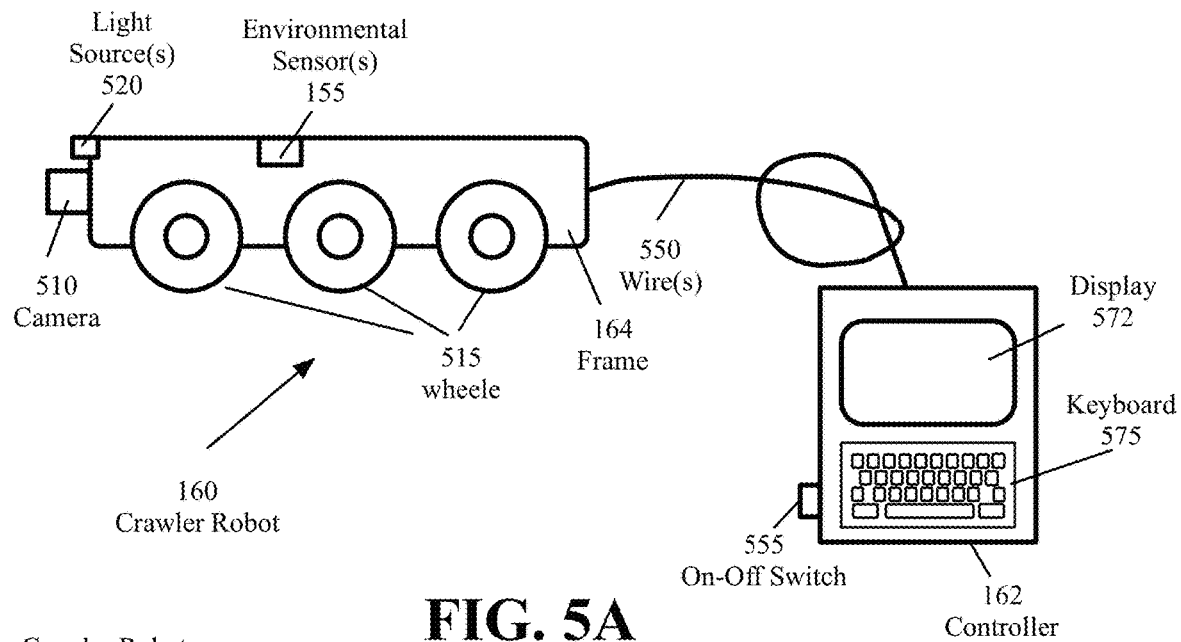
FIG. 5A is a schematic front view of a custom-made crawler robot and the associated controller, according to different aspects of the present disclosure.
Figure 5B:
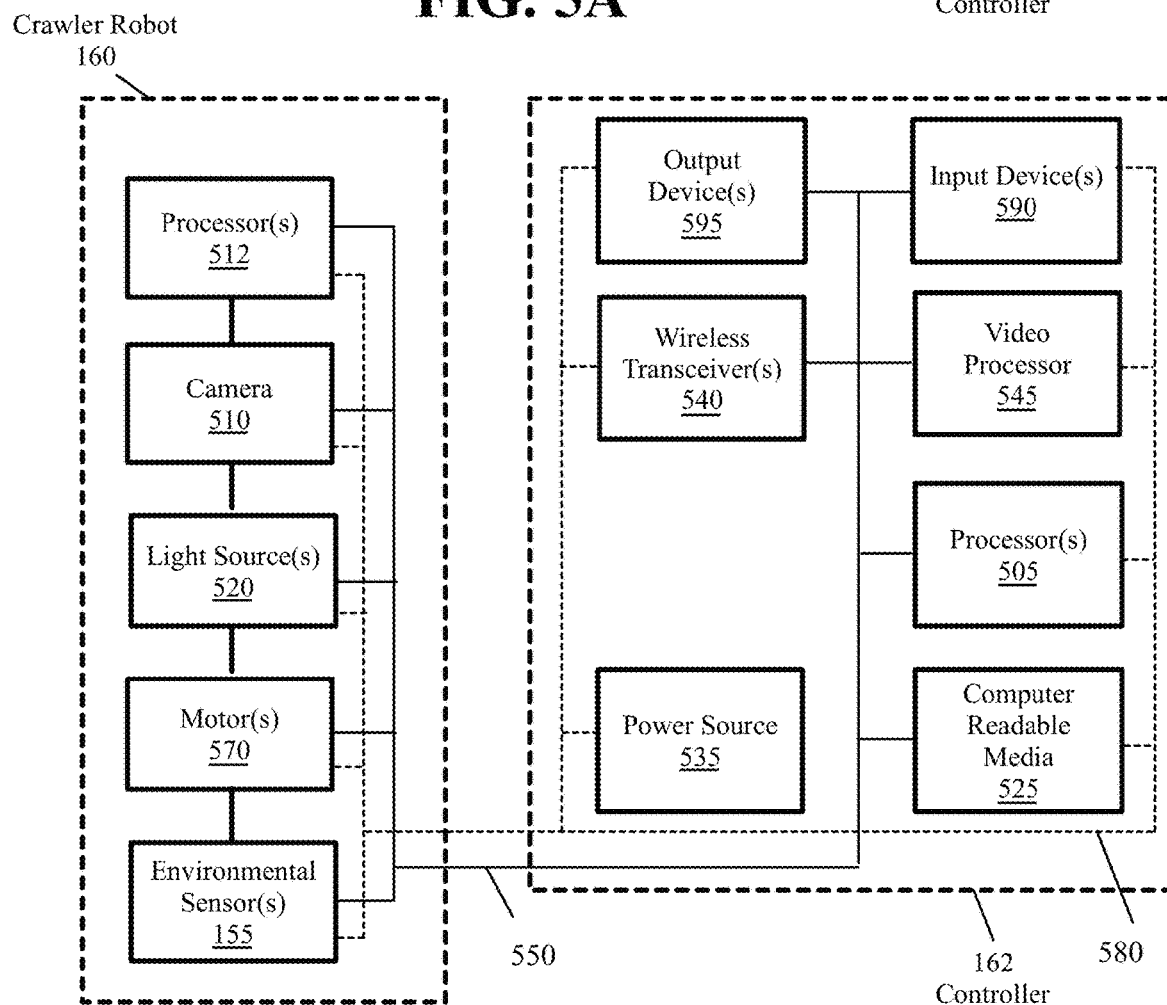
FIG. 5B is a functional block diagram of the components of custom-made crawler robot of FIG. 5A, according to different aspects of the present disclosure.

FIG. 5A is a schematic front view of a custom-made crawler robot and the associated controller, according to different aspects of the present disclosure. FIG. 5B is a functional block diagram of the components of custom-made crawler robot of FIG. 5A, according to different aspects of the present disclosure. With reference to FIGS. 5A-5B, the crawler robot 160 may include a camera 510 with one or more lenses, one or more light sources 520, one or more motors 570, a frame 164, several wheels 515, and one or more processors 512. The crawler robot 160 may be connected to a controller 162 by one or more wires 550. The wheels 515 may be located, for example, on the two sides of the frame 164.

The camera 510 may capture video images and/or still images. Some of the crawler robots of the present embodiments may include one or more environmental sensors 155, which may be similar to the environmental sensors 155 of FIGS. 1A-1B and 4A-4B. The environmental sensors 155 of the present embodiments provide the technical advantage of determining whether the interior space of an exterior elevated element is suitable for the growth of dry rot causing fungi. In some embodiments, the sensors' measured parameters may be used (e.g., by the server(s) 110 of FIGS. 1A-1B) to determine whether the humidity or moisture within the interior space of an exterior elevated element is above a threshold that may promote the growth of the dry rot causing fungi.

With further reference to FIGS. 5A-4B, the controller 162 may be a computing device with a display 572, a keyboard 575, and an on-off switch 555. The controller 162 may include one or more processors 505, one or more computer readable media 525, one or more wireless transceivers 540, a power source 535, one or more input devices 590, and/or one or more output devices 595. The controller 162, in some embodiments, may include a video processor 545 to, at least partially, process images captured by the camera 510. The processor(s) 505 may control the operations of the camera 510 (e.g., capture images, zoon-in, or zoom-out) and the light source(s) 520 (e.g., increase or decrease brightness) through the on-off switch 555, the keyboard 575, and the display 570.

In some embodiments, the processor(s) 505 of the controller 162 may control different components of the crawler robot 160 by sending signals to the processor(s) 512 of the crawler robot 160. In response to receiving signals from the processor(s) 505 of the controller 162, the processor(s) 512 of the crawler robot 160 may send signals to different components of the crawler robot 160 and/or may provide images taken by the camera 510, measurements made by the environmental sensor(s) 155, etc., to the processor(s) 505 of the controller 162. In some embodiments, the processor(s) 505 of the controller 162 may directly control different components of the crawler robot by sending signals to these components. For brevity, the following discussions are made general to cover both scenarios where the processor(s) 505 of the controller 162 may control different components of the crawler robot 160 either directly or through the processor(s) 512 of the crawler robot 160.

The processor(s) 505 may control the movements of the crawler robot 160 through the motor(s) 570. The processor(s) 505 may receive commands through the display 572 (e.g., when the display is a touchscreen) and/or the keyboard 575 to move and steer the crawler robot inside the interior space of an exterior elevated element of a building. The processor(s) 505 may send one or more signals to the motor(s) 570 to rotate the wheels 515 and/or to turn the wheels 515 left or right. The motor(s) 570 may include, for example, and without limitations, DC motors, stepper motors, servo motors, etc.

The controller 162 may include a power source 535 that may provide power to different components of the controller 162 and the crawler robot 160 through one or more wires 580. The power source 535 may include a power adapter that may connect to an alternative current (AC) outlet. In addition to, or in lieu of the power adapter, the power source 535 may include one or more batteries that may be rechargeable and/or replaceable.

The controller 162 may include one or more wireless (e.g., and without limitations, Wi-Fi or Bluetooth) transceivers 540 to provide wireless connectivity with an external electronic device. In addition to, or in lieu of the wireless transceivers 540, the controller 162 may include wired connectivity through the network(s) 190 (FIGS. 1A-1B) with one or more external devices. Different components of the crawler robot 160 and/or the controller 162 may be connected to each other by several wires 550

The input device(s) 590 may include the keyboard 575. The output device(s) 595 may include the display 570. In some embodiments, the display 570 may be a touchscreen display and may function as both an input and an output device.

Figure 5C:
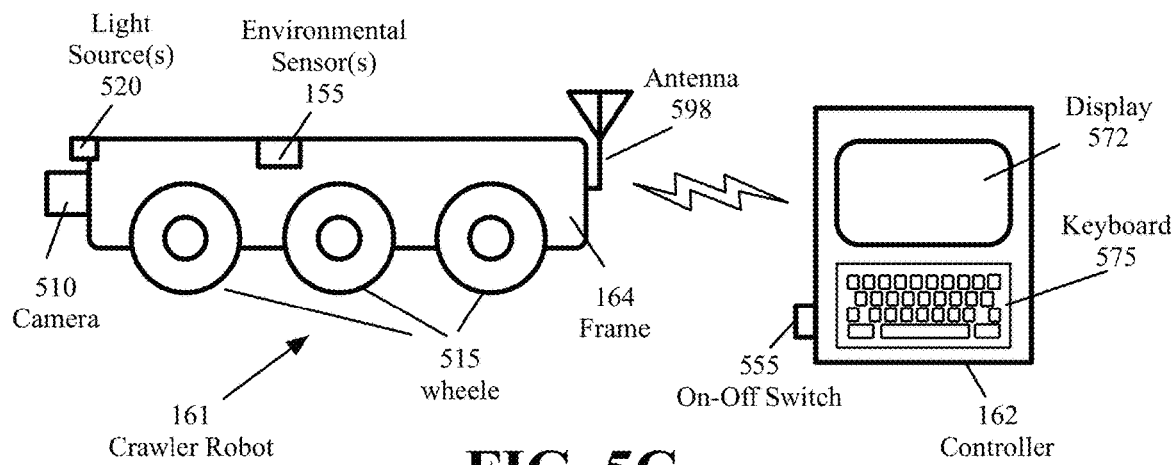
FIG. 5C is a schematic front view of a wirelessly controlled custom-made crawler robot and the associated controller, according to different aspects of the present disclosure.
Figure 5D:
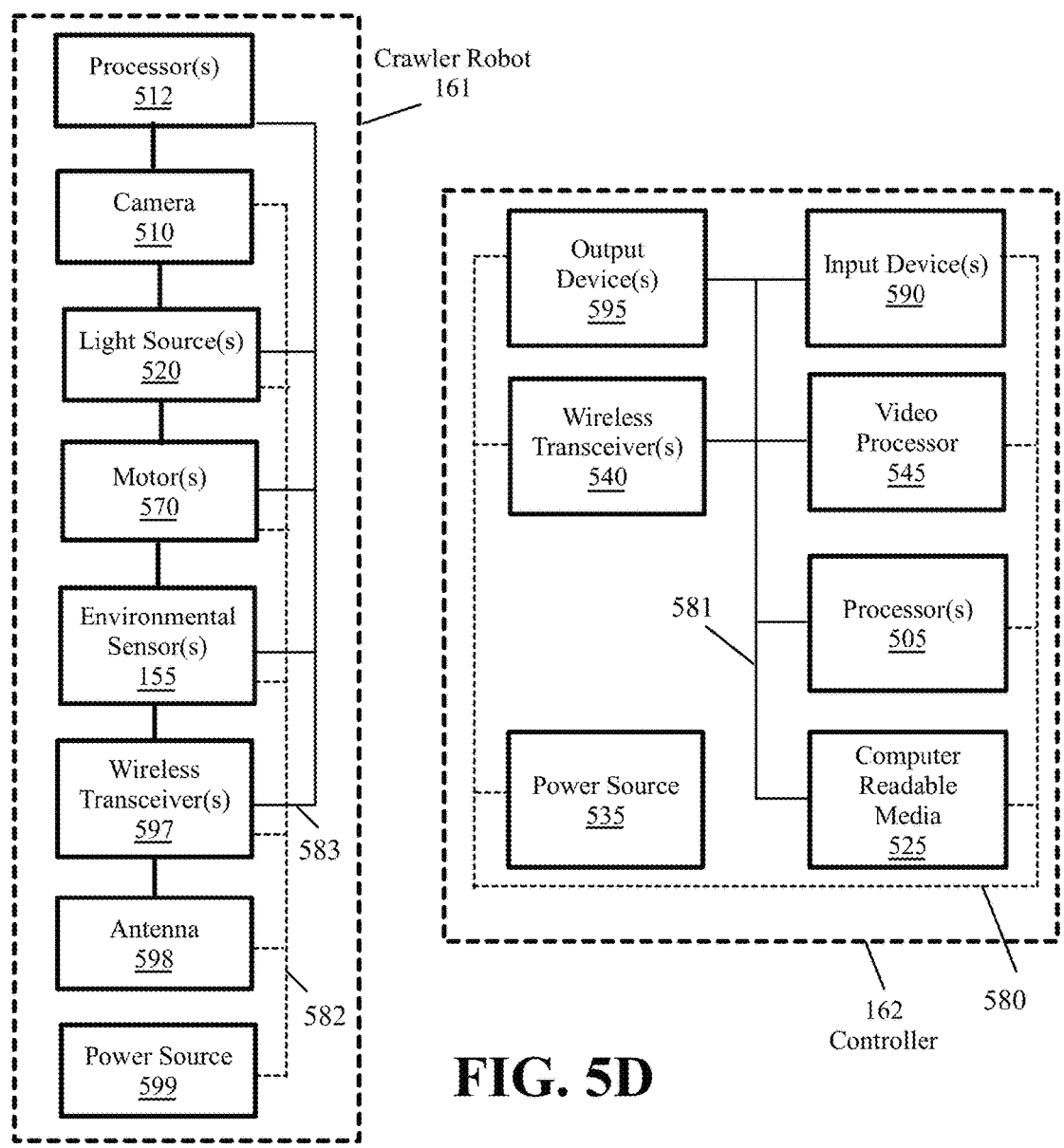
FIG. 5D is a functional block diagram of the components of custom-made crawler robot of FIG. 5C, according to different aspects of the present disclosure.

FIG. 5C is a schematic front view of a wirelessly controlled custom-made crawler robot and the associated controller, according to different aspects of the present disclosure. FIG. 5D is a functional block diagram of the components of custom-made crawler robot of FIG. 5C, according to different aspects of the present disclosure. With reference to FIGS. 5C and 5D, the crawler robot 161 may be include an antenna 598 and one or more wireless transceivers 597. The controller 162 may wirelessly control the operations of the crawler robot 161.

In some embodiments, the processor(s) 505 of the controller 162 may control different components of the crawler robot 161 by sending signals to the processor(s) 512 of the crawler robot 161. In response to receiving signals from the processor(s) 505 of the controller 162, the processor(s) 512 of the crawler robot 161 may send signals to different components of the crawler robot and/or may provide images taken by the camera 510, measurements made by the environmental sensor(s) 155, etc., to the processor(s) 505 of the controller 162. In some embodiments, the processor(s) 505 of the controller 162 may directly control different components of the crawler robot 161 by sending signals to these components. For brevity, the following discussions are made general to cover both scenarios where the processor(s) 505 of the controller 162 may control different components of the crawler robot either directly or through the processor(s) 512 of the crawler robot 161.

The processor(s) 505 may control the movements of the crawler robot 161 through the motor(s) 570. The processor(s) 505 may receive commands through the display 572 (e.g., when the display is a touchscreen) and/or the keyboard 575 to move and steer the crawler robot inside the interior space of an exterior elevated element of a building. The processor(s) 505 may wirelessly send one or more signals to the motor(s) 570 to rotate the wheels 515 and/or to turn the wheels 515 left or right. The processor(s) 505 may wirelessly control the operations of the camera 510 (e.g., capture images, zoon-in, or zoom-out) and the light source(s) 520 (e.g., increase or decrease brightness) through the on-off switch 555, the keyboard 575, and the display 570.

The crawler robot 161 may include a power source 599, which may include one or more batteries that may be rechargeable and/or replaceable. The power source 599 may provide power to other components of the crawler robot, through one or more wires 582.

Different components of the crawler robot 161 may be connected to each other by a bus and/or several wires 583. Different components of the controller 162 may be connected to each other by a bus and/or several wires 581. Other components of the crawler robot 161 and the controller 162 may be similar to the corresponding components of the crawler robot 160 and the controller 162 of FIGS. 5A-5B.

The environmental sensors 155, in some embodiments, may be integrated in the crawler robots 160 or 161. In these embodiments, the environmental sensors 155 may send the environmental measurements to the process(s) 152 of the crawler robot, which may in turn send the environmental measurements to the processor(s) 505 of the controller 162.

Alternatively, the environmental sensors 155, in some embodiments, may be attached to the frame 164 of the crawler robots 160 or 161. In these embodiments, the crawler robots 160 or 161 may be used to move the environmental sensors 155. The environmental sensors 155 may send their measurements (either wirelessly as shown in FIGS. 5C-5D or thorough wire(s) 500 as shown in FIGS. 5A-5B) to the processor(s) 505 of the controller. The environmental sensors 155, in some embodiments, may include wireless transmitters and/or a processor that may be included in an integrated chip (IC) with the rest of the sensor circuitry (collectively shown as item 155).

Some embodiments may provide a user interface (e.g., through the display of the client device 153 or the display of the controller 162) to monitor the images captured by the camera of the snake camera 150 or the camera of the crawler robot 160, respectively. The images may be monitored live and/or may be recorded and stored for review at a later time. The captured images, in some embodiments, may be sent to one or more external electronic devices, such as, the client devices 120 and/or the server(s) 110 for live monitoring and/or reviewing at a later time. The client devices 120 and 153 may be smartphones, tablets, laptop computers, desktop computers, etc. The images may be used to navigate the snake camera or the crawler robot in the interior space of the exterior elevated element of the building while the snake camera or the crawler robot are inside the interior space. The images may also be analyzed to identify the existence of dry rot on the wooden parts of the interior space.

In addition to, or in lieu of monitoring by a human, some embodiments may analyze the images captured by the cameras by electronic devices, such as the server(s) 110, the controller 162, and/or the client device 153 to determine the existence of dry rot in the interior space of exterior elevated elements 125 of a building and/or to determine rust in the metallic components (e.g., nuts, bolts, brackets, nails, etc.) in the interior space of exterior elevated elements 125.

For example, the areas of wood that are damaged by dry rot may have a different color and/or a different color intensity. Color intensity, also called chroma or saturation, is a measure of the brightness or dullness of a color. The areas of wood that are damaged by dry rot may become browner or darker than the undamaged wood. The surface areas of wood that are damaged by dry rot may break into cubical like cracking or checking. The color differences among different areas of the wood, the color intensity differences among different areas of the wood, and/or the shape and size of any cracks on the wood surface may be used to determine whether the wood is damaged by dry rot.

Some embodiments may use AI to analyze the images captured from the interior spaces of the exterior elevated elements of buildings to determine the existence and/or the extent of wood rot damage. The AI model may be trained by images of healthy wood and wood that is damaged by the dry rot. The AI model may be trained to detect the color differences, the color intensity differences, and/or the differences between the shape and size (e.g., length and width) of any cracks on the healthy wood surface and the wood surface damaged by the dry rot.

The metallic components, such as nuts, bolts, brackets, nail, etc., may rust due to moisture. The rusted metal may have a different color and/or different color intensity than the metal that is not rusted. The AI model, in some embodiments, may be trained to detect the existence of rust in the metallic components using the color differences and/or color intensity differences between the rusty and healthy metallic components.

In some embodiments, for example, when the exterior elevated element is a balcony, the images captured from the interior spaces of the exterior elevated elements may be analyzed to determine the slope of the balcony surface. When the slope of the balcony is more than a threshold, the balcony may be a deficient balcony with slanted slope that may require repair.

After detecting the existence of dry rot in the captured images, further analysis may be done by the AI model to determine the extent of the wood damage and to determine a structural integrity rating. The results of the analysis may be stored and/or sent to one or more of the client devices 120.

Some embodiments may provide an estimate of the labor amount and material required to repair the wood damage based, at least partially, on the extent of (e.g., the total area affected by) the wood rot damage and/or the type of the exterior elevated element damaged by wood rot. The estimate may be provided to one or more of the client devices 120.

With reference to FIG. 1B, some embodiments may install one or more environmental sensors 155, such as moisture sensors, humidity sensors, and/or temperature sensors inside the interior space of the exterior elevated elements 125 of the buildings 105 to monitor the moisture, humidity, and/or temperature inside the interior space. The environmental sensors 155 may be communicatively coupled (e.g., by wires) to the controllers 150. One controller 150 may be communicatively coupled to one or more environmental sensors 155. The controller 150 may receive measurements of the environmental parameters, such as, moisture, humidity, temperature, etc., from the environmental sensors 155 and may send the environmental parameters wirelessly or through wires to a hub 170.

Each hub 170 may be installed inside or on the exterior of a building 105. Each hub 107 may receive environmental parameters from one or more controllers 155. A hub 170 may locally store the environmental parameters, may analyze the environmental parameters, and/or may send the environmental parameters and/or the analysis results through the network(s) 190 to one or more external electronic devices such as the client devices 120 and/or the server(s) 110.

The processor(s) of the hubs 170, the server(s) 110, and/or the client devices 120 may analyze the environmental parameters by comparing the value of the environmental parameters, such as, humidity, moisture, and/or temperature, with the corresponding thresholds to determine whether the environment in the interior space of the exterior elevated elements 125 may be suitable for dry rot growth. The processor(s) of the hubs 170, the server(s) 110, and/or the client devices 120 may generate a warning if the environmental parameters exceed the corresponding threshold for a threshold time period (e.g., several hours, several days, etc.).

Some embodiments may install one or more fans (e.g., on the underside 260 (FIG. 2) of the exterior elevated elements of a building) to circulate air between the interior and the outside of the exterior elevated elements. The number and power of the fans, in some embodiments, may be determined (e.g., by a processor of a server 110) based on the size of the interior space and/or whether the joists 210 (FIG. 2) may divide the interior space of an exterior elevated element into several separate compartments (or joist areas), the environmental parameter measurements received from the environmental sensors, and/or the average humidity, moisture, and/or temperature of the geographical area where the property is located.

In addition to, or in lieu of, installing the fans, some embodiments may install one or more ventilation windows 175. The number and the size of the ventilation windows may be determined (e.g., by a processor of a server 110) based on the size of the interior space and/or whether the joists 210 (FIG. 2) may divide the interior space of an exterior elevated element into several separate compartments (or joist areas), the environmental parameter measurements received from the environmental sensors, and/or the average humidity, moisture, and/or temperature of the geographical area where the property is located.

Figure 6A:
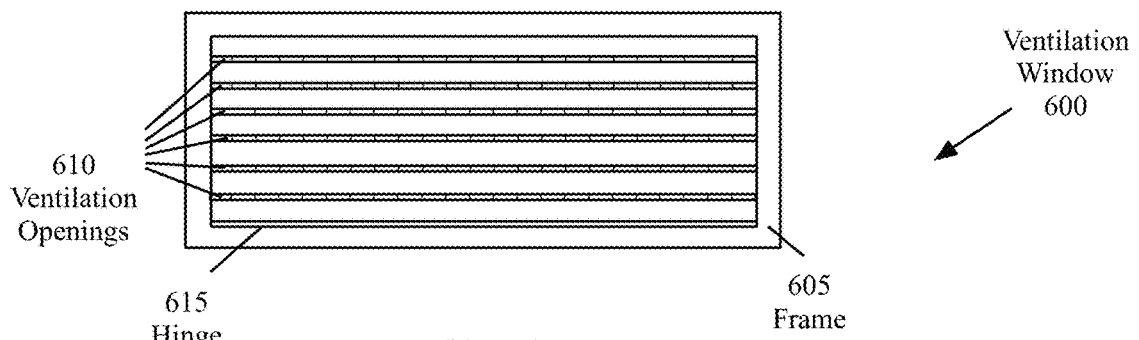
FIG. 6A is a bottom view and FIG. 6B is a top view of a ventilation window that may be installed on the underside of an exterior elevated element of a building, according to various aspects of the present embodiments.
Figure 6B:
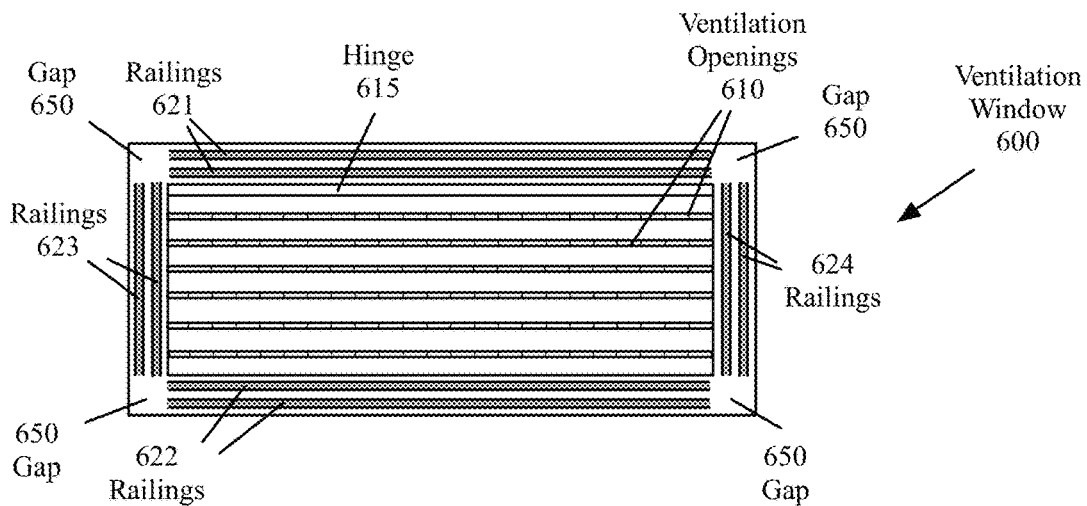

Some embodiments may provide ventilation windows that includes movable brackets to facilitate attaching the ventilation windows to the joists 210 (FIG. 2) of an exterior elevated element of a building. FIG. 6A is a bottom view and FIG. 6B is a top view of a ventilation window 600 that may be installed on the underside of an exterior elevated element of a building, according to various aspects of the present embodiments. The ventilation window 600 may be one of the ventilation windows 175 of FIG. 1B.

FIG. 6A shows the visible side of the ventilation window 600 that faces down when it is installed on the underside of the exterior elevated element. FIG. 6B shows the side of the ventilation window 600 that faces the interior of the exterior elevated element.

With reference to FIG. 6A, the ventilation window 600 may include a frame 605, several ventilation openings 610, and a hinge 615. In the depicted embodiment, the ventilation openings 610 span across the length of the ventilation window 600. In some embodiments, the ventilation openings 610 may span across the width of the ventilation window 600. In some embodiments, the ventilation openings 610 may include many small opening resembling a net.

The ventilation window 600, in some embodiments, may be ember and fire stopping. For example, the ventilation window 600, in some embodiments, may include a mesh structure behind the ventilation openings 610 to prevent the passage of ember and fire flames through the ventilation openings 620. The hinge 615 may facilitate opening of the ventilation window 600 and inspecting the interior space of the exterior elevated elements.

With reference to FIG. 6B, the frame 605 may include several pairs of railings 621-624. The depicted embodiment includes four pairs of railings 621-624. Other embodiments may include only two pairs of railings, for example either the two pairs of railing 621 and 622 or the two pairs of railing 623 and 624.

Figure 7:
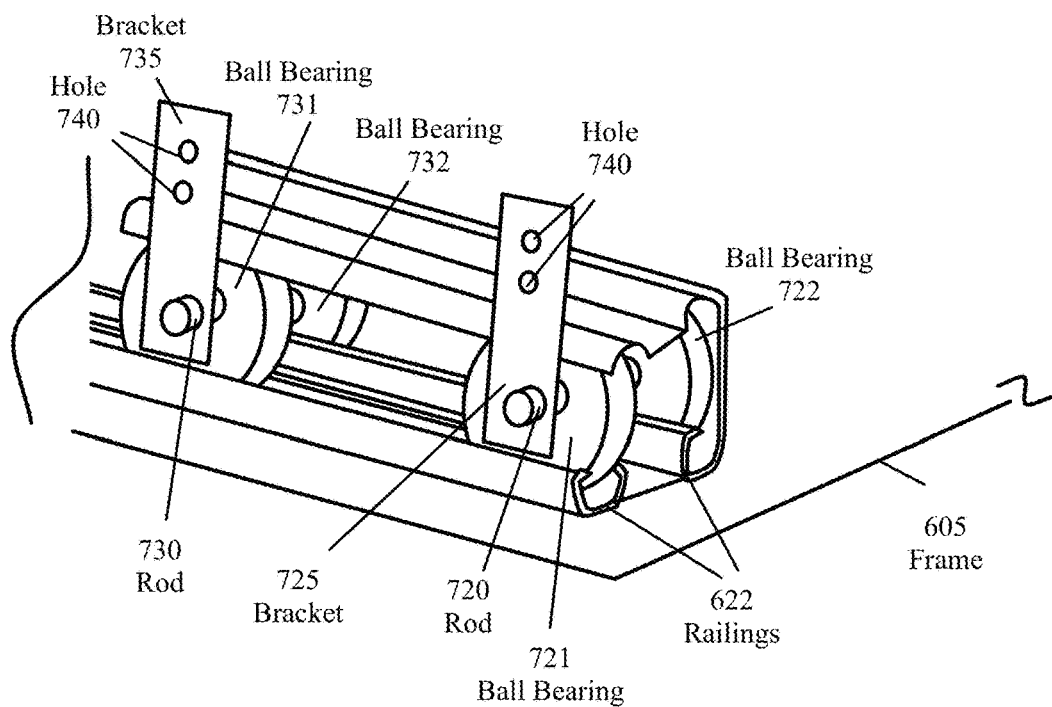
FIG. 7 illustrates a portion of a pair of railings of FIG. 6B, according to various aspects of the present disclosure.

FIG. 7 illustrates a portion of a pair of railings of FIG. 6B, according to various aspects of the present disclosure. With reference to FIG. 7, the railings may be, for example, the railings 622 of FIG. 6B. As shown, several pairs of ball bearings 721-722 and 731-732 (only two pairs are shown in FIG. 7 for brevity) may move across the railings 622. Each pair of ball bearings 721-722 and 731-732 may be connected to each other by a corresponding rod 720 and 730. It should be noted that when the ball bearing pairs 721-722 or 731-732 rotate, the corresponding rods 720 and 730, which are fixed to the center of the ball bearing pairs do not rotate.

As shown, each rod 720 and 730 is connected to a corresponding bracket 725 and 735. The brackets may be, for example, metallic plates. Each bracket 725 and 735 may include one or more holes 740. In operation, when the ventilation window 600 (FIGS. 6A-6B) is installed on the underside of an exterior elevated element, the pair of ball bearings (e.g., the pair of ball bearings 721-722) may be moved across the railings 622 until the corresponding bracket 725 is adjacent to a joist. The bracket may then be fixed to the joist by nails, bolts, screws, etc. The same operation may be repeated for other ball bearing pairs by moving a ball bearing pair across the railings 622 until the corresponding bracket is adjacent to a joist. The bracket may then be fixed to the joist by nails, bolts, screws, etc. The same operation may be repeated for ball bearing pairs on other railings (e.g., the railing 621 of FIG. 6B) until the ventilation window is securely attached at several places to one or more joists. It should be noted that the number and location of the holes on the brackets of FIGS. 7, 9, 12, 13, and 15 may be different in different embodiments.

In some embodiments, pairs of ball bearings may be inserted into (or removed from) the railings 612-624 through the gaps 650. therefore, as many pairs of ball bearings that are needed may be inserted into the railings based on the spacing between the joists, the weight of the ventilation window, etc. In the depicted embodiment, the brackets 725 and 735 are attached to the rods 720 and 730 such that the surface of the brackets are parallel to the surface of the ball bearings 721-722 and 731-732. In other embodiments, the brackets 725 and 735 may be attached to the rods 720 and 730 such that the surface of the brackets are perpendicular to the surface of the ball bearings 721-722 and 731-732 (e.g., facing to the right or to the left, in the depicted orientation of FIG. 7). Some embodiments may provide two different groups of ball bearings and brackets, in one group, the surface of the brackets may be parallel to the surface of the ball bearings and in other group the surface of the brackets may be perpendicular to the surface of the ball bearings. an end user may then select the proper group of ball bearings and brackets for a particular installation job, depending on the desired orientation of the installed ventilation window and the orientation of the joists in the interior space of the exterior elevated elements.

Figure 8:
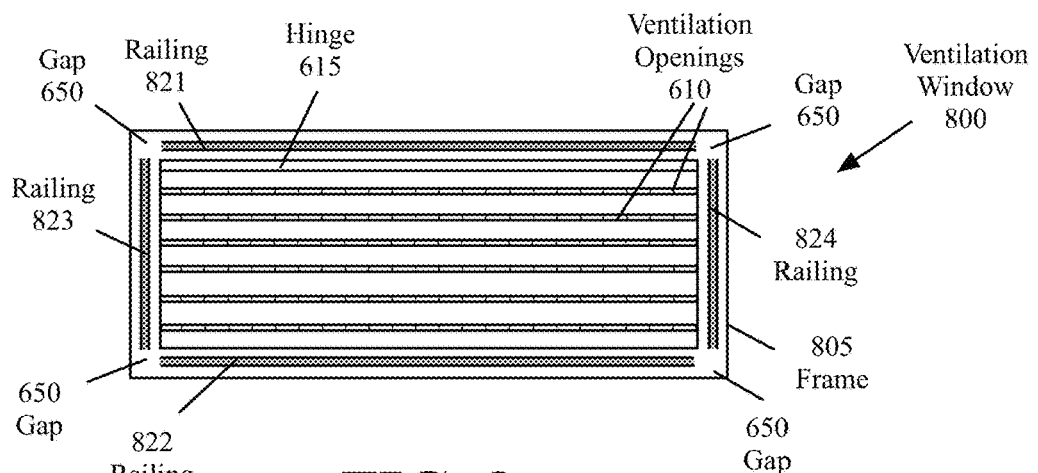
FIG. 8 is a bottom view of an alternative ventilation window that may be installed on the underside of an exterior elevated element of a building, according to various aspects of the present embodiments.

FIG. 8 is a bottom view of an alternative ventilation window 800 that may be installed on the underside of an exterior elevated element of a building, according to various aspects of the present embodiments. The top view of the ventilation window 800 may be similar to the top view of the ventilation window 600 of FIG. 6A. The ventilation window 800 may be one of the ventilation windows 175 of FIG. 1B.

With reference to FIG. 8, the ventilation window 800 may include several ventilation openings 610, a hinge 615, and several gaps 650, which may be similar to the corresponding components of ventilation window 600 of FIGS. 6A-6B. The ventilation window 800 may include a frame 805. The frame 805 may include several railings 821-824. The depicted embodiment includes four railings 821-824. Other embodiments may include only two railings, for example either the two railings 821 and 822 or the two railings 823 and 824.

Figure 9:
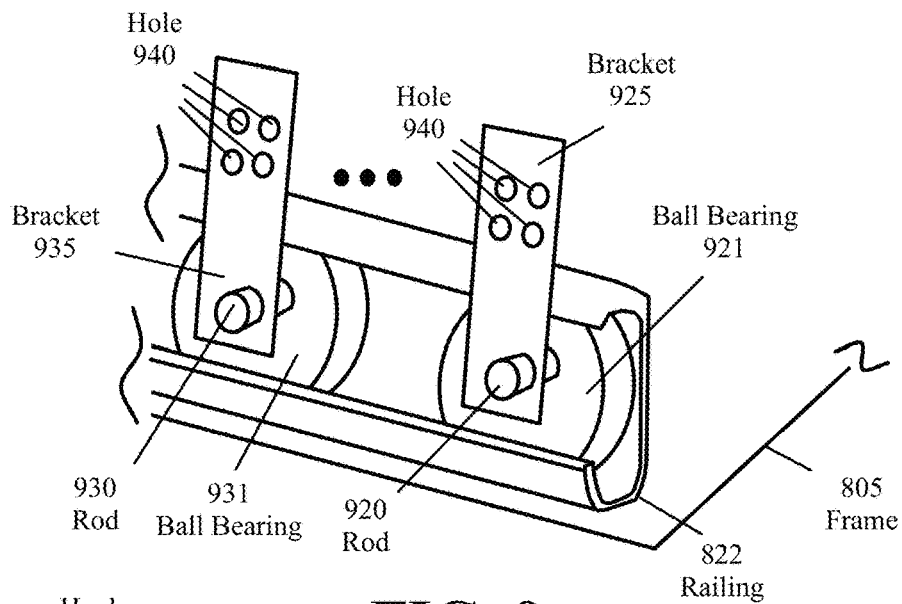
FIG. 9 illustrates a portion of a railing of FIG. 8, according to various aspects of the present disclosure.

FIG. 9 illustrates a portion of a railing of FIG. 8, according to various aspects of the present disclosure. With reference to FIG. 9, the railing may be, for example, the railing 822 of FIG. 8. As shown, several ball bearings 921 and 931 (only two ball bearings are shown in FIG. 9 for brevity) may move across the railing 822. Each ball bearing 921 and 931 may be connected to a corresponding rod 920 and 930, respectively. It should be noted that when the ball bearing 921 or 931 rotate, the corresponding rods 920 and 930, which are fixed to the center of the ball bearing do not rotate.

As shown, each rod 920 and 930 is connected to a corresponding bracket 925 and 935. The brackets may be, for example, metallic plates. Each bracket 925 and 935 may include one or more holes 940. In operation, when the ventilation window 800 (FIG. 8) is installed on the underside of an exterior elevated element, the ball bearings (e.g., the ball bearing 721) may be moved across the railing 822 until the corresponding bracket 925 is adjacent to a joist. The bracket may then be fixed to the joist by nails, bolts, screws, etc. The same operation may be repeated for other ball bearing by moving a ball bearings across the railings 822 until the corresponding bracket is adjacent to a joist. The bracket may then be fixed to the joist by nails, bolts, screws, etc. The same operation may be repeated for ball bearings on other railings (e.g., the railing 821 of FIG. 8) until the ventilation window is securely attached at several places to one or more joists.

In the depicted embodiment, the brackets 925 and 935 are attached to the rods 920-930 such that the surface of the brackets are parallel to the surface of the ball bearings 921-924. In other embodiments, the brackets 925 and 935 may be attached to the rods 920 and 930 such that the surface of the brackets are perpendicular to the surface of the ball bearings 921 and 931 (e.g., facing to the right or to the left, in the depicted orientation of FIG. 9). Some embodiments may provide two different groups of ball bearings and brackets, in one group, the surface of the brackets may be parallel to the surface of the ball bearings and in other group the surface of the brackets may be perpendicular to the surface of the ball bearings. An end user may then select the proper group of ball bearings and brackets for a particular installation job, depending on the desired orientation of the installed ventilation window and the orientation of the joists in the interior space of the exterior elevated elements.

Figure 10:
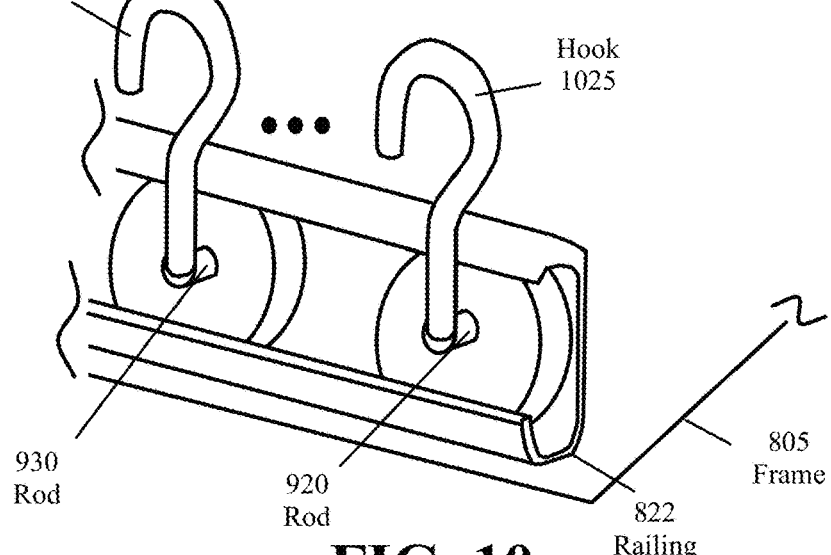
FIG. 10 illustrates a portion of a railing of FIG. 8, according to various aspects of the present disclosure.

FIG. 10 illustrates a portion of a railing of FIG. 8, according to various aspects of the present disclosure. With reference to FIG. 10, the railing 822, the ball bearings 921 and 931, and the rods 920 and 930 may be similar to the corresponding components of FIG. 9. The embodiment of FIG. 10 may include hooks 1025 and 1035 instead of the brackets 925 and 935 of FIG. 9. The hooks may be used to attach the ventilation window 800 (FIG. 8) to the joists of an exterior elevated element of a building.

It should be noted that the orientation of the hooks 1025 and 1035 with respect to the surface of the brackets may be different in different embodiments. In addition, some embodiments may provide different groups of ball bearings and hooks with different orientation for the hooks to allow an end user to select the proper ball bearings and hooks for a particular installation job, depending on the desired orientation of the installed ventilation window and the orientation of the joists in the interior space of the exterior elevated elements.

Figure 11:
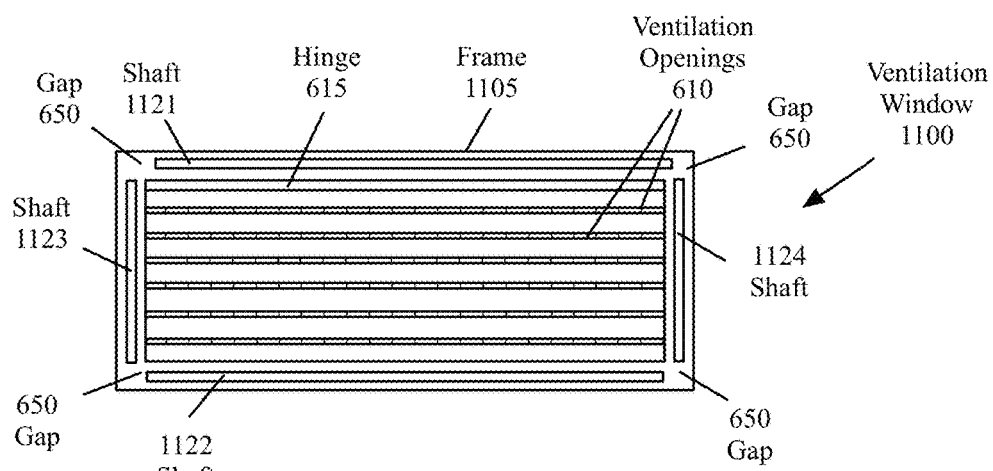
FIG. 11 is a bottom view of an alternative ventilation window that may be installed on the underside of an exterior elevated element of a building, according to various aspects of the present embodiments.

FIG. 11 is a bottom view of an alternative ventilation window 1100 that may be installed on the underside of an exterior elevated element of a building, according to various aspects of the present embodiments. The top view of the ventilation window 1100 may be similar to the top view of the ventilation window 600 of FIG. 6A. The ventilation window 1100 may be one of the ventilation windows 175 of FIG. 1B.

With reference to FIG. 11, the ventilation window 1100 may include several ventilation openings 610, a hinge 615, and several gaps 650, which may be similar to the corresponding components of ventilation window 600 of FIGS. 6A-6B. The ventilation window 1100 may include a frame 1105. The frame 1105 may include several shafts 1121-1124. The depicted embodiment includes four shafts 1121-1124. Other embodiments may include only two shafts, for example either the two shafts 1121 and 1122 or the two shafts 1123 and 1124.

Figure 12:
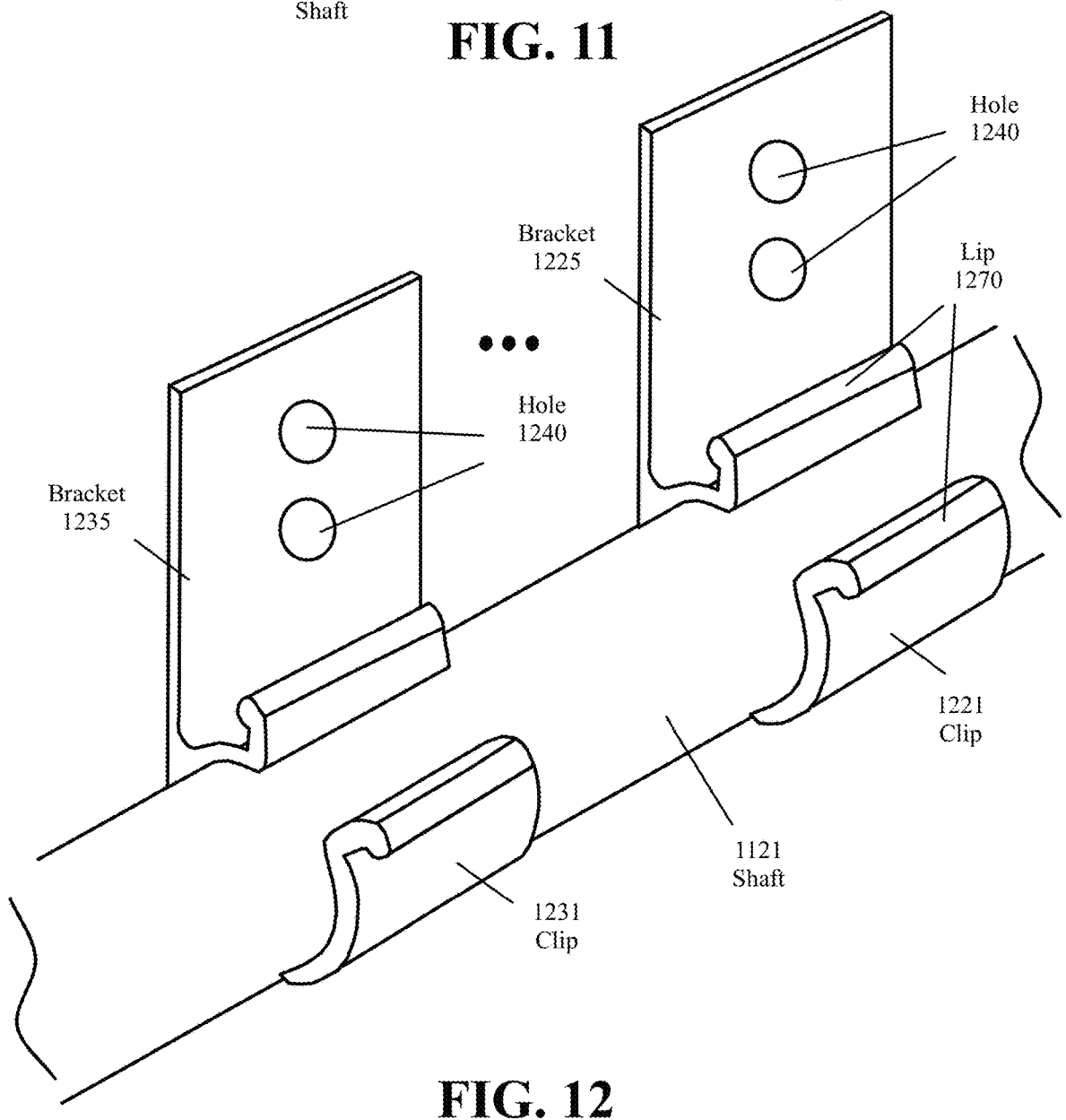
FIG. 12 illustrates a portion of a shaft of FIG. 11, according to various aspects of the present disclosure.

FIG. 12 illustrates a portion of a shaft of FIG. 11, according to various aspects of the present disclosure. With reference to FIG. 11, the shaft may be, for example, the shaft 1121 of FIG. 11. As shown, several clips 1221 and 1231 (only two clips are shown in FIG. 12 for brevity) may move across the shaft 1121. A clip may be detached from the shaft by applying a force to the two lips 1270 to move the lips apart. A clip may be attached to the shaft by placing the lips 1270 against the shaft and applying pressure to force the lips to move away from each other and hold the clip around the shaft. Each clip 1221 and 1231 may be connected to a corresponding bracket 1225 and 1235, respectively. The clips may be, for example, and without limitations, D-clips.

The brackets may be, for example, metallic plates. Each bracket 1225 and 1235 may include one or more holes 1240. In operation, when the ventilation window 1100 (FIG. 11) is installed on the underside of an exterior elevated element, the clips (e.g., the clip 1221) may be moved across the shaft 1121 until the corresponding bracket 1225 is adjacent to a joist. The bracket may then be fixed to the joist by nails, bolts, screws, etc. The same operation may be repeated for other clips by moving a clip across the shaft 1121 until the corresponding bracket is adjacent to a joist. The bracket may then be fixed to the joist by nails, bolts, screws, etc. The same operation may be repeated for clips on other shafts (e.g., the shaft 1122 of FIG. 11) until the ventilation window is securely attached at several places to one or more joists.

In the depicted embodiment, the brackets 1225 and 1235 are attached to the clips 1221 and 1231 such that the surface of the brackets are parallel to the length of the shaft 1121. In other embodiments, the brackets 1225 and 1235 may be attached to the clips 1221 and 1231 such that the surface of the brackets are perpendicular to the length of the shaft 1121.

Some embodiments may provide two different groups of clips and brackets. In one group, the surface of the brackets may be parallel to the length of the shaft and in other group the surface of the brackets may be perpendicular to the length of the shaft. An end user may then select the proper group of clips and brackets for a particular installation job, depending on the desired orientation of the installed ventilation window and the orientation of the joists in the interior space of the exterior elevated elements.

Figure 13:
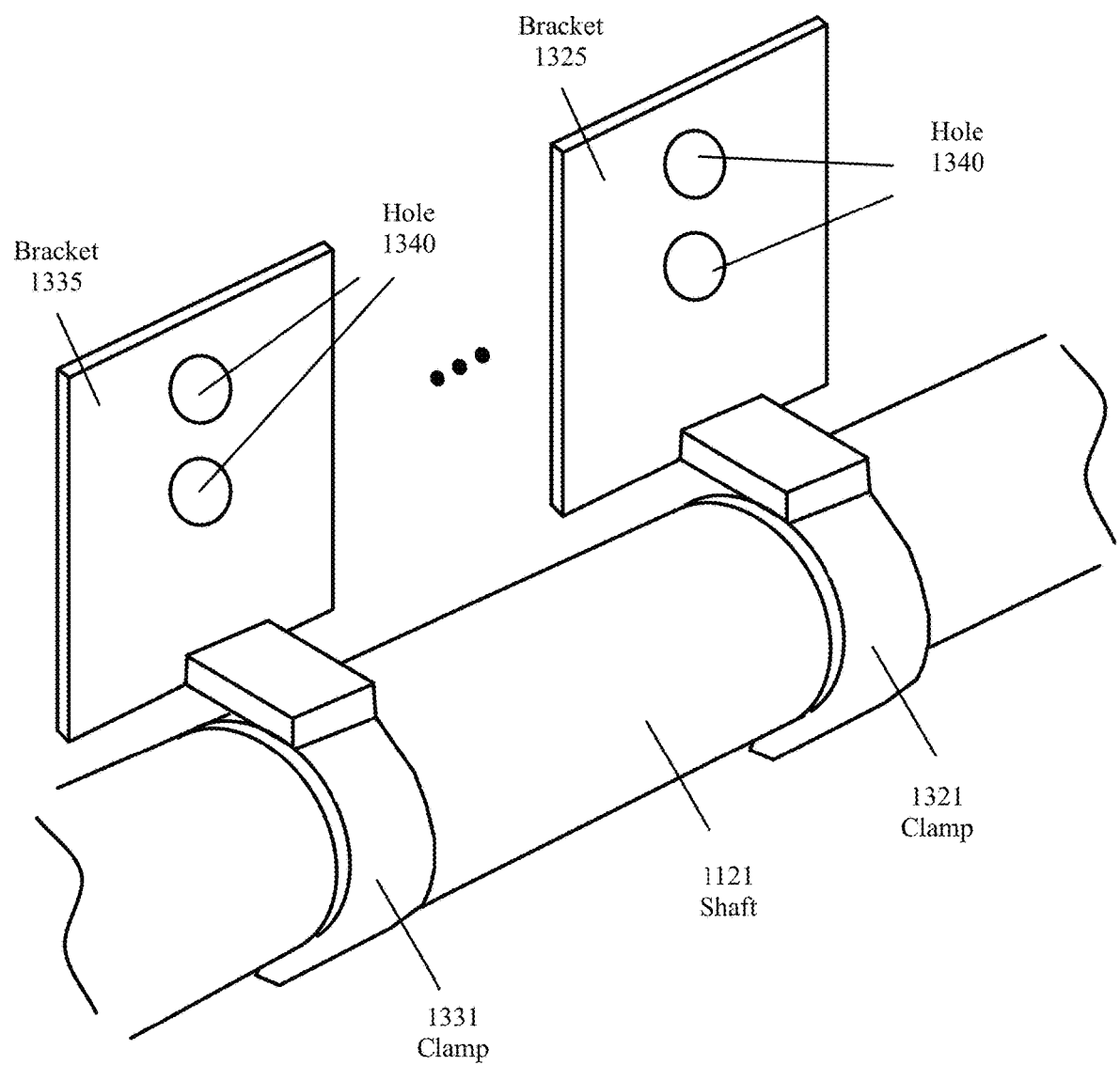
FIG. 13 illustrates a portion of a shaft of FIG. 11, according to various aspects of the present disclosure.

FIG. 13 illustrates a portion of a shaft of FIG. 11, according to various aspects of the present disclosure. With reference to FIG. 13, the shaft 1121 may be similar to the shaft 1121 of FIG. 12. The embodiment of FIG. 13 may include the clamps 1321 and 1331 instead of the clips 1221 and 1231 of FIG. 12. As shown, several clamps 1321 and 1331 (only two clamps are shown in FIG. 13 for brevity) may move across the shaft 1121. A clamp may be fastened around, or loosened from, the shaft by a screw or a bolt. Each clamp 1321 and 1331 may be connected to a corresponding bracket 1325 and 1335, respectively.

The brackets may be, for example, metallic plates. Each bracket 1325 and 1335 may include one or more holes 1340. In operation, when the ventilation window 1100 (FIG. 11) is installed on the underside of an exterior elevated element, the clamps (e.g., the clamp 1321) may be moved across the shaft 1121 until the corresponding bracket 1325 is adjacent to a joist. The bracket may then be fixed to the joist by nails, bolts, screws, etc. The same operation may be repeated for other clamps by moving a clamp across the shaft 1121 until the corresponding bracket is adjacent to a joist. The bracket may then be fixed to the joist by nails, bolts, screws, etc. The same operation may be repeated for clamps on other shafts (e.g., the shaft 1122 of FIG. 11) until the ventilation window is securely attached at several places to one or more joists.

In the depicted embodiment, the brackets 1325 and 1335 are attached to the clamps 1321 and 1331 such that the surface of the brackets are parallel to the length of the shaft 1121. In other embodiments, the brackets 1325 and 1335 may be attached to the clamps 1321 and 1331 such that the surface of the brackets are perpendicular to the length of the shaft 1121. Some embodiments may provide two different groups of clamps and brackets. In one group, the surface of the brackets may be parallel to the length of the shaft and in other group the surface of the brackets may be perpendicular to the length of the shaft. An end user may then select the proper group of clamps and brackets for a particular installation job, depending on the desired orientation of the installed ventilation window and the orientation of the joists in the interior space of the exterior elevated elements. The clamps may be placed around the shaft, for example, through the gaps 650 (FIG. 11).

Figure 14:
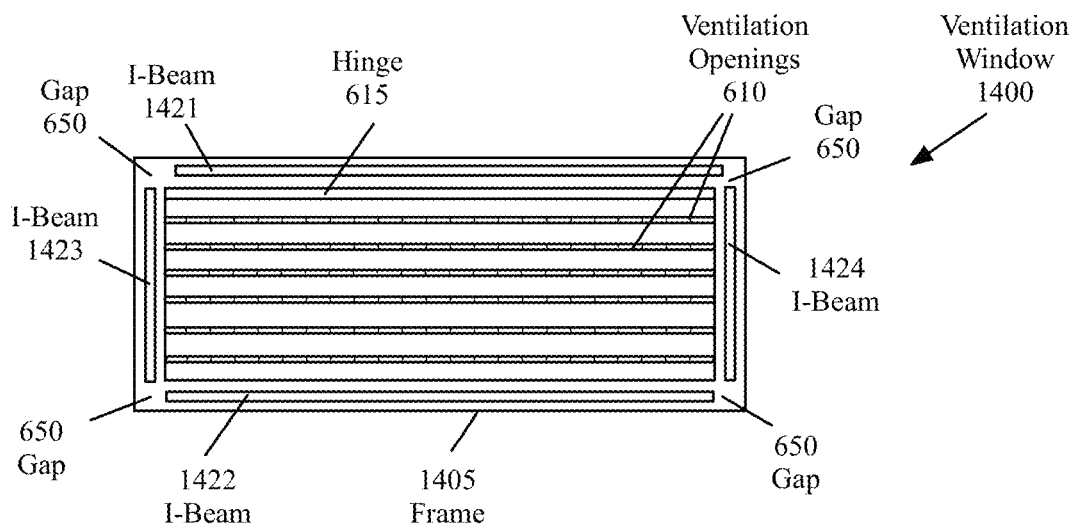
FIG. 14 is a bottom view of an alternative ventilation window that may be installed on the underside of an exterior elevated element of a building, according to various aspects of the present embodiments.

FIG. 14 is a bottom view of an alternative ventilation window 1400 that may be installed on the underside of an exterior elevated element of a building, according to various aspects of the present embodiments. The top view of the ventilation window 1400 may be similar to the top view of the ventilation window 600 of FIG. 6A. The ventilation window 1400 may be one of the ventilation windows 175 of FIG. 1B.

With reference to FIG. 14, the ventilation window 1400 may include several ventilation openings 610, a hinge 615, and several gaps 650, which may be similar to the corresponding components of ventilation window 600 of FIGS. 6A-6B. The ventilation window 1400 may include a frame 1405. The frame 1405 may include several I-beams 1421-1424. The depicted embodiment includes four I-beams 1421-1424. Other embodiments may include only two I-beams, for example either the two I-beams 1421 and 1422 or the two I-beams 1423 and 1424.

Figure 15:
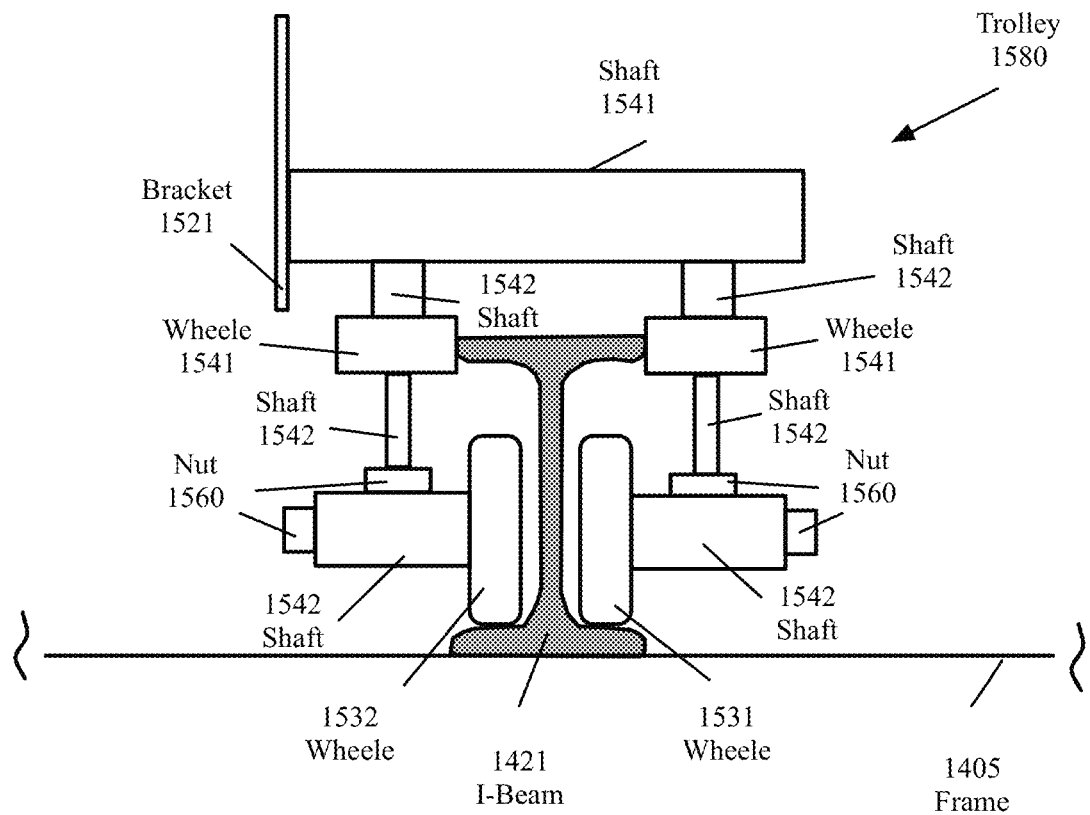
FIG. 15 illustrates a front view of an I-beam of FIG. 14, according to various aspects of the present disclosure.

FIG. 15 illustrates a front view of an I-beam of FIG. 14, according to various aspects of the present disclosure. With reference to FIG. 14, the I-beam may be, for example, the I-beam 1421 of FIG. 14. Several trolleys may move across the I-beam 1421 (only one I-beam 1580 is shown in the front view of FIG. 15). The trolley 1580 may include several wheels 1531-1532 and 1541-1542. As shown, the wheels 1531-1532 may rotate in a plane that is perpendicular to the rotation plane of the wheels 2541-1542. The trolley 1580 may include several shafts 1541-1542 and several nuts 1560 that connect different components of the trolley 1580 together. As the wheels 1531-1532 and 1541-1542 rotate in their respective rotation plane, the trolley 1580 moves along the I-beam. It should be noted that the trolley 1580 is configured such that shafts 1541-1542 do not rotate as the trolley 1580 moves along the I-beam.

As shown, the bracket 1531 is attached to the shaft 1541. The bracket 1521 may be similar to the brackets 725 and 735 of FIG. 7, the brackets 925 and 935 of FIG. 9, the brackets 1225 and 1235 of FIG. 12, or the brackets 1325 and 1335 of FIG. 13. The bracket 1521 may include one or more holes that are similar to the holes 740, 940, 1240, or 1740 of FIGS. 7, 9, 12, and 13, respectively. The hole(s) of the bracket 1521 is/are not shown in the front view of FIG. 15. The bracket may be, for example, metallic plates.

In operation, when the ventilation window 1400 (FIG. 14) is installed on the underside of an exterior elevated element, the trollies (e.g., the trolley 1580) may be moved across the I-beam 1421 until the bracket 1521 is adjacent to a joist. The bracket may then be fixed to the joist by nails, bolts, screws, etc. The same operation may be repeated for other trollies by moving a trolley across the I-beam 1421 until the corresponding bracket is adjacent to a joist. The bracket may then be fixed to the joist by nails, bolts, screws, etc. The same operation may be repeated for trollies on other I-beams (e.g., the I-beam 1422 of FIG. 14) until the ventilation window is securely attached at several places to one or more joists.

In the depicted embodiment, the bracket 1521 is attached to the trolley 1580 such that the surface of the bracket is parallel to the length of the I-beam 1421. In other embodiments, the bracket 1521 may be attached to the trolley 1580 such that the surface of the bracket is perpendicular to the length of the I-beam 1421. Some embodiments may provide two different groups of trollies and brackets. In one group, the surface of the brackets may be parallel to the length of the I-beam and in other group the surface of the brackets may be perpendicular to the length of the I-beam. An end user may then select the proper group of trollies and brackets for a particular installation job, depending on the desired orientation of the installed ventilation window and the orientation of the joists in the interior space of the exterior elevated elements. The trollies may be placed around the shaft, for example, through the gaps 650 (FIG. 14).

Referring back to FIG. 1B, any combination of the fans 140, the environmental sensors 155, and/or the ventilation windows 175 may be installed in an exterior elevated element 125. For example, depending on the size of the interior space of the exterior elevated element, the climate in the region where the exterior elevated element is located, the distance between the joists, and/or the number of separate compartments created by the joist in the interior space of the exterior elevated element, only one fan, multiple fans, only one environmental sensor, multiple environmental sensors, only one ventilation window, multiple ventilation windows, or any combination of one or more fans, one or more environmental sensors, or one or more ventilation windows may be installed in the exterior elevated element.

With further reference to FIG. 1B the fans 140 may start or stop based on a schedule (e.g., a period of being on and circulating the air followed by a period of being off). For example, the fans 140 may receive one or more signals from a controller 150 or from a hub 170 to turn on or off based on the schedule. In some embodiments, the fans may be controlled based on the value of the environmental parameter measurements received from the environmental sensor(s) 155.

Figure 16:
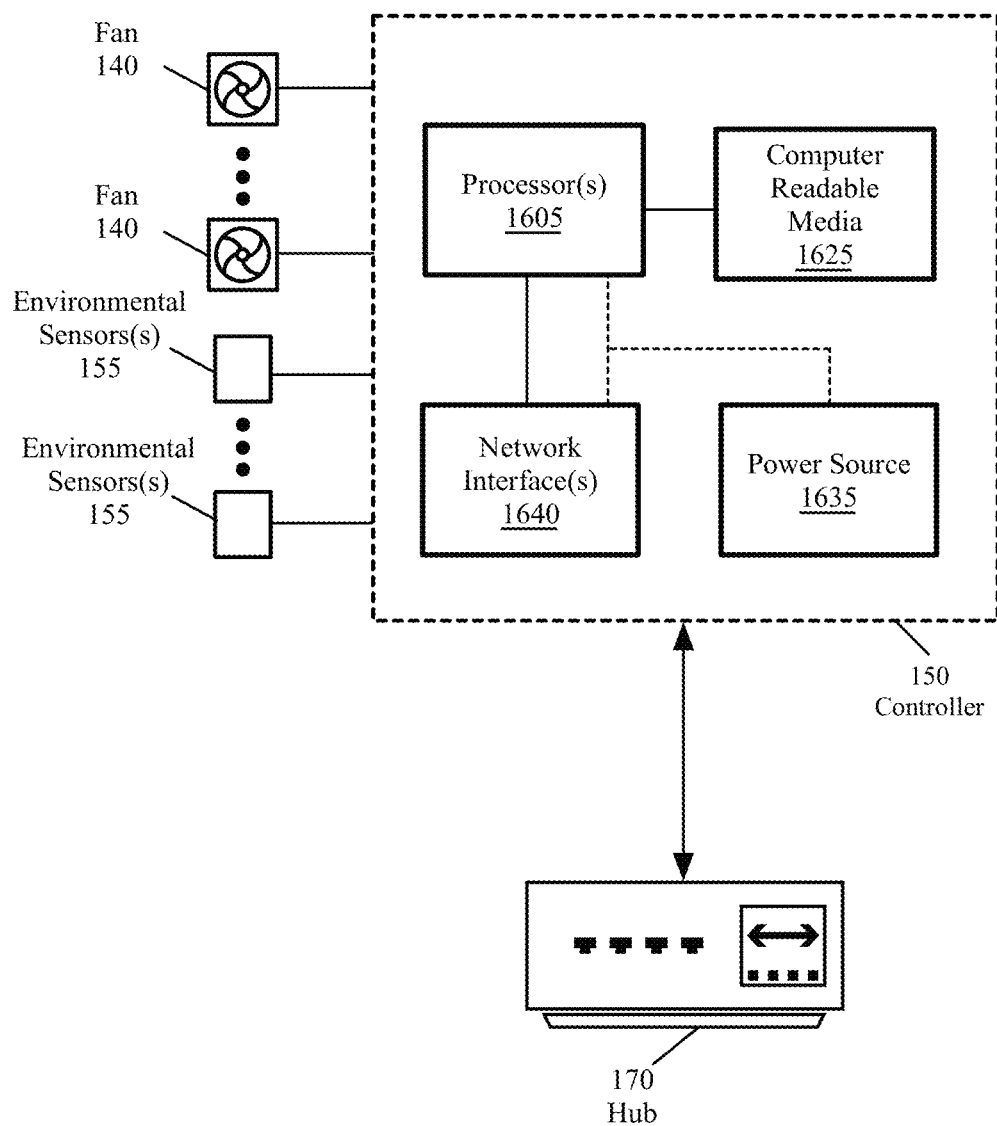
FIG. 16 is a functional diagram illustrating a controller that controls one or more fans and/or one or more environmental sensors of an exterior elevated element of a building, according to various aspects of the present disclosure.

FIG. 16 is a functional diagram illustrating a controller that controls one or more fans and/or one or more environmental sensors of an exterior elevated element of a building, according to various aspects of the present disclosure. With reference to FIG. 16, the controller 150 may be any of the controllers 150 of FIG. 1B.

The controller 150 may include one or more processors 1605, one or more computer readable media 1625, one or more network interfaces 1640, and a power source 1635. The controller 150 may be communicatively coupled (e.g., by wires or through the network interface 1640) to one or more fans 140 and/or one or more environmental sensors 155. It should be noted that, although several fans 140 and several environmental sensors are shown in FIG. 16, any number of one or more fans and/or any number of one or more environmental sensors may be controlled by a controller, such as the controller 150.

The processor(s) 1605 may receive environmental measurement parameters from the environmental sensor(s) 155. The processor(s) 1605 may store the environmental measurement parameters in the computer readable media 1625 and/or may send the environmental measurement parameters to the hub 170 through the network interface(s) 1640.

The power source 1635 may include a power adapter that may connect to an AC outlet. The network interface(s) 1640 may be one or more wireless (e.g., and without limitations, Wi-Fi or Bluetooth) transceivers to provide wireless connectivity with an external electronic device. In addition to, or in lieu of the wireless transceivers, the network interface(s) 1640 may include wired connectivity to the hub 170.

The processor(s) 1605 may control the fan(s) 140. For example, the processor(s) 1605, in some embodiments, may turn the fans 140 on or off based on a schedule. The processor(s) 1605 may send one or more signals to the fans 140 to turn on the fans 140 for a first time period. The processor(s) 1605 may send one or more signals to the fans 140 to turn off the fans 140 for a second time period or off based on the schedule. The processor(s) 1605 may repeat turning the fan(s) 140 on or off.

In some embodiments, processor(s) 1605 may control the fans 140 based on the value of the environmental parameter measurements received from the environmental sensor(s) 155. The processor(s) 1605 may compare an environmental parameter measurement with a corresponding threshold and if the environmental parameter measurement exceeds the threshold (e.g., the humidity or the moisture is more than a threshold) for a period of time (e.g., several hours, several days, etc.), the processor(s) 1605 may send one or more signals to the fan(s) 140 to turn the fan(s) 140 on. The processor(s) 1605 may send one or more signals to the fan(s) 140 to turn the fans 140 off when the environmental parameter measurements become less than or equal to the corresponding thresholds. The processor(s) 1605 may send a message to the hub 170 whenever a fan 140 is turned on or off.

Figure 17:
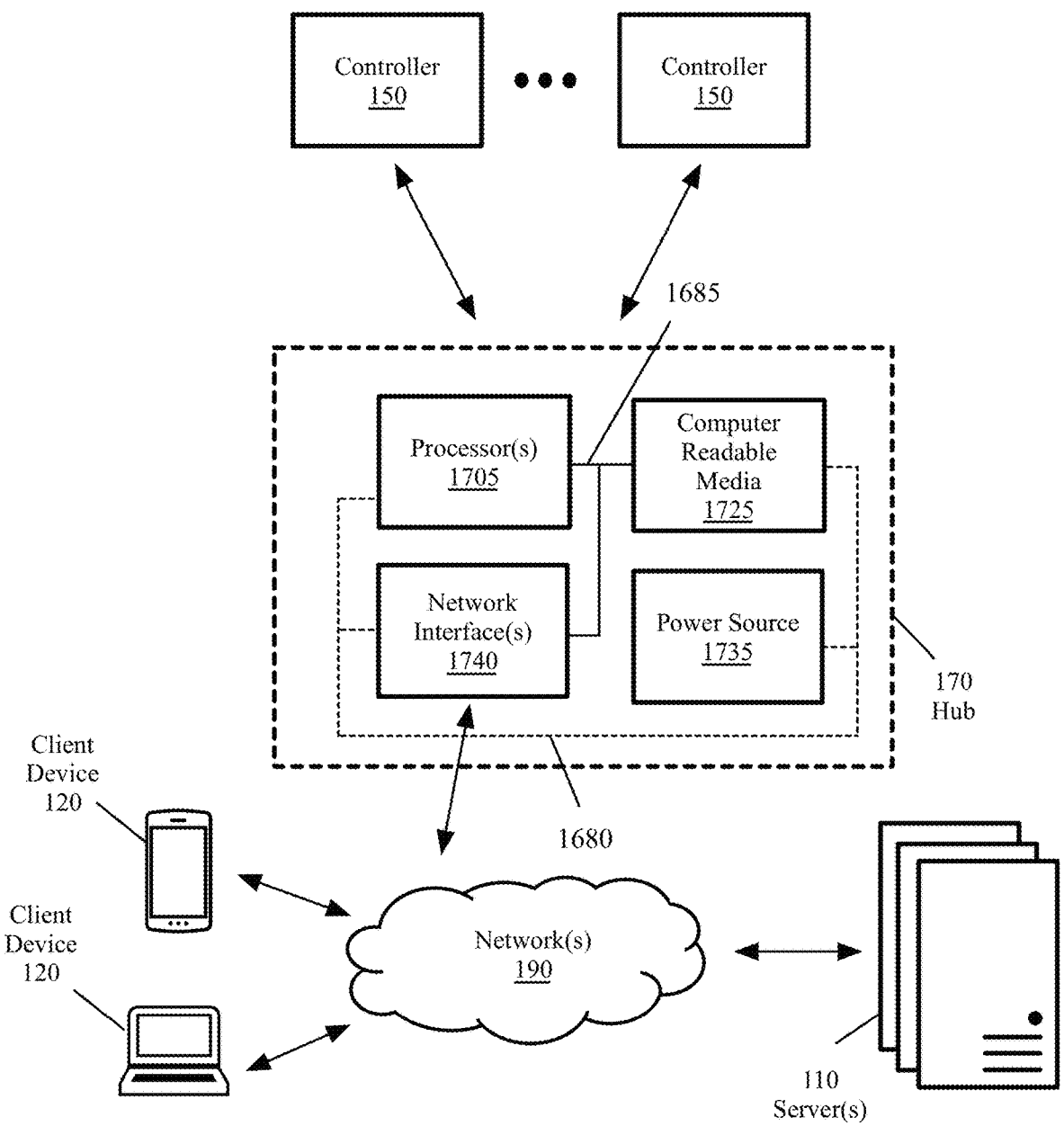
FIG. 17 is a functional diagram illustrating a hub that is used to communicate with one or more controllers associated with the exterior elevated elements of a building, according to various aspects of the present disclosure.

FIG. 17 is a functional diagram illustrating a hub that is used to communicate with one or more controllers associated with the exterior elevated elements of a building, according to various aspects of the present disclosure. The hub 170 may include one or more processors 1705, one or more computer readable media 1725, one or more network interfaces 1740, and a power source 1735. The hub 170 may be communicatively coupled (e.g., by wires or through the network interface(s) 1740) to one or more controllers 150. The controller(s) 150 may be similar to the controller 150 of FIG. 16 that may be used to control one or more environmental sensors 155 and/or one or more fans 140.

The processor(s) 1705 may receive environmental measurement parameters from the controller(s) 150. The processor(s) 1705 may store the environmental measurement parameters in the computer readable media 1725 and/or may send the environmental measurement parameters to one or more external electronic devices, such as, the client devices 120 and/or the server(s) 110 through the network(s) 190.

The power source 1735 may include a power adapter that may connect to an AC outlet. The network interface(s) 1740 may be one or more wireless (e.g., and without limitations, Wi-Fi or Bluetooth) transceivers to provide wireless connectivity with an external electronic devices (e.g., the controller(s) 150, the client devices 120 and/or the server(s) 110). In addition to, or in lieu of the wireless transceivers, the network interface(s) 1740 may include wired connectivity to the controller(s) 150.

The processor(s) 1705 may receive the status (e.g., on, off, not responding, etc.) of the fan(s) 140 (FIG. 16) from the controller(s) 150. In some embodiments, processor(s) 1705 may the control the operations of the fan(s) 140. In some of these embodiments, the processor(s) 1705 may control the fan(s) 140 through their corresponding controller(s) 150. In other embodiments, the processor(s) 1705 may directly control the fan(s) 140. In these embodiments, the controller(s) 150 do not communicate with the fan(s) 140 (e.g., the controller(s) 150 only communicate with the environmental sensor(s) 155).

For example, the processor(s) 1705, in some embodiments, may turn the fans 140 on or off based on a schedule. The processor(s) 1705 may send one or more signals to the fans 140 (either directly or through the corresponding controller(s) 150) to turn on the fans 140 for a first time period. The processor(s) 1705 may send one or more signals to the fans 140 (either directly or through the corresponding controller(s) 150) to turn off the fans 140 for a second time period or off based on the schedule. The processor(s) 1705 may repeat turning the fan(s) 140 on or off.

In some embodiments, processor(s) 1705 may control the fans 140 based on the value of the environmental parameter measurements received from the environmental sensor(s) 155. In some embodiments, the processor(s) 1705 may compare an environmental parameter measurement received from an environmental sensor with a corresponding threshold and if the environmental parameter measurement exceeds the threshold (e.g., the humidity or the moisture is more than a threshold) for a period of time (e.g., several hours, several days, etc.), the processor(s) 1705 may send one or more signals to the fan(s) 140 (either directly or through a corresponding controller 150) to turn the fans 140 on. The processor(s) 1705 may send one or more signals to the fan(s) 140 (either directly or through a corresponding controller 150) to turn the fan(s) 140 off when the environmental parameter measurement becomes less than or equal to the corresponding thresholds.

In some embodiments, the processor 1605 of a controller 150 and/or the processor 1705 of a hub 170 may save the current status of a fan 140 (e.g., on or off) in computer readable medium. When a fan does not respond to an on or off signal, the processor 1605 of a controller 150 and/or the processor 1705 of a hub 170 may set the status of the fan 140 to failed and may send an alert message to one or more external devices, such as the client devices 120 and/or the server(s) 110 of FIG. 1B.

Figure 18:
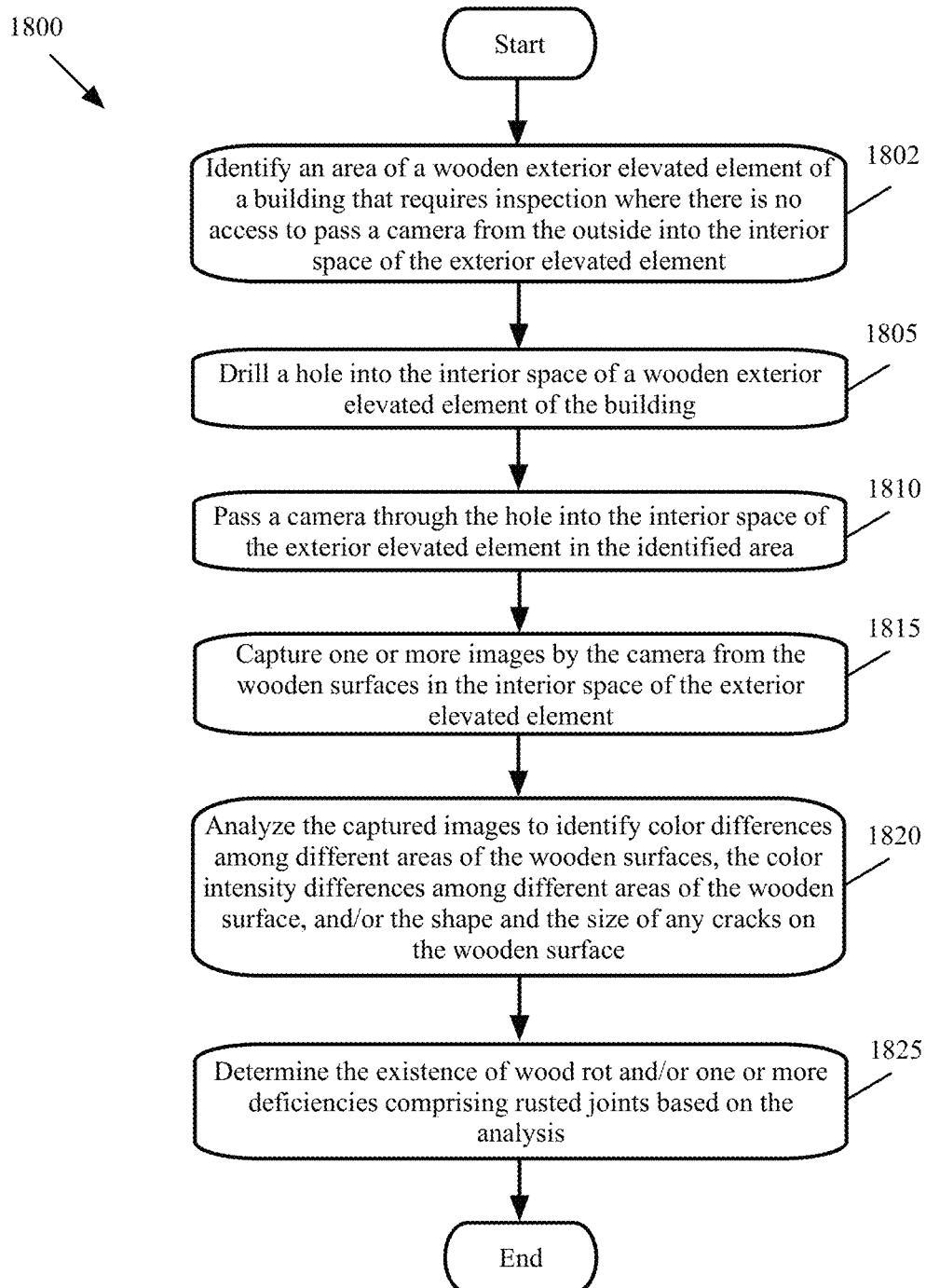
FIG. 18 is a flowchart illustrating an example process for inspecting the interior space of a wooden exterior elevated element of a building, according to various aspects of the present disclosure.

FIG. 18 is a flowchart illustrating an example process 1800 for inspecting the interior space of an exterior elevated element of a building, according to various aspects of the present disclosure. The process 1800, in some of the present embodiments, may be performed during inspection of an exterior elevated element of a building.

With reference to FIG. 18, an area of a wooden exterior elevated element of a building may be identified (at block 1802) that requires inspection where there is no access to pass a camera from the outside into the interior space of the exterior elevated element. A hole may be drilled (at block 1805) into the interior space of a wooden exterior elevated element. For example, a hole may be drilled into the interior of the exterior elevated element as described above with reference to FIGS. 1A-1B and 3. A camera may be passed (at block 1810) through the hole into the interior space of the exterior elevated element. For example, a snake camera or a camera installed on a crawler robot may be passed into the interior space of the exterior elevated element as described above with reference to FIGS. 4A-4B and 5A-5B.

One or more images may be captured (at block 1815) by the camera from the interior space of the exterior elevated element. For example, the controller 152 of the snake camera 150 may send one or more signals to the camera 410 to capture video images or still images of the interior space, as described above with reference to FIGS. 4A-4B. As another example, the controller 162 of the crawler robot 160 may send one or more signals to the camera 510 to capture video images or still images of the interior space, as described above with reference to FIGS. 5A-5B. The camera, in some embodiments, may take video and/or still images. The camera may take visible light and/or infrared light images.

The captured images may then be analyzed (at block 1820) to identify one or more of color differences of the wooden surfaces, color intensity differences of the wooden surfaces, and the shape and the size of any cracks on the wooden surfaces. For example, the processor of an electronic device, such as the client device 153 (FIG. 1A), the controller 162 of the crawler robot 160, or a sever 110 may analyze the images, as described above with reference to FIG. 1A. The existence of wood rot in the interior space of the exterior elevated element may then be determined (at block 1825) based on the analysis.

In addition to, or in lieu of finding wood rot in the interior space of the exterior elevated element, analyzing the images may identify rust on the metallic surfaces of components, such as nuts, bolts, brackets, nails, in the interior space of the exterior elevated element. For example, the rusted metal may have a different color and/or different color intensity than the metal that is not rusted. The hole in some embodiments (e.g., the embodiments described below with reference to FIG. 19) may be permanently sealed. For example, and without limitations, the hole may be filled with spackle paste, which may be made of gypsum powder and other binders. Once the spackle paste is applied and dries, it permanently seals (or paths) the hole. In other embodiments, the hole may be covered by a ventilation window (e.g., as described above with reference to FIGS. 6A-15), or may be plugged by a cap or plug that may be, for example, made of rubber, plastic, silicone, etc. The process 1800 may then end.

In some embodiments, the process 1800 may also pass one or more environmental sensors, such as, for example, a humidity sensor, a moisture sensor, a temperature sensor, etc., through the hole after the hole is drilled. The environmental sensors may, for example, be attached to the snake camera (e.g., as shown in FIG. 4A), connected to a crawler robot (e.g., as shown in FIG. 5), etc. The environmental sensors may make measurements of parameters, such as humidity, moisture, and/or temperature, which may be used to determine whether the wood in the interior space of the balcony has dry rot and may need treatment.

Figure 19:
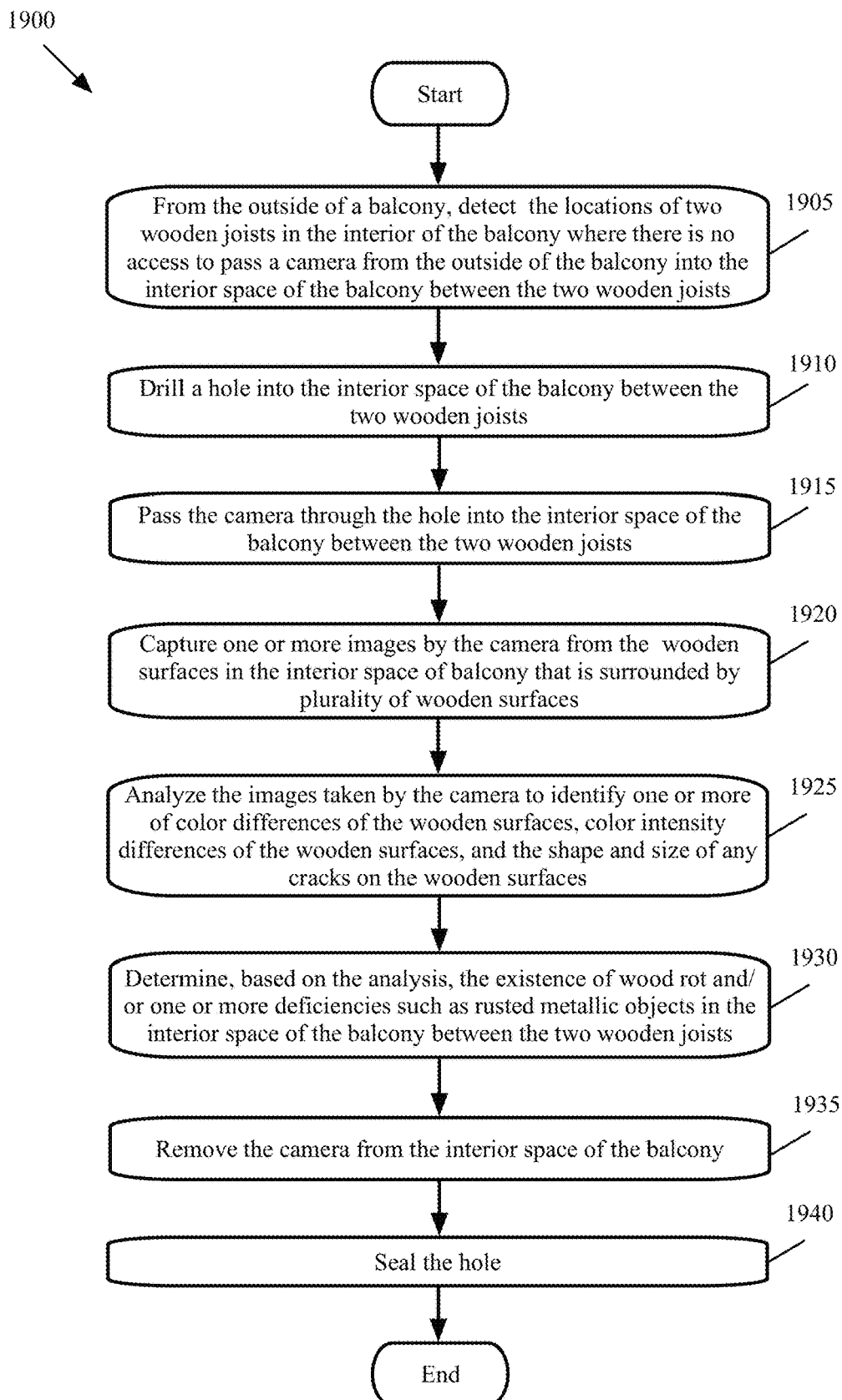
FIG. 19 is a flowchart illustrating an example process for drilling a hole into the area between two interior joists of a balcony to provide access to pass a camera to inspect the area between the two joists, according to various aspects of the present disclosure.

FIG. 19 is a flowchart illustrating an example process 1900 for drilling a hole into the area between two interior joists of a balcony to provide access to pass a camera to inspect the area between the two joists, according to various aspects of the present disclosure. The process 1900, in some of the present embodiments, may be performed during the inspection of an existing balcony.

From the outside of a balcony, the locations of two wooden joists in the interior of the balcony may be detected (at block 1905) where there is no access to pass a camera from the outside of the balcony into the interior space of the balcony between the two wooden joists. For example, an electronic stud finder may be used in some embodiments to find the location of two joists in the interior of the balcony.

Figure 20:
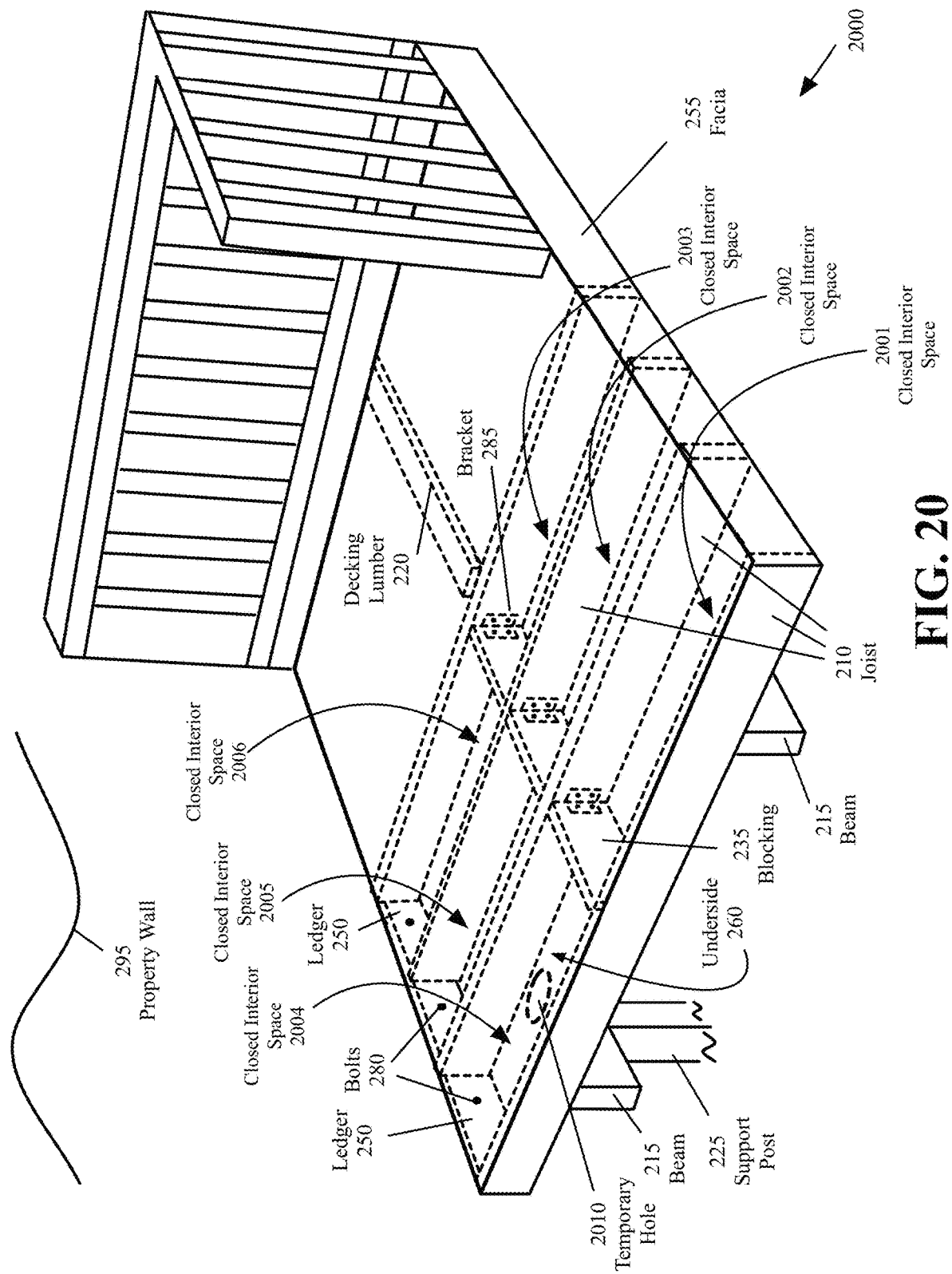
FIG. 20 shows the closed areas that may be formed between the joists in the interior of a balcony where a hole has to be drilled to pass a camera inside, according to various aspects of the present disclosure.

FIG. 20 shows the closed areas that may be formed between the joists in the interior of a balcony where a hole has to be drilled to pass a camera inside, according to various aspects of the present disclosure. The balcony 2000 is shown in the same perspective view as the balcony 200 of FIG. 2, except that in FIG. 2 the top of the balcony 200 is removed to show some of the inside components.

As shown in FIG. 20, several closed interior spaces, such as the closed spaces 2001-2006 may exist in the interior of the balcony 2000. For clarity, not every interior component of the balcony is shown in the figure. Depending on the location of the closed interior spaces 2001-2006, the spaces may be surrounded by several different pieces of wood, such as joists, ledgers, blockings, etc. The upper side of each closed space may be covered by decking lumbers 220 (only one decking lumber is shown for clarity), plywood, waterproofing coating, tiles, and/or paint, etc. The bottom side of each closed space may be covered, for example, by lath wire (also referred to as chicken wire) and may be covered by stucco. The spaces 2001-2006 may also include metallic components, such as bolts 280, brackets 285, nuts, nails, etc.

Referring back to FIG. 19, a hole may be drilled (at block 1910) into the interior space of the balcony between the two wooden joists. For example, as shown in FIG. 20, a temporary hole 2010 may be drilled from the outside of the balcony into the closed interior space 2004 of the balcony. The hole may be drilled, for example, by a bi-metal hole saw, a drill, and/or a hammer, etc. The hole may be made just wide enough to allow a snake camera or a crawler robot to pass through. Drilling a hole that is as small as possible to allow a snake camera or a crawler robot to pass through provides the advantage of making patching the hole easier and the place where the hole was become less visible to the eye after patching. In some embodiments, the hole may be made from the underside 260 of the balcony to prevent any damage to the paint, tiles, waterproof coating, decking lumber, etc., that may be on the upper surface of the balcony.

A camera may be passed (at block 1915) through the hole into the interior space of the balcony between the two wooden joists. The camera may be, for example, similar to the camera 410 that is part of a snake camera 150, as shown in FIGS. 4A-4B. The camera may be, for example, similar to the camera 510 installed on a crawler robot 160, as shown in FIGS. 5A-5B, etc. The snake camera, or the crawler robot, may include one or more environmental sensors 155, as described above with reference to FIGS. 4A-4 and 5A-5B.

One or more images may be captured (at block 1920) by the camera from the wooden surfaces in the interior space of balcony that is surrounded by multiple wooden surfaces. The images may also show metallic components, such as nuts, bolts, nails, brackets, etc. The camera, in some embodiments, may take video and/or still images. The camera may take visible light and/or infrared light images.

The images taken by the camera may be analyzed (at block 1925) to identify one or more of color differences of the wooden surfaces, color intensity differences of the wooden surfaces, and the shape and the size of any cracks on the wooden surfaces. The existence of wood rot may be determined (at block 1930), based on the analysis, in the interior space of the balcony between the two wooden joists. In addition to, or in lieu of finding wood rot in the interior space of the exterior elevated element, analyzing the images may identify rust in the metallic components, such as nuts, bolts, brackets, nails, in the in the interior space of the exterior elevated element. For example, the rusted metal may have a different color and/or different color intensity than the metal that is not rusted.

The camera may be removed (at block 1935) from the interior space of the balcony. The hole may be sealed (at block 1940). The process 1900 may then end. The hole, in some embodiments, may be permanently sealed. For example, and without limitations, the hole may be filled with spackle paste, which may be made of gypsum powder and other binders. Once the spackle paste is applied and dries, it permanently seals (or paths) the hole. Permanently sealing the hole may provide the technical advantage of restoring the balcony to the original condition prior to drilling the hole and may ensure not moisture may get into the interior space of the balcony. In other embodiments, the hole may be covered by a ventilation window (e.g., as described above with reference to FIGS. 6A-15), or may be plugged by a cap or plug that may be, for example, made of rubber, plastic, silicone, etc.

In some embodiments, the process 1900 may also pass one or more environmental sensors, such as, for example, a humidity sensor, a moisture sensor, a temperature sensor, etc., may be passed through the hole after the hole is drilled. The environmental sensors may, for example, be attached to the snake camera (e.g., as shown in FIG. 4A), connected to a crawler robot (e.g., as shown in FIG. 5), or etc. The environmental sensors may make measurements of parameters, such as humidity, moisture, and/or temperature, which may be used to determine whether the wood in the interior space of the balcony may need treatment.

With reference to the process 1800 of FIG. 18 and the process 1900 of FIG. 19, the camera be an infrared camera. Some embodiments may pass two cameras through the hole into the interior space of the structure, one camera for taking infrared images and another camera for taking visual light images. For example, both cameras may be installed on the same or on a different snake camera or crawler robot. The images taken by the infrared camera provide the advantage of detecting temperature differences on the wood surfaces, which may indicate wet areas, or areas that have dry rot. Some embodiments may combine the information collected from analyzing the visible light images, the infrared images, and/or the environmental sensor(s) readings to determine the existence of dry rot and/or excess moisture in the interior spaces of balconies and other exterior elevated elements of a building. For example, the areas that are identified by multiple methods as having dry rot may be identified as the area where there is a high confidence that are affected by dry rot.

Figure 21:
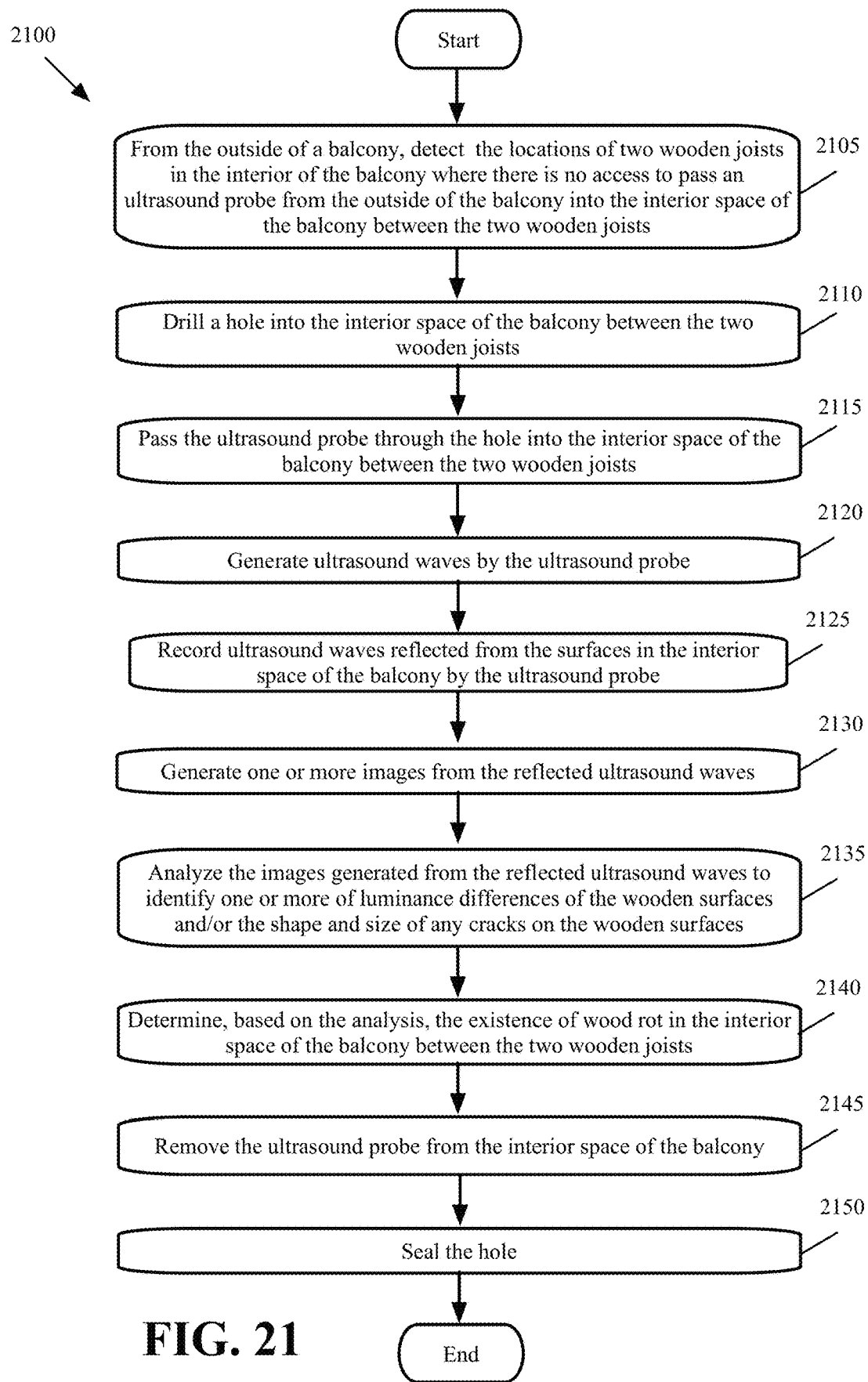
FIG. 21 is a flowchart illustrating an example process for drilling a hole into the area between two interior joists of a balcony to provide access to pass an ultrasound probe to inspect the area between the two joists, according to various aspects of the present disclosure.

FIG. 21 is a flowchart illustrating an example process 2100 for drilling a hole into the area between two interior joists of a balcony to provide access to pass an ultrasound probe to inspect the area between the two joists, according to various aspects of the present disclosure. The process 2100, in some of the present embodiments, may be performed during the inspection of an existing balcony.

From the outside of a balcony, the locations of two wooden joists in the interior of the balcony may be detected (at block 2105) where there is no access to pass an ultrasound probe from the outside of the balcony into the interior space of the balcony between the two wooden joists. For example, an electronic stud finder may be used in some embodiments to find the location of two joists in the interior of the balcony.

A hole may be drilled (at block 2110) into the interior space of the balcony between the two wooden joists. For example, as shown in FIG. 20, a temporary hole 2010 may be drilled from the outside of the balcony into the closed interior space 2004 of the balcony. The hole may be drilled, for example, by a bi-metal hole saw, a drill, and/or a hammer, etc. The hole may be made just wide enough to allow a small ultrasound probe that is installed on a snake cable or a crawler robot to pass through.

Drilling a hole that is as small as possible to allow the ultrasound probe over a snake cable or a crawler to pass through provides the advantage of making patching the hole easier and the place where the hole was become less visible to the eye after patching. In some embodiments, the hole may be made from the underside 260 of the balcony to prevent any damage to the paint, tiles, waterproof coating, decking lumber, etc., that may be on the upper surface of the balcony. The ultrasound probe may be passed (at block 2115) through the hole into the interior space of the balcony between the two wooden joists.

Figure 22A:
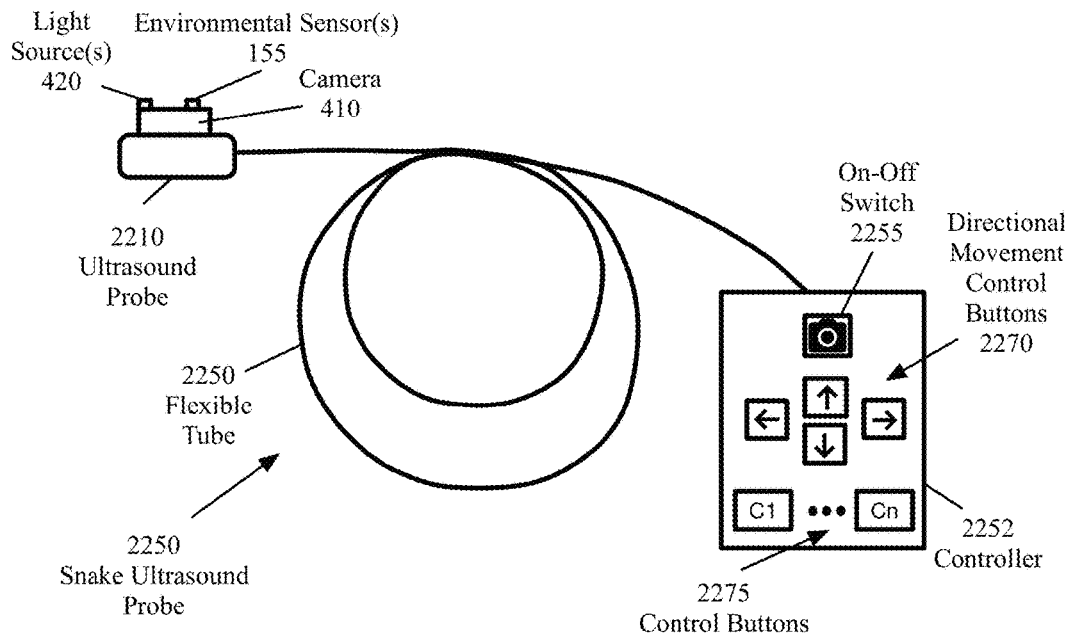
FIG. 22A is a schematic front view of a custom-made snake ultrasound probe and the associated controller, according to different aspects of the present disclosure.
Figure 22B:
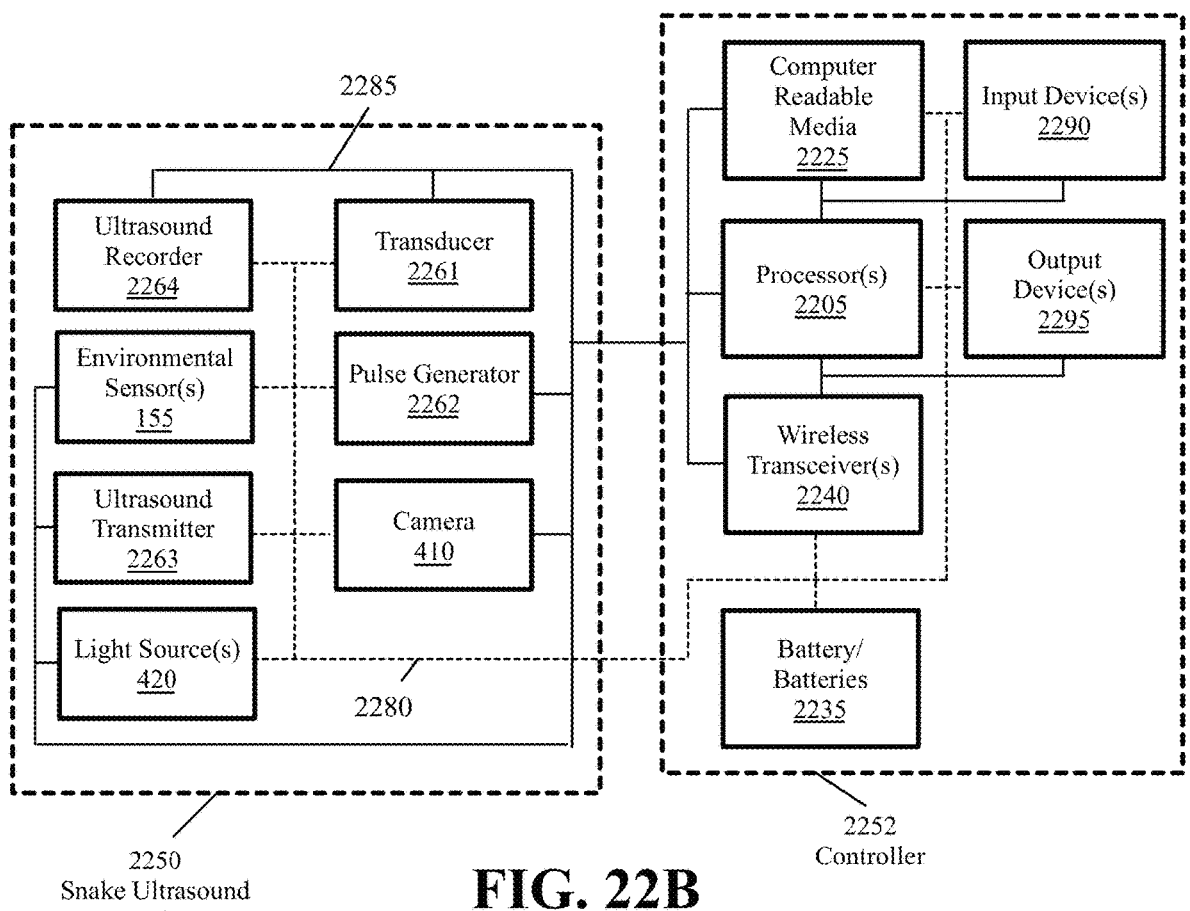
FIG. 22B is a functional block diagram of the components of the custom-made snake ultrasound probe of FIG. 22A, according to different aspects of the present disclosure.

FIG. 22A is a schematic front view of a custom-made snake ultrasound probe and the associated controller, according to different aspects of the present disclosure. FIG. 22B is a functional block diagram of the components of the custom-made snake ultrasound probe of FIG. 22A, according to different aspects of the present disclosure. With reference to FIGS. 22A-22B, the snake ultrasound probe 2250 may include an ultrasound probe 2210, a flexible tube 2250, and a controller 2252. The ultrasound probe 2210 and the controller 2252 are also referred to as an ultrasound scanner. The ultrasound probe 2210 may have a small form factor (e.g., approximately 1"×1"×5" or less). The ultrasound probe 2210 may be mounted at the end of the flexible tube 2250. The ultrasound probe 2250 may generate ultrasound waves and may record the ultrasound waves that are reflected from different surfaces. The snake ultrasound probe 2250 may be a miniaturized device to minimize the impact for drilling a hole into the interior of the balcony.

Some of the snake ultrasound probes of the present embodiments may include one or more environmental sensors 155. The environmental sensors 155 may measure the environmental conditions of the interior space of an exterior elevated element, such as a balcony. The environmental sensors 155 may include, for example, and without limitations, a humidity sensor, a moisture sensor, and/or a temperature sensor, which were described above. The snake ultrasound probe 2250, in some embodiments, may include a camera 410 and one or more light sources 420, which may function similar to the camera 410 and light source(s) 420 of FIGS. 4A-4B. The camera 410 and light source(s) 420 may be used to capture images of the interior of an exterior elevated element to detect wood rot on wood surfaces and rust on metallic surfaces, as described above. In addition to, or in lieu of being used for rot and rust detection, the camera 410 and light source(s) 420 may be used to provide images to allow an operator to navigate the snake ultrasound probe in the interior space of an exterior elevated element.

With further reference to FIGS. 22A-22B, different components of the snake ultrasound probe 2250 may be connected to each other by several wires 2285, a portion of which may run through the flexible tube 2250. The controller 2252 may be a hand-held controller. The controller 2252 may include one or more processors 2205, one or more computer readable media 2225, one or more wireless (e.g., and without limitations, Wi-Fi or Bluetooth) transceivers 2240, one or more batteries 2235, one or more input devices 2290, and/or one or more output device(s) 2295. The processor(s) 2205 may control the operations of the ultrasound probe 2210 through the on-off switch 2255, the directional movement control buttons 2270, and/or the control buttons 2275.

The battery (or batteries) 2235 may be rechargeable and/or replaceable and may provide power to different components of the controller 2252 and the snake ultrasound probe 2250 through one or more wires 2280. The wireless transceivers 2240 may provide wireless connectivity with one or more external electronic devices.

The input device(s) 2290 may include directional movement control buttons 2270 (e.g., to move the direction of the ultrasound waves) and the control buttons 2275 (e.g., to focus the ultrasound beam, to save ultrasound images, to review the ultrasound images, etc.). The output device(s) 2295 may include a display and one or more light-emitting diodes (LEDs) to show on-off or other status.

The snake ultrasound probe 2250 may include a transducer 2261 for generating ultrasound waves, a pulse generator 2262 for generating a carrier pulse wave, an ultrasound transmitter 2263 for transmitting ultrasound waves, an ultrasound recorder 2264 for recording the ultrasound waves echoes, the camera 410, the light source(s) 420, and the environmental sensor(s) 155.

The controller 2252 may be configured to wirelessly communicate to a client device (such as the client device 153 of FIG. 1A), for example, through an application program (app) that may be downloaded into the client device 153. The processor(s) 2205 (FIG. 4B) may receive images (e.g., video images and/or still images) captured by the camera 410 and may send the images to the client device 153 (FIG. 1A). The processor(s) 2205 may receive environmental parameters, such as humidity, moisture, and temperature, measured by the environmental sensor(s) 155 and may send the parameters to the client device 153. The processor(s) 2205 may receive the ultrasound echo recordings from the ultrasound probe 2210 and may generate visible images from the ultrasound recordings. The processor(s) 2205 may analyze the images generated from the reflected ultrasound waves to identify wood rot on the wood surfaces and/or may display the images on a display of the controller 2252. Some embodiments may combine the information collected from analyzing the visible light images, the infrared images, the images generated from the reflected ultrasound waves, and/or the environmental sensor(s) readings to determine the existence of dry rot and/or excess moisture in the interior spaces of balconies and other exterior elevated elements of a building. For example, the areas that are identified by multiple methods as having dry rot may be identified as the area where there is a high confidence that are affected by dry rot.

In addition to, or in lieu of, the buttons 2270 and 2275, the app on the client device 153 may provide similar controls. The client device 153 app may allow the images generated from the reflected ultrasound waves and/or the images taken by the camera 410 to be viewed on a display of the client device 153, to be stored in the computer readable media of the client device 153, and/or to be transmitted to external electronic devices, such as the server(s) 110 of FIG. 1A, through one or more networks 190.

Figure 23A:
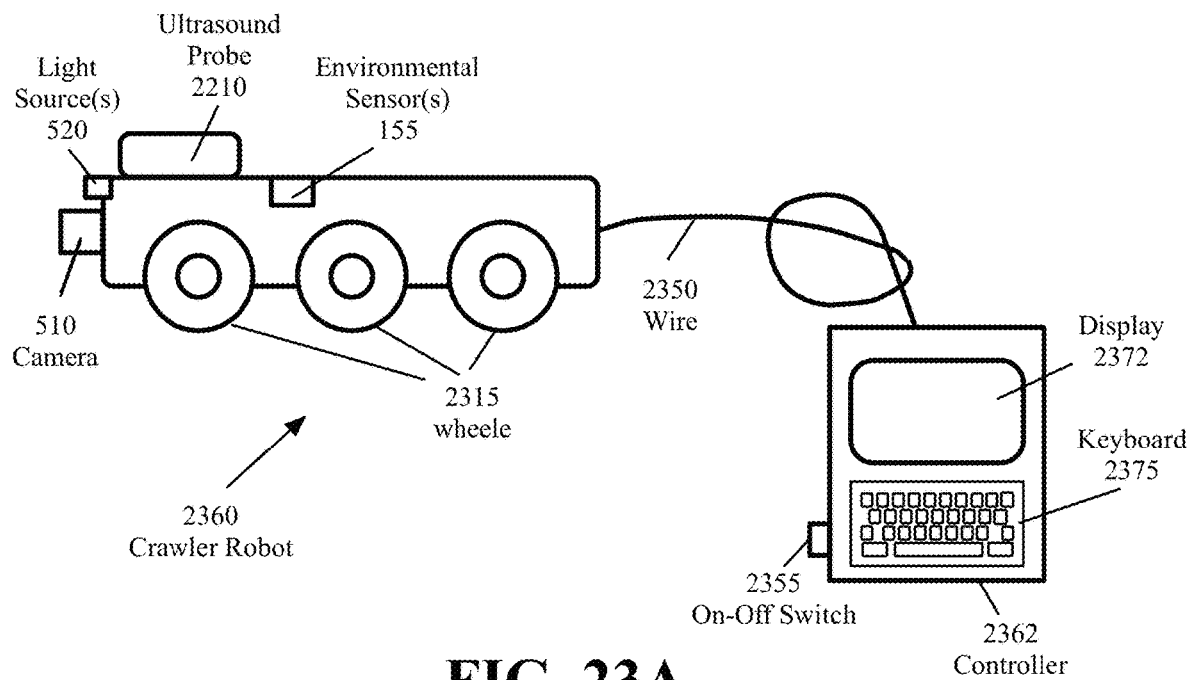
FIG. 23A is a schematic front view of a custom-made crawler robot and the associated ultrasound probe and controller, according to different aspects of the present disclosure.
Figure 23B:
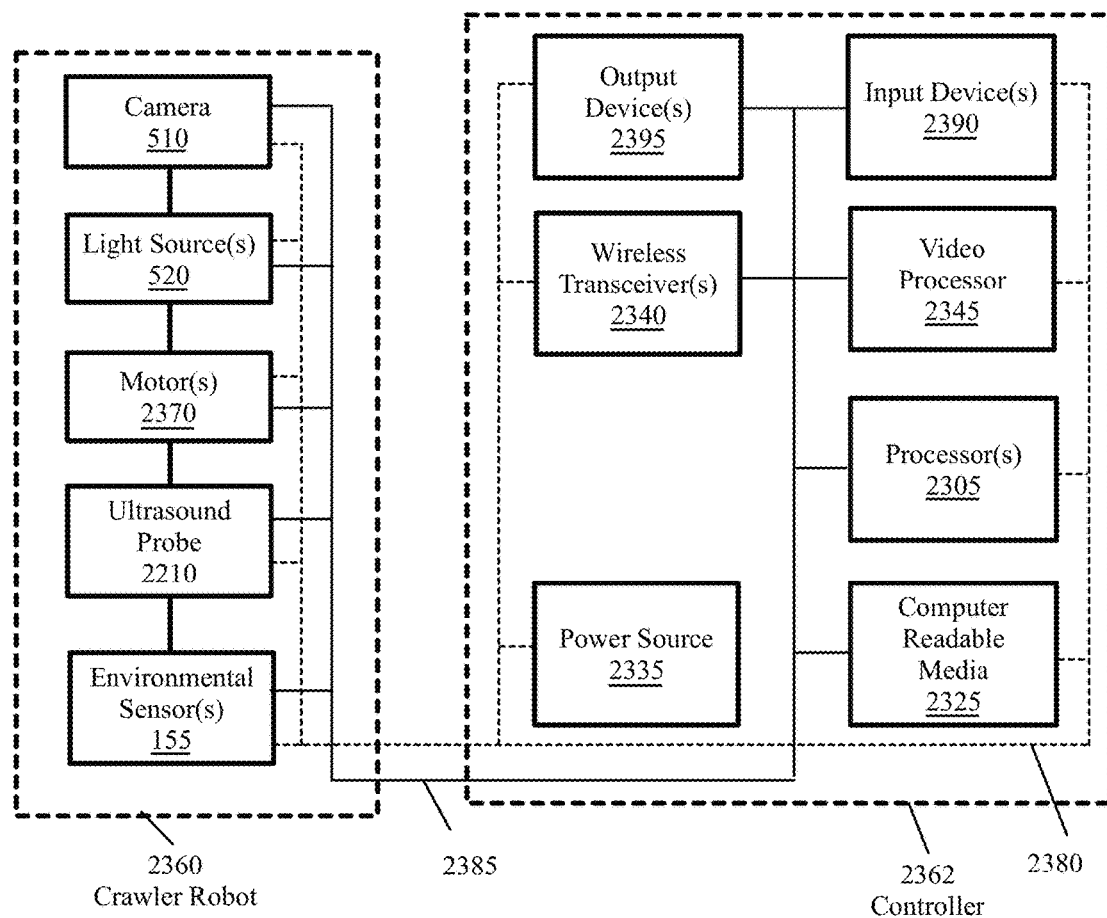
FIG. 23B is a functional block diagram of the components of custom-made crawler robot of FIG. 23A, according to different aspects of the present disclosure.

FIG. 23A is a schematic front view of a custom-made crawler robot and the associated ultrasound probe and controller, according to different aspects of the present disclosure. FIG. 23B is a functional block diagram of the components of custom-made crawler robot of FIG. 23A, according to different aspects of the present disclosure. With reference to FIGS. 23A-23B, the crawler robot 2360 may include an ultrasound probe 2210, one or more motors 2370, several wheels 2315, a controller 2362, a camera 510, and one or more light sources 520. The ultrasound probe 2210 and the controller 2362 are referred to as an ultrasound scanner. The ultrasound probe 2210 may be similar to the ultrasound probe 2210 of FIGS. 22A-22B and may provide similar functions. The camera 510 and light source(s) 520 may be used to capture images of the interior of an exterior elevated element to detect wood rot on wood surfaces and rust on metallic surfaces, as described above. In addition to, or in lieu of being used for rot and rust detection, the camera 510 and light source(s) 520 may be used to display images on the display 2372 to allow an operator to navigate the crawler robot 2360 in the interior space of an exterior elevated element.

Some of the crawler robots of the present embodiments may include one or more environmental sensors 155, which may be similar to the environmental sensors 155 described above. The controller 2362 may be a computing device with a display 2372, a keyboard 2375, and an on-off switch 2355. The controller 2362 may include one or more processor 2305, one or more computer readable media 2325, one or more wireless transceivers 2340, a power source 2335, one or more input devices 2390, and/or one or more output devices 2395. The processor(s) 2305 may control the operations of the ultrasound probe 2210 through the on-off switch 2360, the keyboard 2375, and the display 2370.

The processor(s) 2305 may control the movements of the crawler robot 2360 through the motor(s) 2370. The processor(s) 2305 may receive commands through the display 2372 (e.g., when the display is a touchscreen) and/or the keyboard 2375 to move and steer the crawler robot inside the interior space of an exterior elevated element of a building. The processor(s) 2305 may send one or more signals to the motor(s) 2370 to rotate the wheels 2315 and/or to turn the wheels 2315 left or right. The processor(s) 2305 may receive the ultrasound echo recordings from the ultrasound probe 2210 and may generate visible images from the ultrasound recordings. The processor(s) 2305 may analyze the images generated from the ultrasound echo recordings to identify wood rot on the wood surfaces and/or may display the images on the display 2372.

The controller 2362 may include a power source 2335 that may provide power to different components of the controller 2362 and the crawler robot 2360 through one or more wires 2380. The power source 2335 may include a power adapter that may connect to an alternative current (AC) outlet. In addition to, or in lieu of the power adapter, the power source 2335 may include one or more batteries that may be rechargeable and/or replaceable.

The controller 2362 may include one or more wireless (e.g., and without limitations, Wi-Fi or Bluetooth) transceivers 2340 to provide wireless connectivity with an external electronic device. In addition to, or in lieu of the wireless transceivers 2340, the controller 2362 may include wired connectivity through the network(s) 190 (FIGS. 1A-1B) with one or more external devices. Different components of the crawler robot 2360 and/or the controller 2362 may be connected to each other by several wires 2385

The input device(s) 2390 may include the keyboard 2375. The output device(s) 2395 may include the display 2370. In some embodiments, the display 2370 may be a touchscreen display and may function as both an input and an output device.

Referring back to FIG. 21, ultrasound waves may be generated (At block 2120) by the ultrasound probe. For example, the ultrasound probe may direct ultrasound waves towards different surface of the interior space of the balcony. The ultrasound waves reflected (or echoed) from the surfaces in the interior space of the balcony may be recorded (at block 2125) by the ultrasound probe. One or more images may be generated (at block 2130) from the reflected ultrasound waves. The images may be visible image generated from the recorded echoes. For example, the ultrasound probe 2210 of FIGS. 22A-22B and 23A-23B may direct ultrasound waves towards different surface of the interior space of the balcony and may record the reflected waves. The processor(s) 2205 of FIGS. 22A-22B or the processor(s) 2305 of FIGS. 23A-23B may generate visible images from the recorded ultrasound echoes.

The images generated from the reflected ultrasound waves may be analyzed (at block 2135) to identify luminance differences of the wooden surfaces and/or the shape and the size of any cracks on the wooden surfaces. The existence of wood rot may be determined (at block 2140), based on the analysis, in the interior space of the balcony between the two wooden joists. Using ultrasound waves to generate visible images from the ultrasound waves that are reflected from the surfaces in the interior of an exterior elevated element of a building, such as a balcony, provides the technical advantage of providing images from the surfaces that may not be in direct line of sight of a visible light, or infrared light, camera.

The ultrasound probe may be removed (at block 2145) from the interior space of the balcony. The hole may be sealed (at block 2150). The process 2100 may then end. The hole in, some embodiments, may be permanently sealed. For example, and without limitations, the hole may be filled with spackle paste, which may be made of gypsum powder and other binders. Once the spackle paste is applied and dries, it permanently seals (or paths) the hole. In other embodiments, the hole may be covered by a ventilation window (e.g., as described above with reference to FIGS. 6A-15), or may be plugged by a cap or plug that may be, for example, made of rubber, plastic, silicone, etc.

In some embodiments, the process 2100 may also pass one or more environmental sensors, such as, for example, a humidity sensor, a moisture sensor, a temperature sensor, etc., may be passed through the hole after the hole is drilled. The environmental sensors may, for example, be attached to the snake camera (e.g., as shown in FIG. 4A), connected to a crawler robot (e.g., as shown in FIG. 5), or etc. The environmental sensors may make measurements of parameters, such as humidity, moisture, and/or temperature, which may be used to determine whether the wood in the interior space of the balcony may need treatment.

Figure 24:
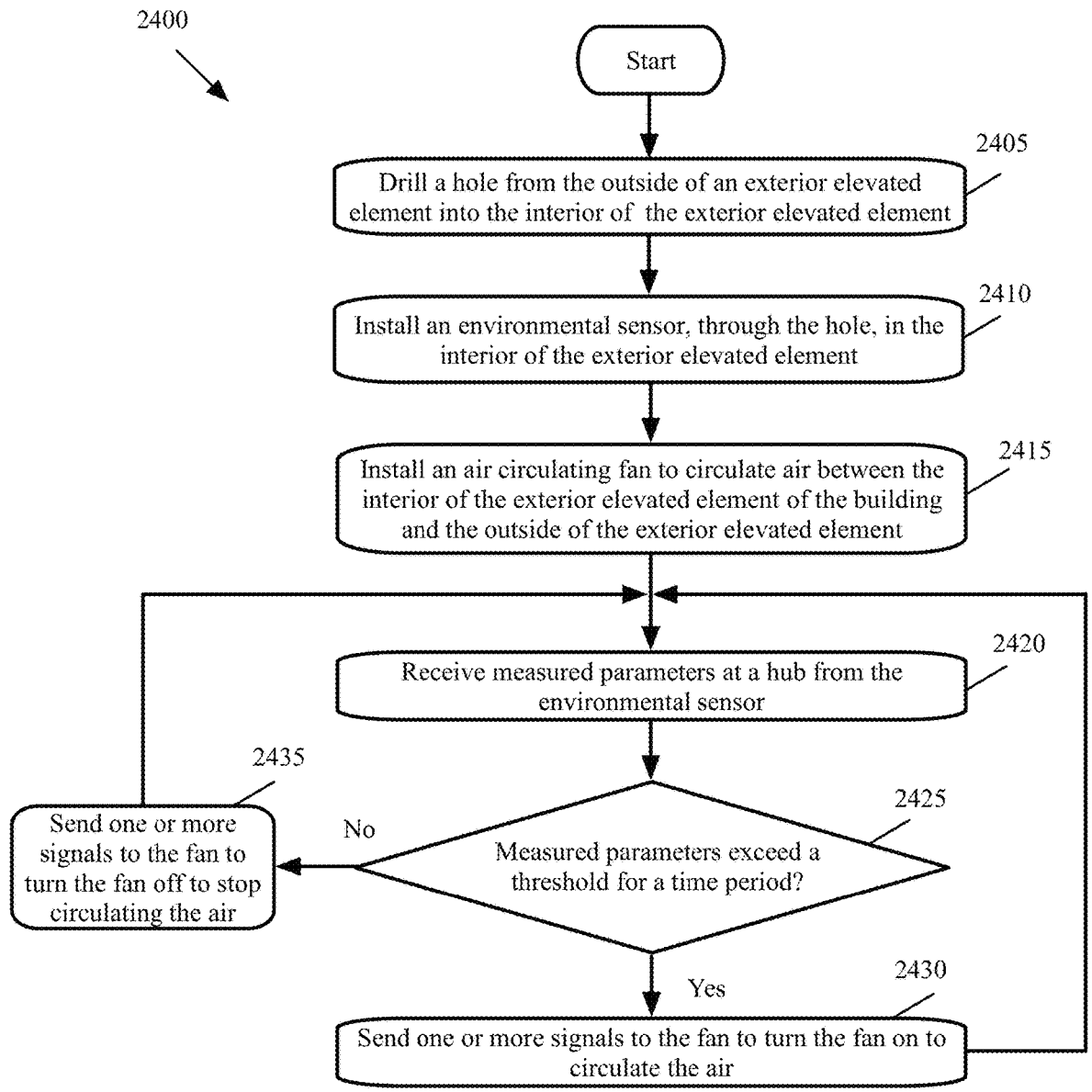
FIG. 24 is a flowchart illustrating an example process for installing a fan in the interior space of an exterior elevated element of a building and operating the fan based on parameters measured by an environmental sensor, according to various aspects of the present disclosure.

FIG. 24 is a flowchart illustrating an example process 2400 for installing a fan in the interior space of an exterior elevated element of a building and operating the fan based on parameters measured by an environmental sensor, according to various aspects of the present disclosure. The process 2400, in some of the present embodiments, may be performed for monitoring and maintaining the interior space of the exterior elevated element.

With reference to FIG. 24, a hole may be drilled (at block 2405) from the outside of an exterior elevated element into the interior space of the exterior elevated element. For example, a hole may be drilled into the interior of the exterior elevated element as described above with reference to FIGS. 1B and 3. An environmental sensor may be installed (at block 2410), through the hole, in the interior space of the exterior elevated element. The environmental sensor may be, for example, a humidity sensor, a moisture sensor, or a temperature sensor.

The environmental sensor may be connected by a plurality of wires to a controller that includes a processor and a network interface. For example, the environmental sensor 155 may be connected to a controller 150 that includes a processor 1605 and a network interface 1640, as described above with reference to FIG. 16. The network interface may be, for example, a wireless transceiver or a network interface card.

An air circulating fan may be installed (at block 2415) to circulate air between the interior of the exterior elevated element of the building and the outside of the exterior elevated element. For example, an air circulating fan 140 may be installed to circulate air between the interior of the exterior elevated element of the building and the outside of the exterior elevated element, as described above with reference to FIGS. 1B and 16.

Blocks 2420-2435 of the process 2400 of be performed by the processor 1605 (FIG. 16) of the controller 150 or by the processor 1705 (FIG. 17) of the hub 170. Measured parameters may be received (at block 2420) from the environmental sensor. For example, the measured parameters from the environmental sensor 155 may be received at the controller 150, as described above with reference to FIG. 16. The processor 1605 of the controller 150 may then send the measured parameters to the hub 170 through the network interface 1640.

A determination may be made (at block 2425) whether the measured parameters exceed a threshold. For example, the processor 1605 of the controller or the processor 1705 of the hub 170 may compare the measured parameters with a threshold to determine whether the measured parameters exceed the threshold for a time period. When the measured parameters exceed the threshold for the time period, one or more signals may be sent (at block 2430) to the fan to turn on the fan and circulate the air. The process 2400 may then proceed to block 2420, which was described above. When the measured parameters do not exceed the threshold for the time period, one or more signals may be sent (at block 2435) to the fan to turn the fan off to stop circulating the air. The process 2400 may then proceed to block 2420, which was described above.

Figure 25:
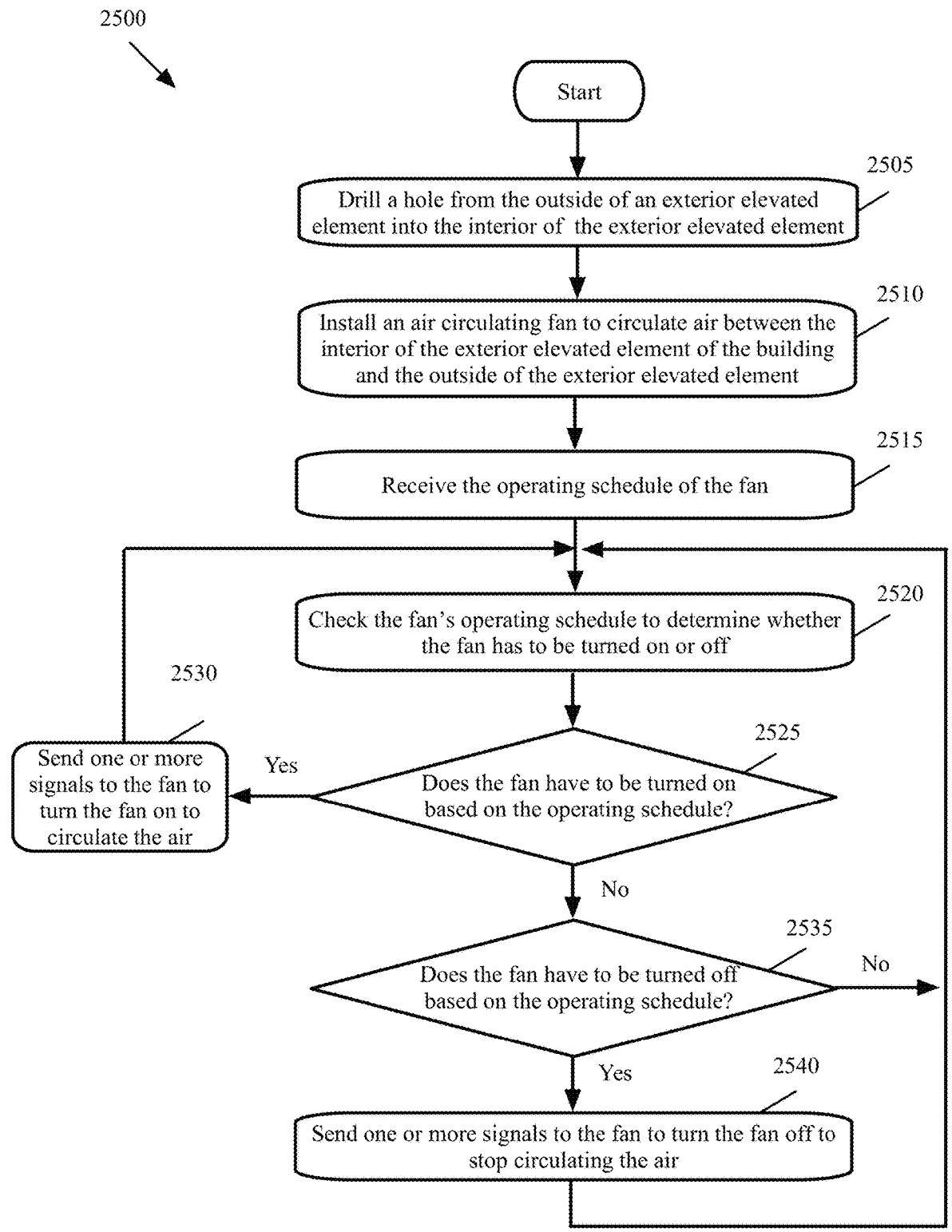
FIG. 25 is a flowchart illustrating an example process for installing a fan in the interior space of an exterior elevated element of a building and operating the fan based on an operating schedule, according to various aspects of the present disclosure.

FIG. 25 is a flowchart illustrating an example process 2500 for installing a fan in the interior space of an exterior elevated element of a building and operating the fan based on an operating schedule, according to various aspects of the present disclosure. The process 2500, in some of the present embodiments, may be performed for monitoring and maintaining the interior space of the exterior elevated element.

With reference to FIG. 25, a hole may be drilled (at block 2505) from the outside of an exterior elevated element into the interior space of the exterior elevated element. For example, a hole may be drilled into the interior of the exterior elevated element as described above with reference to FIGS. 1B and 3.

An air circulating fan may be installed (at block 2510) to circulate air between the interior of the exterior elevated element of the building and the outside of the exterior elevated element. For example, an air circulating fan 140 may be installed to circulate air between the interior of the exterior elevated element of the building and the outside of the exterior elevated element, as described above with reference to FIGS. 1B and 16.

Blocks 2515-2540 of the process 2500 of be performed by the processor 1605 (FIG. 16) of the controller 150 or by the processor 1705 (FIG. 17) of the hub 170. The operating schedule of the fan may be received (at block 2515). For example, the processor 1605 (FIG. 16) of the controller 150 or the processor 1705 (FIG. 17) of the hub 170 may receive the fan's operating schedule from an external electronic device, such as a client device 120 or a server 110 shown in FIG. 1B.

The fan's operating schedule may be checked (at block 2520) to determine whether the fan has to be turned on or off. For example, the processor 1605 of the controller or the processor 1705 of the hub 170 may periodically check the fan's operating schedule.

A determination may be made (at block 2525) whether the fan has to be turned on based on the operating schedule. If yes, one or more signals may be sent (at block 2530) to the fan to turn the fan on and circulate the air. For example, the processor 1605 of the controller or the processor 1705 of the hub 170 may send one or more signals to the fan to turn the fan on. The process 2500 may then proceed to block 2520, which was described above.

When a determination is made (at block 2525) that the fan does not have to be turned, a determination may be made (at block 2535) whether the fan has to be turned off based on the operating schedule. If yes, one or more signals may be sent (at block 2540) to the fan to turn the fan off to stop circulating the air. For example, the processor 1605 of the controller or the processor 1705 of the hub 170 may send one or more signals to the fan to turn the fan off. The process 2500 may then proceed to block 2520, which was described above.

Some embodiments may identify buildings that include exterior elevated elements that may require inspection. Some of the present embodiments may provide a method of automatically identifying the buildings that may include any exterior elevated elements. Some of these embodiments may use satellite images that are either publicly available through services such as, for example, and without limitations, Google Maps, Apple Maps, etc., or may use satellite images that may be purchased or licensed through third party providers.

Figure 26:
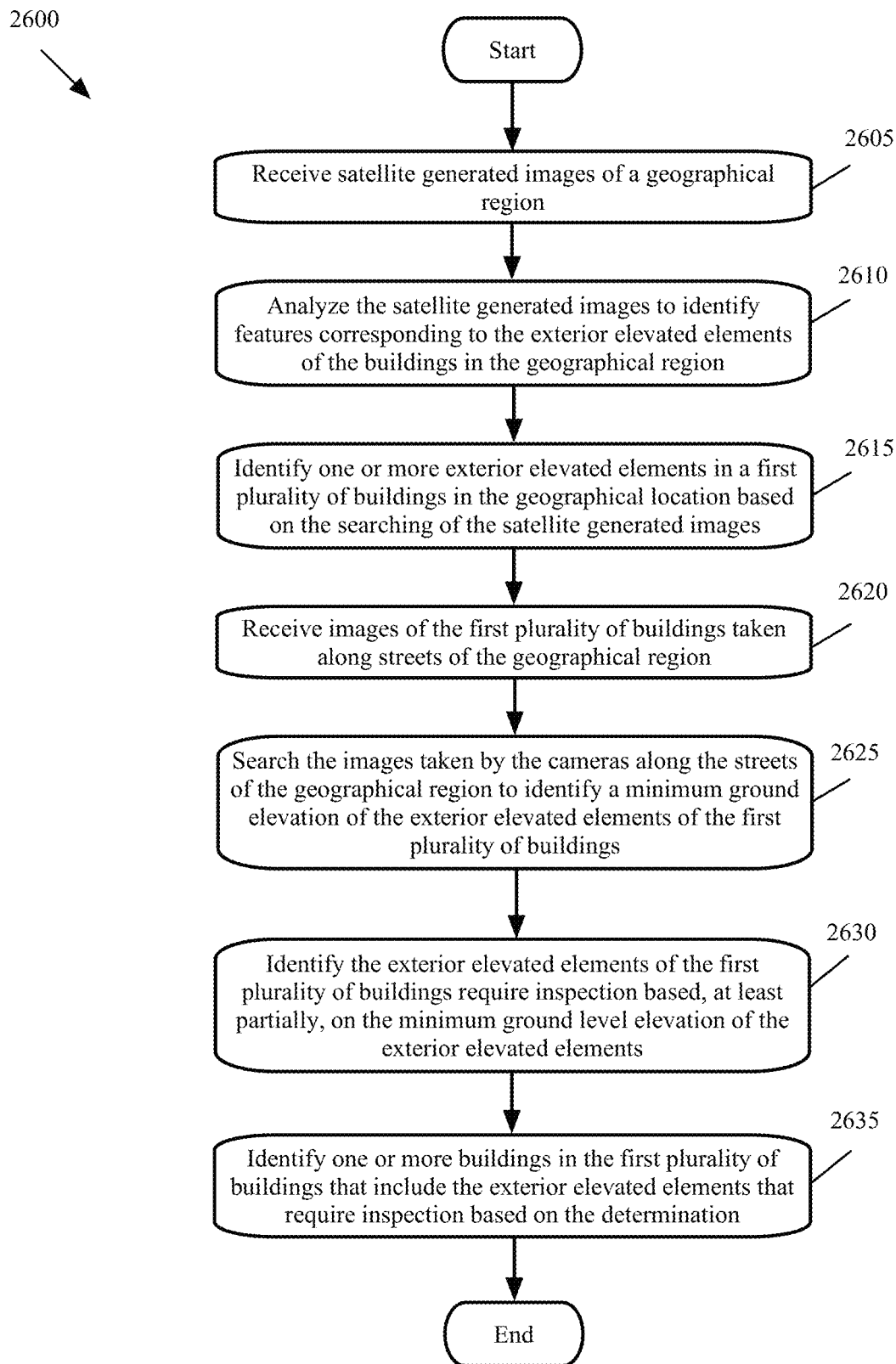
FIG. 26 is a flowchart illustrating an example process for identifying building with exterior elevated elements that may require inspection, according to various aspects of the present disclosure.

FIG. 26 is a flowchart illustrating an example process 2600 for identifying building with exterior elevated elements that may require inspection, according to various aspects of the present disclosure. The process 2600, in some of the present embodiments, may be performed by a processor of a server, such as the server(s) 110 of FIG. 1A.

With reference to FIG. 26, satellite generated images of a geographical region may be received (at block 2605). For example, the server(s) 110 (FIG. 1A) may receive satellite images that are taken from the geographical region. The satellite images may be publicly available satellite images, or satellite images that may be purchased or licensed through third party providers.

The satellite generated images may then be analyzed (at block 2610) to identify features corresponding to the exterior elevated elements of buildings in the geographical region. One or more exterior elevated elements may be identified (at block 2615) in a first plurality of buildings in the geographical location based on the analyses of the satellite generated images.

For examples, the server(s) 110 of FIG. 1A may search the images for features that corresponds to building structures. Once a building structure is identified, the server(s) 110 may search the exterior boundaries of the building structures for features related to exterior elevated elements, such as, balconies, decks, porches, stairways, landings, walkways, etc. In some embodiments, the server(s) 110 may include image processing software to analyze the images.

In some embodiments, the server(s) 110 may use AI, with an AI model that is trained with satellite generated images that include building structures with exterior elevated elements, satellite generated images that include building structures with no exterior elevated elements, and/or satellite generated images that include no building structures. The AI model may then be used to identify the buildings with exterior elevated elements in satellite images. In some embodiments, the AI may use a deep learning method, for example, to identify the buildings with exterior elevated elements in satellite images.

Images of the first plurality of buildings taken by cameras positioned along streets of geographical may be received (at block 2620). For example, the server(s) 110 may receive images from a service, such as Google Street View that are taken from street positions. The images may be taken from cameras installed on vehicles, cameras installed on bicycles, cameras carried by persons, etc.

The images taken by the cameras along the streets of the geographical region may be analyzed (at block 2625) to identify a minimum ground elevation of the exterior elevated elements of the first plurality of buildings. Identify (at block 2630) the exterior elevated elements of the first plurality of buildings that require inspection based, at least partially, on the minimum ground level elevation of the exterior elevated elements. For example, the server(s) 110 may determine the elevation of the underside of the exterior elevated elements from the grading level (or ground level) of the buildings by analyzing the images taken by the cameras along the streets. Typically, the exterior elevated elements that are close to the grading level (e.g., and without limitations, closer than six feet) may not require inspection by many municipalities.

One or more buildings in the first plurality of buildings may then be identified (at block 2635) that include the exterior elevated elements requiring inspection based on the determination. The process 2600 may then end. The list of such buildings may be provided to any interested party that may need a list of such buildings for building code enforcement, investment, advertisement (e.g., offering inspection services), etc. The process 26 may then end.

In addition to, or in lieu of using satellite images, some embodiments may provide tabulated data available from government agencies and third parties that list different attributes of buildings in a geographical region. Example of the building attributes that may be provided in this type of tabulated data may include, for example, and without limitations, name of the owner(s), the owner type (e.g., individual, trust, etc.), the owner(s) contact information, owners vesting rights (e.g., joint tenant, revocable trust, trust, survivor, family trust, community property, etc.), the situs direction (e.g., north, south, east, or west), the property's address, the property's legal description (e.g., lot and track number), the property's census track and block number, the property's latitude and longitude address, the land and the building areas, the year built, the data of the issuance of the certificate of opponency, number of bedroom, number of bathrooms, parking area, parking type, patio type, porch type, foundation type, room type, construction type (e.g., wood frame, metal frame, etc.), number of floors, flood zone code, name and address of the homeowner association (if any), etc.

The processor(s) of the server(s) 110, in some embodiments may analyze (e.g., at block 2610 of process 2600) the tabulated data to identify buildings that may or may not require inspection. For example, some embodiments may determine that a building is not wood frame or otherwise does not have a wood structure that may need inspection. Some states or municipalities may not require inspection for single story building, or for structures such as a balcony, that may be less than a threshold distance from ground.

In addition to, or in lieu, of the tabulated data, some embodiments may allow user entered data (e.g., entered by an owner, an inspector, a property manager, a buyer, a lender, etc.) to be used to determine whether or not a building may include exterior elevated elements and/or whether or not the exterior elevated elements may require inspection.

Figure 27:
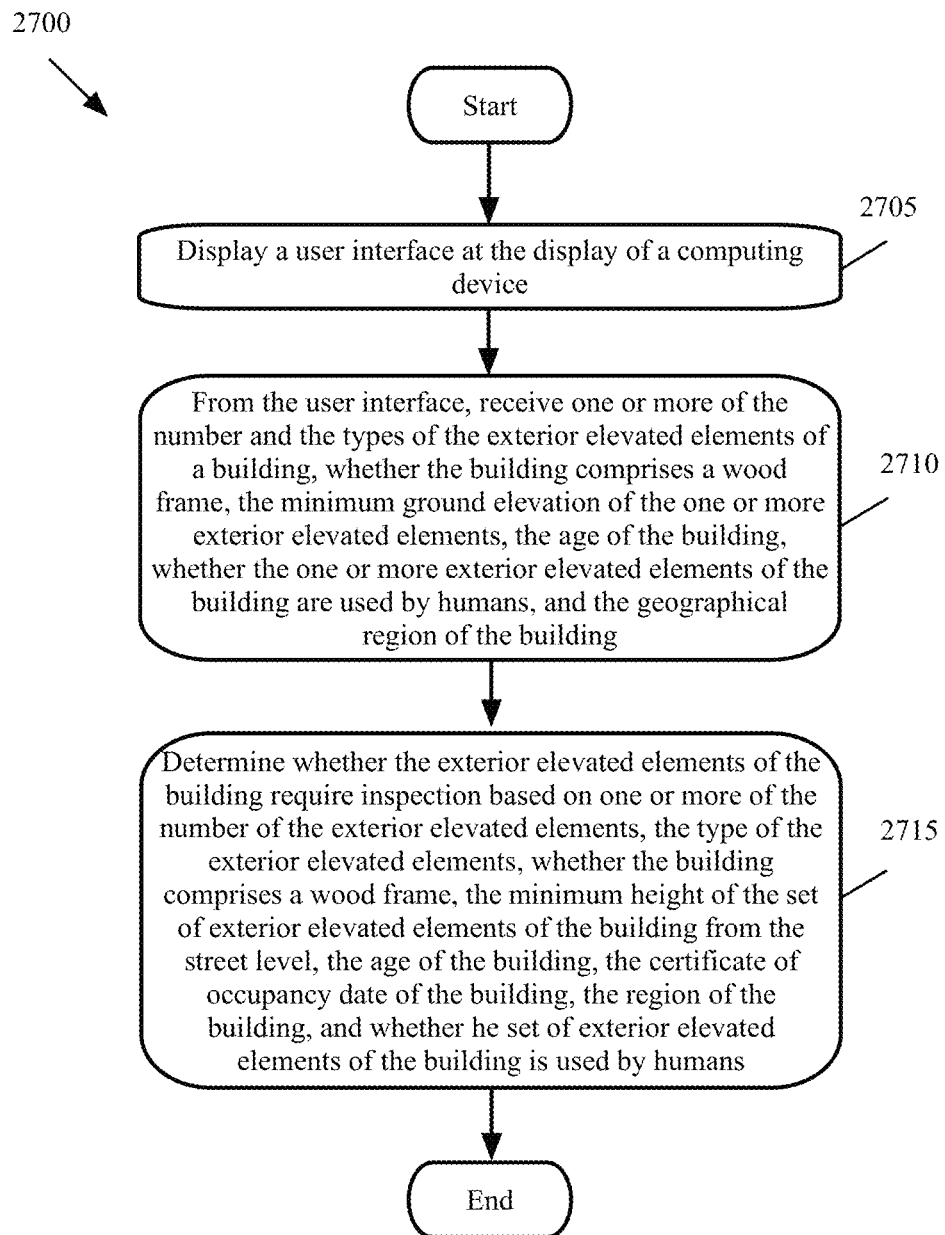
FIG. 27 is a flowchart illustrating an example process for identifying building with exterior elevated elements that may require inspection through a user interface of an electronic device, according to various aspects of the present disclosure.

FIG. 27 is a flowchart illustrating an example process 2700 for identifying building with exterior elevated elements that may require inspection through a user interface of an electronic device, according to various aspects of the present disclosure. The process 2700, in some of the present embodiments, may be performed by a processor of a sever, such as the server(s) 110 of FIG. 1A or by a processor of a client device, such as the client device(s) 120 of FIG. 1A.

Figure 28A:
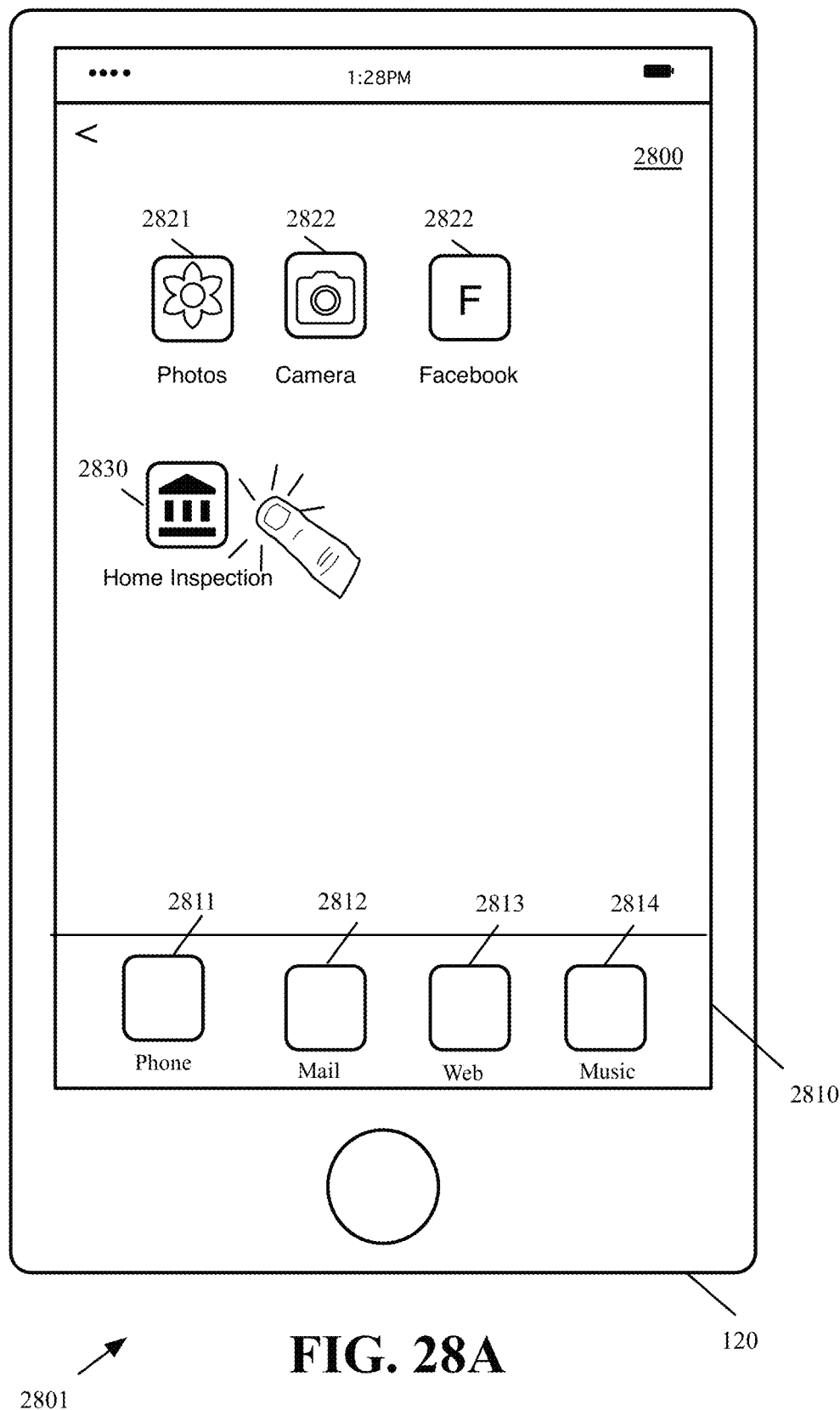
FIGS. 28A-28C illustrate a schematic front view of a client device that may include an application program for determining whether the exterior elevated elements of a building require inspection, according to various aspects of the present disclosure.
Figure 28B:
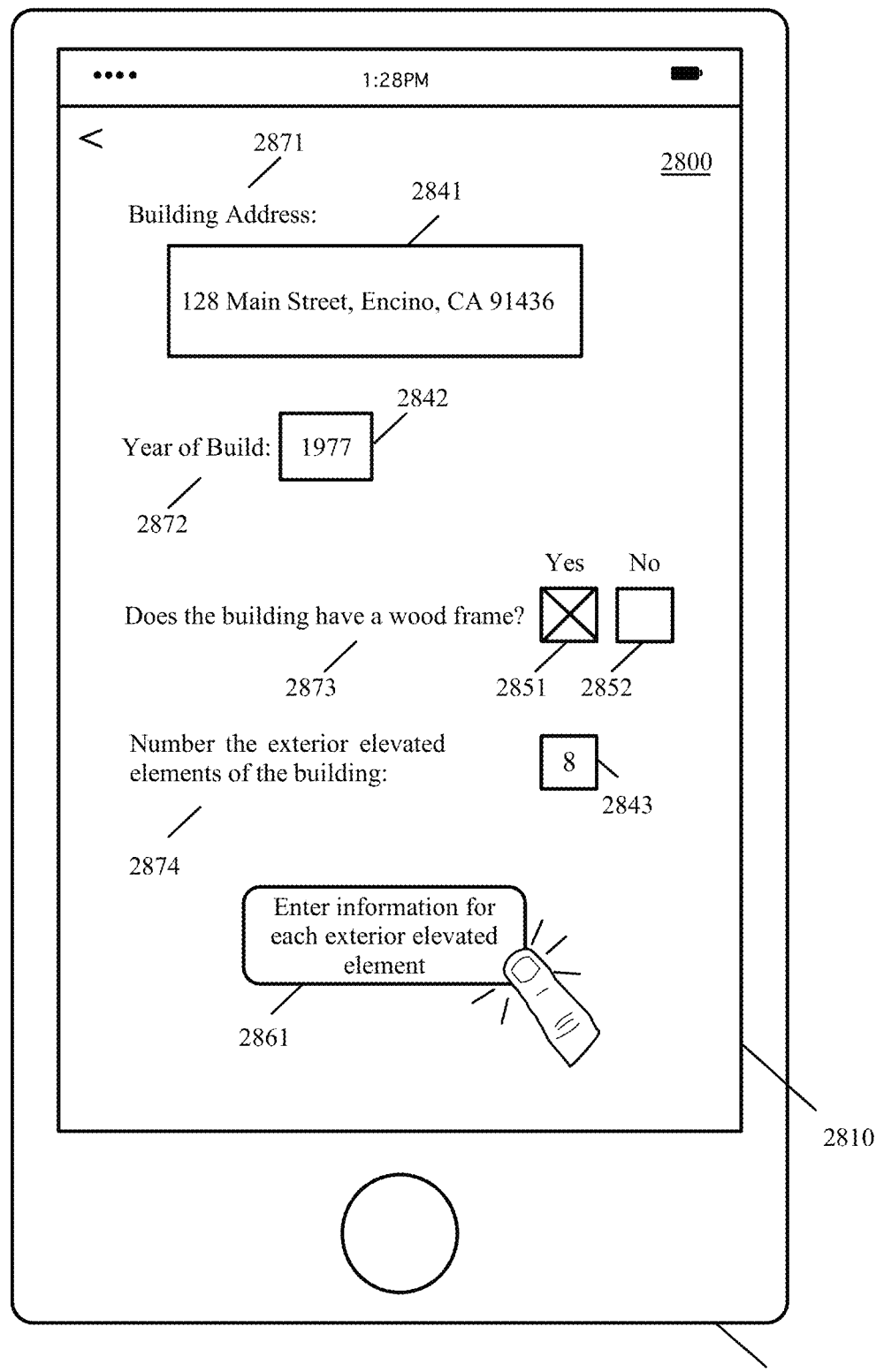
Figure 28C:
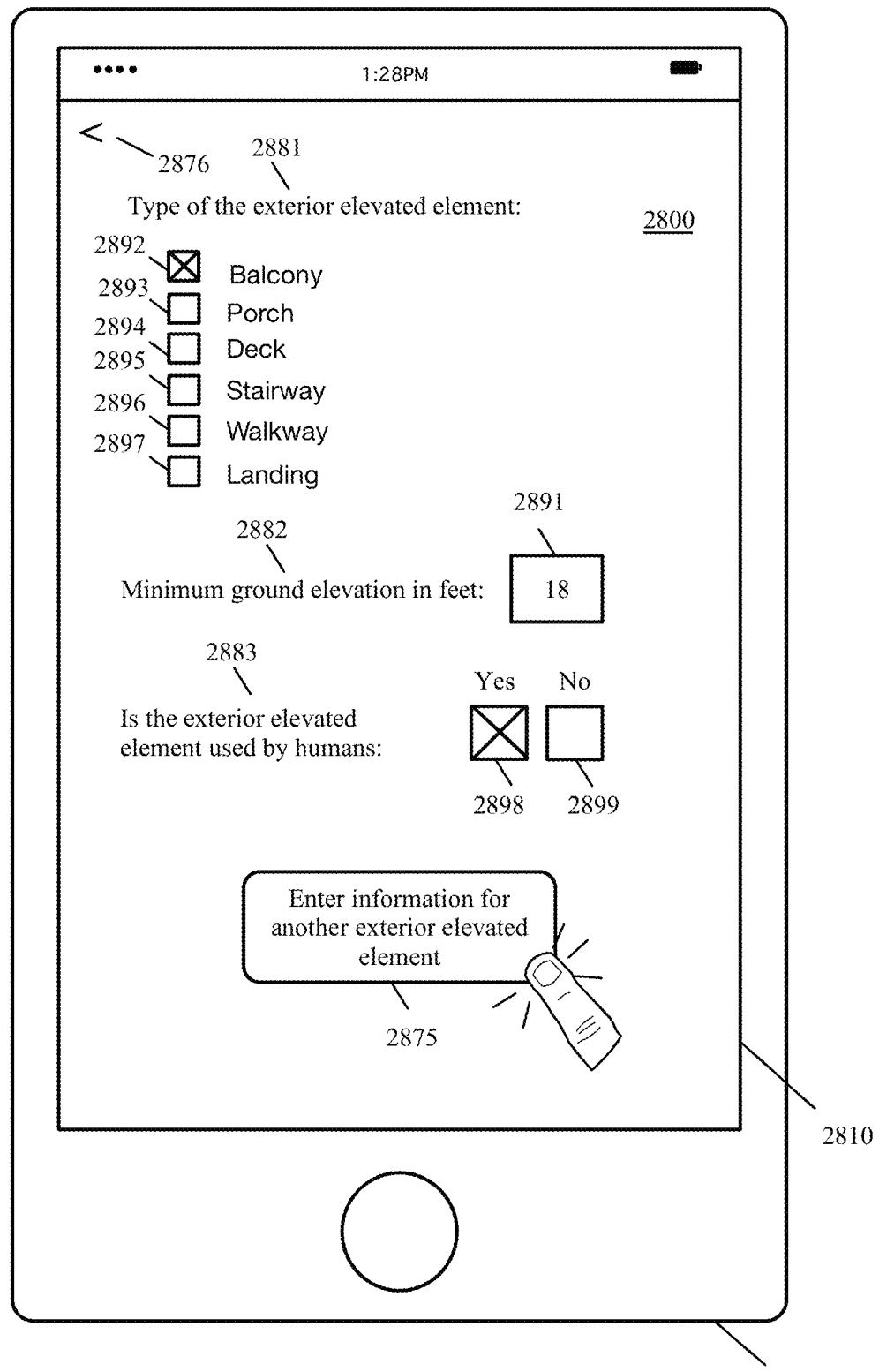

With reference to FIG. 27, a user interface may be displayed (at block 2705) at the display of a computing device. FIGS. 28A-28C illustrate a schematic front view of a client device 120 that may include an application program for determining whether the exterior elevated elements of a building require inspection, according to various aspects of the present disclosure. The figure illustrates, through three stages 2801-2803, a client device 120 using an application program 2830 to determine whether the exterior elevated elements of a building require inspection.

With reference to FIG. 28A, stage 2801 shows a user interface (UI) 2800 displayed on a display (e.g., a touchscreen) 2810 of the client device 120. The client device 120 may be any of the client device 120 of FIG. 1A.

The UI 2800 may include several selectable UI items (e.g., icons) of several applications 2811-2830. As shown, the home inspection application program 2830 may be selected in stage 2801. In response to the selection of the home inspection application program 2830, the UI 2800, in stage 2802, may display several display areas 2841-2843, several radio buttons 2851-2852, and an option 2861 to collect information regarding a building.

Referring back to FIG. 27, the process may receive (at block 2710) from the user interface, one or more of the number and the types of the exterior elevated elements of a building, whether the building comprises a wood frame, the minimum ground elevation of the one or more exterior elevated element, the age of the building, whether the one or more exterior elevated elements of the building are used by humans, and the geographical region of the building.

With reference to stage 2802 of FIG. 28B, the UI may request the address (as shown by 2871), the year of build (as shown by 2872), whether the building has a wood frame (as shown by 2873), and the number of the exterior elevated elements of the building (as shown by 2874). As shown, the user may have entered the requested information in the display areas 2841-2843 and through the radio buttons 2851-2852. The option 2861 may be selected in stage 2802 to provide information for each exterior elevated element of the building.

In response, the UI 2800, in stage 2803, may request the type of the exterior elevated element (as shown by 2881), the minimum ground elevation of the exterior elevated element (as shown by 2882), and whether the exterior elevated element is used by humans (as shown by 2883). As shown, the user may have entered the response in the display area 2891 and through the radio button 2892-2899. In stage 2803, the option 2875 may be selected to provide information for another exterior elevated element. The option 2876 may return the UI to the previous stage.

Referring back to FIG. 27, the process may determine (at block 2715) whether the exterior elevated elements of the building require inspection based on one or more of the number of the exterior elevated elements, the type of the exterior elevated elements, whether the building comprises a wood frame, the minimum height of the set of exterior elevated elements of the building from the street level, the age of the building, the certificate of occupancy date of the building, the region of the building, and whether he set of exterior elevated elements of the building is used by humans. The process 2700 may then end.

Figure 29:
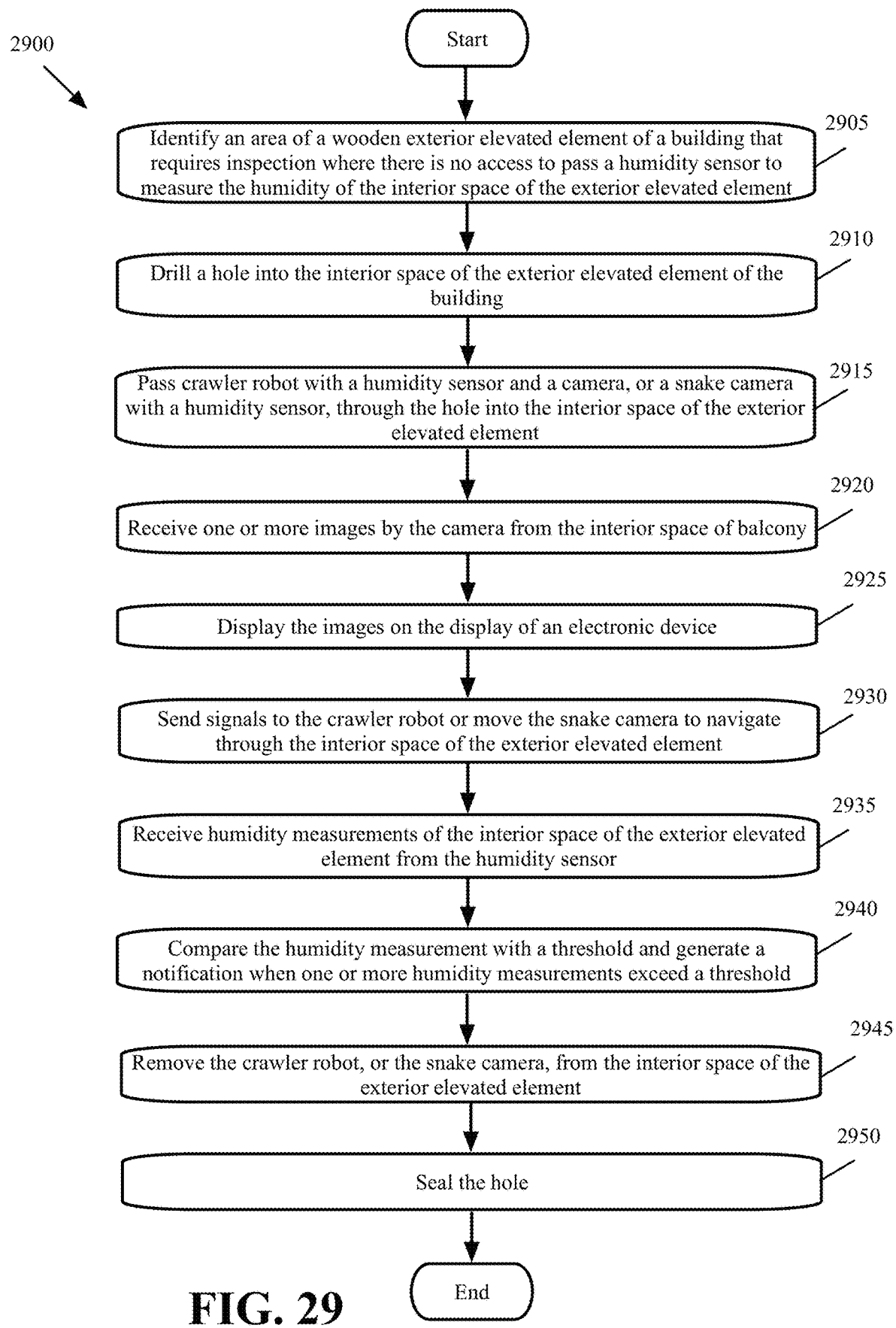
FIG. 29 is a flowchart illustrating an example process 2900 for measuring the humidity inside the interior space of an exterior elevated element of a building, according to various aspects of the present disclosure.

FIG. 29 is a flowchart illustrating an example process 2900 for measuring the humidity inside the interior space of an exterior elevated element of a building, according to various aspects of the present disclosure. The process 2900, in some of the present embodiments, may be performed during inspection of an exterior elevated element of a building.

With reference to FIG. 29, an area of a wooden exterior elevated element of a building may be identified (at block 2905) that requires inspection where there is no access to pass a humidity sensor to measure the humidity of the interior space of the exterior elevated element. An example of exterior elevated element of a building may include a balcony.

A hole may be drilled (at block 2910) into the interior space of an exterior elevated element of the building. For example, a hole may be drilled into the interior of the exterior elevated element as described above with reference to FIGS. 1A-1B and 3. In some embodiments, two wooden joists may be detected in the interior of the of the exterior elevated element using an electronic stud finder and the hole may be drilled between the two wooden joists.

Next, a crawler robot with a humidity sensor and a camera, or a snake camera with a humidity sensor, may be passed (at block 2915) through the hole into the interior space of the exterior elevated element. For example, a snake camera or a crawler robot may be passed into the interior space of the exterior elevated element as described above with reference to FIGS. 4A-4B and 5A-5D.

It should be noted that the frame of the crawler robot has to be configured with a form factor that allows the crawler robot to move in the interior space of an exterior elevated element, such as a balcony. For example, the height of the interior space of a balcony typically ranges from about 10 to 12 inches (approximately 25 to 30 cm), but this may vary depending on the specific design and construction of the exterior elevated element.

The distance between two adjacent joists in a balcony, also known as joist spacing, is typically 16 inches (40.6 cm) on center, though it can sometimes be 12 inches (approximately 30.5 cm) or 24 inches (approximately 61 cm) on center depending on the construction standards and load requirements. For a crawler robot to fit inside the balcony space, the crawler robot should have a form factor smaller than these dimensions. The crawler robot, in some embodiments, may be configured to have a height that does not exceed 10 inches (approximately 25 cm) and a width that allows it to maneuver between joists spaced at 16 inches (approximately 40.6 cm) or less. For example, the maximum width of the crawler robot, in some embodiments, may be configured to be less than 14.5 inches (approximately 36.8 cm) to allow the crawler robot to move between the joists.

One or more images of the interior space of the exterior elevated element may be received from the camera (at block 2920). For example, the process 405 of FIG. 4B may receive the images from the camera 410, or the processor 505 of FIG. 5B or 5D may receive the images captured by the camera 510. The images may be still images or videos.

The images may be displayed (at block 2925) on the display of an electronic device. for example, the images may be displayed on the display 495 of the controller 152 shown in FIG. 4B, on the display 572 of the controller 162 shown in FIGS. 5A-5D, or on the display of an electronic device 110 or 120 shown in FIG. 1A. The images may be used by an operator to navigate the crawler robot or the snake camera.

Signals may be sent (at block 2930) to the crawler robot, or the snake camera may be moved (at block 2930), to navigate the crawler robot, or the snake camera, through the interior space of the exterior elevated element. For example, the controller 162 of FIGS. 5A-5D may send signals to the motor(s) 570 of the crawler robot to rotate the wheels 515, or to turn the wheels 515 left or right to navigate the crawler robot. The snake camera 410 (FIG. 4A) may be moved through the interior space of the exterior elevated element using the flexible tube 450.

Humidity measurements of the interior space of the exterior elevated element may be received (at block 2935) from the humidity sensor. For example, the controller 152 (FIGS. 4A-4B) may receive humidity measurements from the humidity sensor (one of the environmental sensors 155), or the controller 162 (FIGS. 5A-5D) may receive humidity measurements from the humidity sensor (one of the environmental sensors 155).

The humidity measurements may be compared (at block 2940) with a threshold humidity value to determine whether the humidity inside the interior space of the exterior elevated element may cause dry rot to the wooden interior of the exterior elevated element. For example, the processor of an electronic device such as the controller 152, the controller 162, the client device 120, or the sever 110 may perform the comparison. In some embodiments, when one or more measurements exceed a threshold, the electronic device that is making the measurements may generate a warning (e.g., may display a message and/or send a notification to one or more other electronic devices) that the humidity inside the interior space may cause wood rot to the wooden surfaces inside the interior space. The humidity measurements may be stored. For example, the humidity measurements may be stored in the computer readable media 425 (FIG. 4B) or the computer readable media 525 (FIG. 5B).

The crawler robot, or the snake camera, may be removed (at block 2945) from the interior space of the exterior elevated element. The hole may be sealed (at block 2950). The hole in some embodiments may be permanently sealed. For example, and without limitations, the hole may be filled with spackle paste, which may be made of gypsum powder and other binders. Once the spackle paste is applied and dries, it permanently seals (or paths) the hole. In other embodiments, the hole may be covered by a ventilation window (e.g., as described above with reference to FIGS. 6A-15), or may be plugged by a cap or plug that may be, for example, made of rubber, plastic, silicone, etc. The process 2900 may then end.

Some of the above-described features and applications are implemented as software processes that are specified as a set of instructions recorded on a computer readable storage medium (also referred to as computer readable medium). When these instructions are executed by one or more processing unit(s) (e.g., one or more processors, cores of processors, or other processing units), they cause the processing unit(s) to perform the actions indicated in the instructions. Examples of computer readable media include, but are not limited to, CD-ROMs, flash drives, RAM chips, hard drives, EPROMs, etc. The computer readable media does not include carrier waves and electronic signals passing wirelessly or over wired connections.

In this specification, the term "software" is meant to include firmware residing in read-only memory or applications stored in magnetic storage, which may be read into memory for processing by a processor. Also, in some embodiments, multiple software inventions may be implemented as sub-parts of a larger program while remaining distinct software inventions. In some embodiments, multiple software inventions may also be implemented as separate programs. Finally, any combination of separate programs that together implement a software invention described here is within the scope of the invention. In some embodiments, the software programs, when installed to operate on one or more electronic systems, define one or more specific machine implementations that execute and perform the operations of the software programs.

Figure 30:
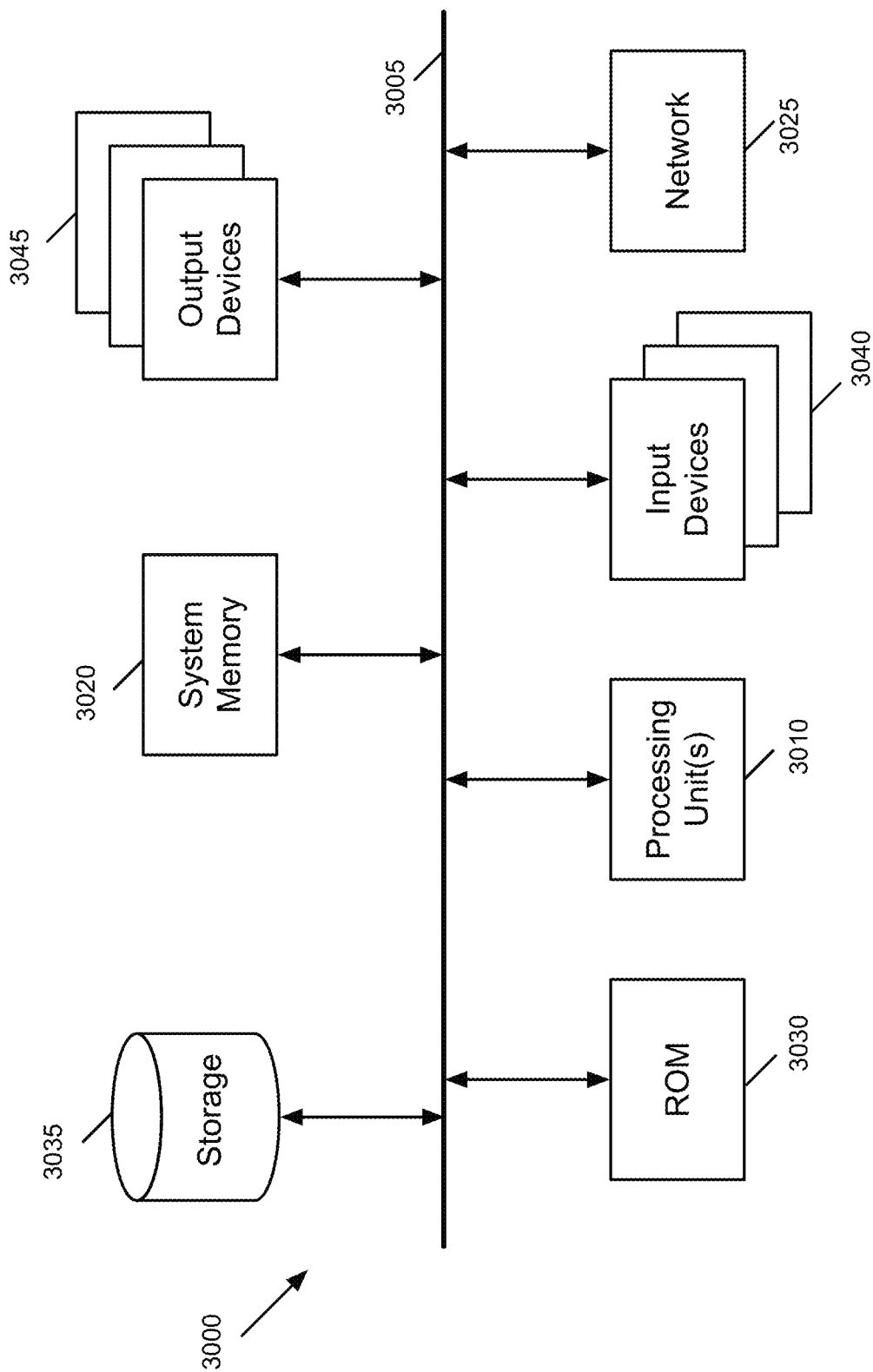
FIG. 30 conceptually illustrates an electronic system with which some embodiments of the invention are implemented.

FIG. 30 conceptually illustrates an electronic system 3000 with which some embodiments of the invention (e.g., the servers 110, the client devices 120 and 155, the snake cameras 150 and the associated controllers 152, the crawler robots 160 and the associated controllers 162, the hubs 170, the controllers 150, etc., described above) are implemented. The electronic system 3000 may be used to execute any of the control, virtualization, or operating system applications described above. The electronic system 3000 may be a computer (e.g., desktop computer, personal computer, tablet computer, server computer, mainframe, blade computer etc.), smartphone, PDA, or any other sort of electronic device. Such an electronic system includes various types of computer readable media and interfaces for various other types of computer readable media. The electronic system 3000 may include a bus 3005, processing unit(s) 3010, a system memory 3020, a read-only memory (ROM) 3030, a permanent storage device 3035, input devices 3040, and output devices 3045.

The bus 3005 collectively represents all system, peripheral, and chipset buses that communicatively connect the numerous internal devices of the electronic system 3000. For instance, the bus 3005 communicatively connects the processing unit(s) 3010 with the read-only memory 3030, the system memory 3020, and the permanent storage device 3035.

From these various memory units, the processing unit(s) 3010 retrieve(s) instructions to execute and data to process in order to execute the processes of the invention. The processing unit(s) may be a single processor or a multi-core processor in different embodiments.

The read-only-memory 3030 stores static data and instructions that are needed by the processing unit(s) 3010 and other modules of the electronic system. The permanent storage device 3035, on the other hand, is a read-and-write memory device. This device is a non-volatile memory unit that stores instructions and data even when the electronic system 3000 is off. Some embodiments of the invention use a mass-storage device (such as a magnetic or optical disk and its corresponding disk drive) as the permanent storage device 3035.

Other embodiments use a removable storage device (such as a flash drive, memory cards, etc.) as the permanent storage device Like the permanent storage device 3035, the system memory 3020 is a read-and-write memory device. However, unlike storage device 3035, the system memory is a volatile read-and-write memory, such as random access memory. The system memory stores some of the instructions and data that the processor needs at runtime. In some embodiments, the invention's processes are stored in the system memory 3020, the permanent storage device 3035, and/or the read-only memory 3030. From these various memory units, the processing unit(s) 3010 retrieve instructions to execute and data to process in order to execute the processes of some embodiments.

The bus 3005 also connects to the input and output devices 3040 and 3045. The input devices enable the user to communicate information and select commands to the electronic system. The input devices 3040 may include alphanumeric keyboards and pointing devices (also called "cursor control devices"). The input devices 3040, in some embodiments, may include cameras, sensors, microphones, near field communication (NFC) readers, and/or radio-frequency identification (RFID) readers. The input devices 3040, in some embodiments, may include pushbutton, switches, and/or knobs. The output devices 3045 may include printers, speakers, light sources (e.g., flashlights), and display devices, such as cathode ray tubes (CRT), liquid-crystal displays (LCD), light-emitting diode (LED) displays. Some embodiments may include devices, such as a touchscreen, that function as both input and output devices. The output devices 3045, in some embodiments, may display images generated and/or received by the electronic system.

Finally, as shown in FIG. 30, bus 3005 also couples electronic system 3000 to a network 3025 through a network adapter (not shown). In this manner, the computer may be a part of a network of computers (such as a local area network ("LAN"), a wide area network ("WAN"), an Intranet, or a network of networks, such as the Internet. Any or all components of electronic system 3000 may be used in conjunction with the invention.

Some embodiments include electronic components, such as microprocessors, storage, and memory, that store computer program instructions in a machine-readable or computer-readable medium (alternatively referred to as computer-readable storage media, machine-readable media, or machine-readable storage media). Some examples of such computer-readable media include RAM, ROM, read-only compact discs (CD-ROM), recordable compact discs (CD-R), rewritable compact discs (CD-RW), read-only digital versatile discs (e.g., DVD-ROM, dual-layer DVD-ROM), a variety of recordable/rewritable DVDs (e.g., DVD-RAM, DVD-RW, DVD+RW, etc.), flash memory (e.g., SD cards, mini-SD cards, micro-SD cards, etc.), magnetic and/or solid state hard drives, read-only and recordable Blu-Ray® discs, ultra-density optical discs, any other optical or magnetic media. The computer-readable media may store a computer program that is executable by at least one processing unit and includes sets of instructions for performing various operations. Examples of computer programs or computer code include machine code, such as is produced by a compiler, and files including higher-level code that are executed by a computer, an electronic component, or a microprocessor using an interpreter.

While the above discussion primarily refers to microprocessor or multi-core processors that execute software, some embodiments are performed by one or more integrated circuits, such as application specific integrated circuits (ASICs) or field programmable gate arrays (FPGAs). In some embodiments, such integrated circuits execute instructions that are stored on the circuit itself.

As used in this specification, the terms "computer", "server", "processor", and "memory" all refer to electronic or other technological devices. These terms exclude people or groups of people. For the purposes of the specification, the terms display or displaying means displaying on an electronic device. As used in this specification, the terms "computer readable medium," "computer readable media," and "machine readable medium" are entirely restricted to tangible, non-transitory, physical objects that store information in a form that is readable by a computer. These terms exclude any wireless signals, wired download signals, and any other ephemeral or transitory signals.

While the invention has been described with reference to numerous specific details, one of ordinary skill in the art will recognize that the invention may be embodied in other specific forms without departing from the spirit of the invention. In addition, a number of the figures conceptually illustrate processes. The specific operations of these processes may not be performed in the exact order shown and described. The specific operations may not be performed in one continuous series of operations, and different specific operations may be performed in different embodiments. Furthermore, the process could be implemented using several sub-processes, or as part of a larger macro process.

In a first aspect, a method of inspecting an exterior elevated element of a building is provide d. The method drills a hole into an interior space of the exterior elevated element of the building. The method passes a camera through the hole into the interior space of the exterior elevated element of the building. The interior space of the exterior elevated element encompasses a plurality of wooden surfaces. The method captures a set of one or more images from the wooden surfaces in the interior space of the exterior elevated element by the camera. The method, by the processor of an electronic device, analyzes the set of images to identify one or more of color differences of the wooden surfaces, color intensity differences of the wooden surfaces, and a shape and a size of any cracks on the wooden surfaces. The method determines an existence of wood rot in the interior space of the exterior elevated element based on the analysis.

In a second aspect, a method of identifying buildings with exterior elevated elements that require inspection is provided. The method receives a plurality of satellite generated images of a geographical region. The method, by the processor of a computing device, analyzes the plurality of satellite generated images to identify features corresponding to exterior elevated elements of buildings in the geographical region. The method identifies one or more exterior elevated elements in a first plurality of buildings in the geographical location based on the searching. The method receives images of the first plurality of buildings taken by cameras along streets in the geographical region. The method, by the processor of the computing device, analyzes the images taken by the cameras along the streets to identify a minimum ground elevation of the exterior elevated elements of the first plurality of buildings. The method, by the processor, determines whether the exterior elevated elements of the first plurality of buildings require inspection based, at least partially, on the minimum ground level elevation of the exterior elevated elements. The method identifies one or more buildings in the first plurality of buildings that include exterior elevated elements that require inspection based on the determination.

In an embodiment of the second aspect, the exterior elevated elements of the buildings comprise one or more of decks, porches, balconies, stairways, walkways, and landings.

In another embodiment of the second aspect, determining whether the exterior elevated elements of the first plurality of buildings require inspection further comprises: receiving tabulated data comprising one or more attributes of one or more buildings in the geographical region, comparing the attributes of the first plurality of buildings in the tabulated data with a set of values, and determining whether the exterior elevated elements of the first plurality of buildings require inspection based on the comparison.

In another embodiment of the second aspect, the attributes of a building comprise one or more of whether the building is owner occupied, an address of the building, a year of built of the building, a date of issuance of a certificate of opponency of the building, a number of floors of the building, and a construction type of the building frame.

In another embodiment of the second aspect, comparing the attributes of buildings in the tabulated data with a set of values comprises one or more of determining whether the property is owner occupied, whether the address of the building indicates that the building is in a particular zone, whether the year of built of the building is before the threshold date, whether the date of issuance of a certificate of opponency of the building is before the threshold date, whether the number of floors of the building is more than a threshold number, and whether the construction type of the building frame is wood.

An embodiment of the second aspect further comprises: by the processor, using artificial intelligence (AI) or machine learning (ML) to determine a cost and a duration of an inspection of the one or more buildings that require inspection.

In another embodiment of the second aspect, determining whether the exterior elevated elements of the first plurality of buildings require inspection further comprises determining whether the exterior elevated elements are for use by humans.

In a third aspect, a method of determining whether exterior elevated elements of a building require inspection is provided. The method, by a processor of a computing device, displaying a user interface at a display of the computing device. The method receives, from the user interface, one or more of: a number and a type of one or more exterior elevated elements of the building, whether the building comprises a wood frame, a minimum ground elevation of the one or more exterior elevated elements, an age of the building, a certificate of occupancy date of the building, whether the one or more exterior elevated elements of the building are used by humans, and a geographical region of the building. The method by the processor of the computing device, determines whether the exterior elevated elements of the building require inspection based on one or more of the number of the exterior elevated elements, the type of the exterior elevated elements, whether the building comprises a wood frame, the minimum height of the set of exterior elevated elements of the building from the street level, the age of the building, the certificate of occupancy date of the building, the region of the building, and whether he set of exterior elevated elements of the building is used by humans.

An embodiment of the third aspect further comprises receiving a plurality of street level images taken from the building, by the processor of the computing device, searching the plurality of street level images to identify dimensions of one or more of the exterior elevated elements of building, and by the processor of the computing device, using artificial intelligence (AI) or machine learning (ML) to determine a cost and a duration of an inspection of the building.

In a fourth aspect, a method of inspecting a balcony is provided. The method, from the outside of the balcony, detects locations of two wooden joists in an interior of the balcony. There is no access to pass a camera from the outside of the balcony into the interior space of the balcony between the two wooden joists, The interior space of the balcony between the two wooden joists is surrounded by several wooden surfaces including surfaces of the two wooden joists. The method drills a hole into the interior space of the balcony between the two wooden joists. The method passes the camera through the hole into the interior space of the balcony between the two wooden joists. The method captures one or more images by the camera from the wooden surfaces in the interior space of balcony. The method, by the processor of an electronic device, analyzes the one or more images to identify one or more of color differences of the wooden surfaces, color intensity differences of the wooden surfaces, and a shape and a size of any cracks on the wooden surfaces. The method determines the existence of wood rot in the interior space of the balcony based on the analysis. The method removes the camera from the interior space of the balcony. The method seals the hole.

In an embodiment of the fourth aspect, sealing the hole includes permanently patching the hole.

In another embodiment of the fourth aspect, sealing the hole includes inserting a removable plug into the hole.

In another embodiment of the fourth aspect, detecting two wooden joists in the interior of the balcony includes using an electronic stud finder.

In another embodiment of the fourth aspect, the wooden surfaces further include at least one of a ledger, a blocking, a docking lumber, or plywood.

In another embodiment of the fourth aspect, the camera is installed on a crawler robot, the crawler robot includes several wheels, one or more motors, and a controller connected by a several wires to the crawler robot. The controller includes a processor that is configured to send one or more signals to the one or more motors to move the crawler robot inside the interior space of the balcony and send one or more signals to the camera to turn the camera on or off.

In another embodiment of the fourth aspect, the camera is a snake camera connected by a flexible tube and several wires to a controller comprising a processor. The processor of the controller is configured to send one or more signals to the camera to turn the camera on or off.

An embodiment of the fourth aspect passes a humidity sensor into the hole and receives humidity measurements of the interior space of the balcony between the two wooden joists from the humidity sensor.

An embodiment of the fourth aspect passes a moisture sensor into the hole and receives moisture measurements of the interior space of the balcony between the two wooden joists from the humidity sensor.

Another embodiment of the fourth aspect passes a temperature sensor into the hole and receives temperature measurements of the interior space of the balcony between the two wooden joists from the humidity sensor.

In another embodiment of the fourth aspect, the one or more images comprise one or more still images or one or more video images.

Another embodiment of the fourth aspect transmits the one or more images to one or more remote electronic devices.

Another embodiment of the fourth aspect includes passing an ultrasound probe through the hole into the interior space of the balcony between the two wooden joists; transmitting ultrasound waves by the ultrasound probe; recording, by the ultrasound probe, ultrasound wave echoes reflected from the plurality of wooden surfaces in the interior space of balcony; generating one or more images from the recorded ultrasound wave echoes; by the processor of an electronic device, analyzing the one or more images generated from the recorded ultrasound wave echoes to identify one or more of luminance differences of the wooden surfaces, and a shape and a size of any cracks on the wooden surfaces; and determining an existence of wood rot in the interior space of the balcony based on the analysis.

In a fifth aspect, a method of inspecting a balcony is provided. The method identifies an area of the balcony where there is no access to pass a camera from an outside of the balcony into an interior space of the balcony. The interior space of the balcony encompasses a plurality of wooden surfaces. The method drills a hole into the interior space of the balcony in the identified area. The method passes the camera through the hole into the interior space of the balcony. The method captures one or more images from the wooden surfaces in the interior space of balcony by the camera. The method, by the processor of an electronic device, analyzes the one or more images to identify one or more of color differences of the wooden surfaces, color intensity differences of the wooden surfaces, and the shape and size of any cracks on the wooden surfaces. The method determines the existence of wood rot in the interior space of the balcony based on the analysis. The method removes the camera from the interior space of the balcony. The method seals the hole.

In an embodiment of the fifth aspect, sealing the hole includes permanently patching the hole.

In another embodiment of the fifth aspect, sealing the hole includes inserting a removable plug into the hole.

In another embodiment of the fifth aspect, the camera is installed on a crawler robot. The crawler robot includes several wheels, one or more motors, and a controller connected by several wires to the crawler robot. The controller includes a processor that is configured to send one or more signals to the one or more motors to move the crawler robot inside the interior space of the balcony and send one or more signals to the camera to turn the camera on or off.

In another embodiment of the fifth aspect, the camera is a snake camera connected by a flexible tube and several wires to a controller that includes a processor. The processor of the controller is configured to send one or more signals to the camera to turn the camera on or off.

In another embodiment of the fifth aspect, the one or more images include one or more still images or one or more video images.

An embodiment of the fifth aspect passes a humidity sensor into the hole and receives humidity measurements of the interior space of the balcony from the humidity sensor.

An embodiment of the fifth aspect passes a moisture sensor into the hole and receives moisture measurements of the interior space of the balcony from the humidity sensor.

Another embodiment of the fifth aspect passes a temperature sensor into the hole and receives temperature measurements of the interior space of the balcony between the two wooden joists from the humidity sensor.

Another embodiment of the fifth aspect transmits the one or more images to one or more external electronic devices.

Another aspect of the fifth embodiment passes an ultrasound probe through the hole into the interior space of the balcony; transmits ultrasound waves by the ultrasound probe; records, by the ultrasound probe, ultrasound wave echoes reflected from the plurality of wooden surfaces in the interior space of balcony; generates one or more images from the recorded ultrasound wave echoes; by the processor of an electronic device, analyzes the one or more images generated from the recorded ultrasound wave echoes to identify one or more of luminance differences of the wooden surfaces, and a shape and a size of any cracks on the wooden surfaces; and determines the existence of wood rot in the interior space of the balcony based on the analysis.

In a sixth aspect, a ventilation window for providing ventilation to an interior space of an exterior elevated element of a building is provide. The exterior elevated element includes one of a deck, a porch, a balcony, a stairway, a walkway, and a landing. The ventilation window includes several railings and several brackets. Each bracket is attached to one or more ball bearings configured to move along a corresponding railing to bring the attached bracket to a vicinity of a joist in the interior space of the exterior elevated element. Each bracket is configured to be connected to a joist to install the ventilation window on an underside of the exterior elevated element. Each ball bearing is configured to be moved to bring the attached bracket to a vicinity of a joist in the interior space of the exterior elevated element. Each bracket is configured to be connected to a joist to install the ventilation window on the underside of the exterior elevated element.

In a seventh aspect, a method of inspecting a balcony is provided. The method identifies an area of the balcony where there is no access to pass a crawler robot from the outside of the balcony into the interior space of the balcony. The interior space of the balcony is surrounded by several wooden surfaces. The method drills a hole into the interior space of the balcony. the method passes the crawler robot through the hole into the interior space of the balcony, the crawler robot comprising a humidity sensor. The method, by the processor of an electronic device receives humidity measurements of the interior space of the balcony from the humidity sensor, compares the humidity measurements with a humidity threshold value, determines that at least one of the humidity sensor measurements exceeds the humidity threshold value, and generates a notification indicating the humidity in the interior space of the balcony exceeds the humidity threshold value based on the determination. The method removes the crawler robot from the interior space of the balcony and seals the hole.

An embodiment of the seventh access stores the humidity measurements of the interior space of the balcony in a memory of the electronic device.

In an embodiment of the seventh aspect, the electronic device is a first electronic device, the method further sends the humidity measurements to one or more electronic devices external to the first electronic device.

In another embodiment of the seventh aspect, the crawler robot further includes a camera. The method further receives, by the processor of the electronic device, several images captured by the camera of the crawler robot from the interior space of balcony. The method displays the images captured by the camera on a display of the electronic device. The method sends several signals to the crawler robot to navigate through the wooden surfaces in the interior space of the balcony.

In another embodiment of the seventh aspect, the crawler robot further includes one or more motors. The method further sends several signals from the processor of the electronic device to the one or more motors to move the camera of the crawler robot in different directions.

In another embodiment of the seventh aspect, the crawler robot further includes several wheels and one or more motors. The method further sends several signals from the processor of the electronic device to the one or more motors to rotate the plurality wheels of the crawler robot, or move the plurality wheels of the crawler robot to left or right, to navigate the crawler robot inside the interior space of the balcony.

In another embodiment of the seventh aspect, the processor of the electronic device communicates with the crawler robot through one or more wires.

In another embodiment of the seventh aspect, the electronic device includes a wireless transceiver, the crawler robot includes a wireless transceiver, and the processor of the electronic device wirelessly communicates with the crawler robot through the wireless transducer of the electronic device and the wireless transducer of the crawler robot.

In another embodiment of the seventh aspect, sealing the hole includes permanently patching the hole.

In another embodiment of the seventh aspect, sealing the hole includes inserting a removable plug into the hole.

In another embodiment of the seventh aspect, drilling the hole into the interior space of the balcony includes detecting two wooden joists in the interior of the balcony using an electronic stud finder and drilling the hole between the two wooden joists.

In another embodiment of the seventh aspect, the images include one or more still images or one or more video images.

In an eight aspect, a crawler robot is provided. The crawler robot includes a frame, a humidity sensor installed on the frame; a several wheels located on at least two sides of the frame, a set of one or more motors, and a processor. The frame is configured to pass through a hole into an interior space of a balcony. For example, the height of the crawler robot may not exceed 10 inches and the width of the crawler robot may not exceed 14.5 inches. The processor of the crawler robot is configured to receive a first plurality of signals from a processor of an electronic device to rotate the wheels of the crawler robot, or to move wheels of the crawler robot to left or right, to navigate the crawler robot inside the interior space of the balcony. The processor of the crawler robot is configured to send a second plurality of signals to the set of motors in response to receiving the first plurality of signals. The set of motors are configured to receive the second plurality of signals from the processor of the crawler robot and rotate the plurality wheels of the crawler robot, or move the plurality wheels of the crawler robot to left or right, to navigate the crawler robot inside the interior space of the balcony. The humidity sensor is configured to make a plurality of humidity measurements from the inside of the interior space of the balcony and send the plurality of humidity measurements to the processor of the electronic device.

In an embodiment of the eight aspect, the processor of the crawler robot is connected to the processor of the electronic device through one or more wires.

In another embodiment of the eight aspect, the humidity sensor is connected to the processor of the electronic device through one or more wires.

In another embodiment of the eight aspect, the crawler robot includes a wireless transceiver. The processor of the crawler robot is configured to communicate with the processor of the electronic device through the wireless transceiver of the crawler robot and a wireless transceiver of the electronic device.

In another embodiment of the eight aspect, the humidity sensor is wirelessly connected to the processor of the electronic device through a wireless transceiver of the electronic device.

In another embodiment of the eight aspect, the crawler robot further includes a camera. The processor of the crawler robot is further configured to receive several images from the camera and send the images to the processor of the electronic device.

In another embodiment of the eight aspect, the set of one or more motors is a first set of motors. The crawler robot further includes a second set of one or more motors. The processor of the crawler robot is further configured to receive a third plurality of signals from the processor of the electronic device to move the camera and send a fourth plurality of signals to the second set of motors in response to receiving the third plurality of signals. The second set of motors are configured to receive the fourth plurality of signals from the processor of the crawler robot and move the camera in response to receiving the fourth plurality of signals.

In another embodiment of the eight aspect, the images include one or more still images or one or more video images.

The above description presents the best mode contemplated for carrying out the present embodiments, and of the manner and process of practicing them, in such full, clear, concise, and exact terms as to enable any person skilled in the art to which they pertain to practice these embodiments. The present embodiments are, however, susceptible to modifications and alternate constructions from those discussed above that are fully equivalent. Consequently, the present invention is not limited to the particular embodiments disclosed. On the contrary, the present invention covers all modifications and alternate constructions coming within the spirit and scope of the present disclosure. For example, the steps in the processes described herein need not be performed in the same order as they have been presented and may be performed in any order(s). Further, steps that have been presented as being performed separately may in alternative embodiments be performed concurrently. Likewise, steps that have been presented as being performed concurrently may in alternative embodiments be performed separately.

What is claimed is:

1. A crawler robot, comprising:
   a frame;
   a humidity sensor installed on the frame;
   a plurality of wheels located on at least two sides of the frame;
   a camera;
   first and second sets of one or more motors; and
   a processor;
   wherein the frame is configured to pass through a hole into an interior space of a balcony;
   wherein the processor of the crawler robot is configured to:
      receive a first plurality of signals from a processor of an electronic device to rotate the plurality wheels of the crawler robot, or to move the plurality wheels of the crawler robot to left or right, to navigate the crawler robot inside the interior space of the balcony;
      send a second plurality of signals to the first set of motors in response to receiving the first plurality of signals;
      receive a third plurality of signals from the processor of the electronic device to move the camera; and
      send a fourth plurality of signals to the second set of motors in response to receiving the third plurality of signals;
   wherein the first set of motors are configured to receive the second plurality of signals from the processor of the crawler robot and rotate the plurality wheels of the crawler robot, or move the plurality wheels of the crawler robot to left or right, to navigate the crawler robot inside the interior space of the balcony;
   wherein the second set of motors are configured to:
      receive the fourth plurality of signals from the processor of the crawler robot; and
      move the camera in response to receiving the fourth plurality of signals; and
   wherein the humidity sensor is configured to:
      make a plurality of humidity measurements from the inside of the interior space of the balcony; and
      send the plurality of humidity measurements to the processor of the electronic device.

2. The crawler robot of claim 1, wherein the processor of the crawler robot is connected to the processor of the electronic device through one or more wires.

3. The crawler robot of claim 1, wherein the humidity sensor is connected to the processor of the electronic device through one or more wires.

4. The crawler robot of claim 1 further comprising:
   a wireless transceiver,
   wherein the processor of the crawler robot is configured to communicate with the processor of the electronic device through the wireless transceiver of the crawler robot and a wireless transceiver of the electronic device.

5. The crawler robot of claim 1 further comprising:
   a wireless transceiver,
   wherein the humidity sensor is wirelessly connected to the processor of the electronic device through the wireless transceiver of the crawler robot and a wireless transceiver of the electronic device.

6. The crawler robot of claim 1, wherein the processor of the crawler robot is further configured to:
   receive a plurality of images from the camera; and
   send the plurality of images to the processor of the electronic device.

7. The crawler robot of claim 6, wherein the plurality of images comprises one or more still images or one or more video images.

* * * * *